(12) United States Patent
Steinman et al.

(10) Patent No.: US 10,034,915 B2
(45) Date of Patent: Jul. 31, 2018

(54) SMALL HEAT SHOCK PROTEINS AND ACTIVE FRAGMENTS THEREOF AS A THERAPY FOR INFLAMMATION AND ISCHEMIA

(75) Inventors: Lawrence Steinman, Stanford, CA (US); Jonathan Rothbard, Sonoma, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 13/531,114

(22) Filed: Jun. 22, 2012

(65) Prior Publication Data

US 2013/0071392 A1    Mar. 21, 2013

Related U.S. Application Data

(60) Provisional application No. 61/571,285, filed on Jun. 23, 2011.

(51) Int. Cl.
| | |
|---|---|
| *C07K 7/08* | (2006.01) |
| *A61K 38/04* | (2006.01) |
| *A61K 38/17* | (2006.01) |
| *A61K 39/44* | (2006.01) |
| *C07K 14/47* | (2006.01) |

(52) U.S. Cl.
CPC ............ *A61K 38/17* (2013.01); *A61K 39/44* (2013.01); *C07K 14/47* (2013.01); *C07K 7/08* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,022,859 A | 2/2000 | Kiessling et al. | |
| 6,780,971 B2 | 8/2004 | Wolozin et al. | |
| 7,875,589 B2* | 1/2011 | Steinman et al. | ........... 514/16.6 |
| 2004/0132190 A1 | 7/2004 | Dillmann et al. | |
| 2005/0013824 A1 | 1/2005 | Van Noort et al. | |
| 2007/0179087 A1 | 8/2007 | Gelfand et al. | |
| 2007/0185028 A1 | 8/2007 | Ghosh et al. | |
| 2008/0138353 A1* | 6/2008 | Steinman et al. | ......... 424/178.1 |
| 2008/0227700 A1 | 9/2008 | Ghosh et al. | |
| 2008/0280824 A1 | 11/2008 | Ghosh et al. | |
| 2010/0004168 A1 | 1/2010 | Gehlbach et al. | |
| 2010/0150868 A1* | 6/2010 | Achiron et al. | . G01N 33/56972 424/85.6 |
| 2011/0160142 A1* | 6/2011 | Steinman et al. | ........... 514/17.9 |
| 2011/0318346 A1* | 12/2011 | Steinman et al. | ......... 424/134.1 |

FOREIGN PATENT DOCUMENTS

WO    WO 2011/085081 A2 *    7/2011

OTHER PUBLICATIONS

National Institute of Neurological Disorders and Stroke, "Multiple Sclerosis: Hope Through Research: National Institute of Neurological Disorders", Mar. 3, 2015, http://www.ninds.nih.gov/disorders/multiple_sclerosis/detail_multiple_sclerosis.htm, retrieved Mar. 27, 2015.*
Verma et al., "Routes of Drug Administration", International Journal of Pharmaceutical Studies and Research, 1:54-59, 2010.*
Badin; et al. "Protective effect of post-ischaemic viral delivery of heat shock proteins in vivo", J Cereb Blood Flow Metab (Feb. 2009), 29(2):254-263.
Bhattacharyya; et al. "Mini-alphaB-crystallin: a functional element of alphaB-crystallin with chaperone-like activity", Biochemistry (Mar. 2006), 45(9):3069-3076.
Chabas; et al. "The influence of the proinflammatory cytokine, osteopontin, on autoimmune demyelinating disease", Science (Nov. 2001), 294(5547):1731-1735.
Chou; et al. "CD4 T-cell epitopes of human alpha B-crystallin", J Neurosci Res (Feb. 2004), 75(4):516-523.
Dubin; et al. "Human alpha B-crystallin gene and preferential promoter function in lens", Genomics (Aug. 1990), 7 (4):594-601.
Ghosh; et al. "Interactive domains for chaperone activity in the small heat shock protein, human alphaB crystallin", Biochemistry (Nov. 2005), 44(45):14854-14869.
Ghosh; et al. "Interactive sequences in the molecular chaperone, human alphaB crystallin modulate the fibrillation of amyloidogenic proteins", Int J Biochem Cell Biol (2008), 40(5):954-967.
Ghosh; et al. "The function of the beta3 interactive domain in the small heat shock protein and molecular chaperone, human alphaB crystallin", Cell Stress Chaperones (Jun. 2006), 11(2):187-197.
Johnson; et al. "Extended use of glatiramer acetate (Copaxone) is well tolerated and maintains its clinical effect on multiple sclerosis relapse rate and degree of disability", Neurology (Mar. 1998), 50(3):701-708.
Kumarapeli; et al. "Alpha B-crystallin suppresses pressure overload cardiac hypertrophy", Circ Res (Dec. 2008), 103(12):1473-1482.
Lee; et al. "Controlled delivery of heat shock protein using an injectable microsphere/hydrogel combination system for the treatment of myocardial infarction", J Control Release (Aug. 2009), 137(3):196-202.
Li; et al. "Calcium-activated RAF/MEK/ERK signaling pathway mediates p53-dependent apoptosis and is abrogated by alpha B-crystallin through inhibition of RAS activation", Mol Biol Cell (Sep. 2005), 16(9):4437-4453.
Lo; et al. "High level expression and secretion of Fc-X fusion proteins in mammalian cells", Protein Eng (Jun. 1998), 11(6):495-500.
Moss; et al. "Th1/Th2 cells in inflammatory disease states: therapeutic implications", Expert Opin Biol Ther (Dec. 2004), 4(12):1887-1896.

(Continued)

*Primary Examiner* — Ronald B Schwadron
(74) *Attorney, Agent, or Firm* — Pamela J. Sherwood; Bozicevic, Field & Francis LLP

(57) ABSTRACT

The invention provides methods for treating inflammatory diseases by administering to the subject an effective amount of specific peptides derived from HSPB5, where the dose is effective to suppress or prevent initiation, progression, or relapses of disease, including the progression of established disease.

2 Claims, 29 Drawing Sheets

(56) References Cited

OTHER PUBLICATIONS

Nagaraj; et al. "Dicarbonyl stress and apoptosis of vascular cells—Prevention by alpha 8-crystallin", Ann N Y Acad Sci (Jun. 2005), 1043:158-165.

Outeiro; et al. "Small heat shock proteins protect against alpha-synuclein-induced toxicity and aggregation", Biochem Biophys Res Commun (Dec. 2006), 351(3):631-638.

Raman; et al. "AlphaS-crystallin, a small heat-shock protein, prevents the amyloid fibril growth of an amyloid beta-peptide and beta2-microglobulin", Biochem J (Dec. 2005), 392(Pt 3):573-581.

Rekas; et al. "Interaction of the molecular chaperone alphaB-crystallin with alpha-synuclein: effects on amyloid fibril formation and chaperone activity", J Mol Biol (Jul. 2004), 340(5):1167-1183.

Roelofs; et al. "Identification of small heat shock protein 88 (HSP22) as a novel TLR4 ligand and potential involvement in the pathogenesis of rheumatoid arthritis", J Immunol (Jun. 2006), 176(11):7021-7027.

Sanbe; et al. "Interruption of CryAB-amyloid oligomer formation by HSP22", J Biol Chem (Jan. 2007), 282(1):555-563.

Santhoshkumar; et al. "Conserved F84 and P86 residues in alphaB-crystallin are essential to effectively prevent the aggregation of substrate proteins", Protein Sci (Nov. 2006), 15(11):2488-2498.

Sharma; et al. "Synthesis and characterization of a peptide identified as a functional element in alphaA-crystallin", J Biol Chem (Feb. 2000), 275(6):3767-3771.

Solomon; et al. "Monoclonal antibodies inhibit in vitro fibrillar aggregation of the Alzheimer beta-amyloid peptide", PNAS (Jan. 1996), 93(1):452-455.

Sotgiu; et al. "Alpha B-crystallin is not a dominant peripheral T-cell autoantigen in multiple sclerosis amongst Sardinians", Eur J Neurol (Sep. 2003), 10(5):583-586.

Thoua; et al. "Encephalitogenic and immunogenic potential of the stress protein alphaB-crystallin in Biozzi ABH (H-2A(g7)) mice", J Neuroimmunol (Apr. 2000), 104(1):47-57.

Van Stipdonk; et al. "T- and B-cell nonresponsiveness to self-alphaB-crystallin in SJL mice prevents the induction of experimental allergic encephalomyelitis", Cell Immunol (Sep. 2000), 204(2):128-134.

Van Stipdonk; et al. "Tolerance controls encephalitogenicity of alphaB-crystallin in the Lewis rat", J Neuroimmunol (Mar. 2000), 103(2):103-111.

Van Veen; et al. "[Alpha]B-crystallin genotype has impact on the multiple sclerosis phenotype", Neurology (Nov. 2003), 61(9):1245-1249.

Wang; et al. "Somatodendritic accumulation of misfolded SOD1-L 126Z in motor neurons mediates degeneration: alphaS-crystallin modulates aggregation", Hum Mol Genet (Aug. 2005), 14(16):2335-2347.

Wieske; et al. "Defined sequence segments of the small heat shock proteins HSP25 and alphaB-crystallin inhibit actin polymerization", Eur J Biochem (Apr. 2001), 268(7):2083-2090.

* cited by examiner

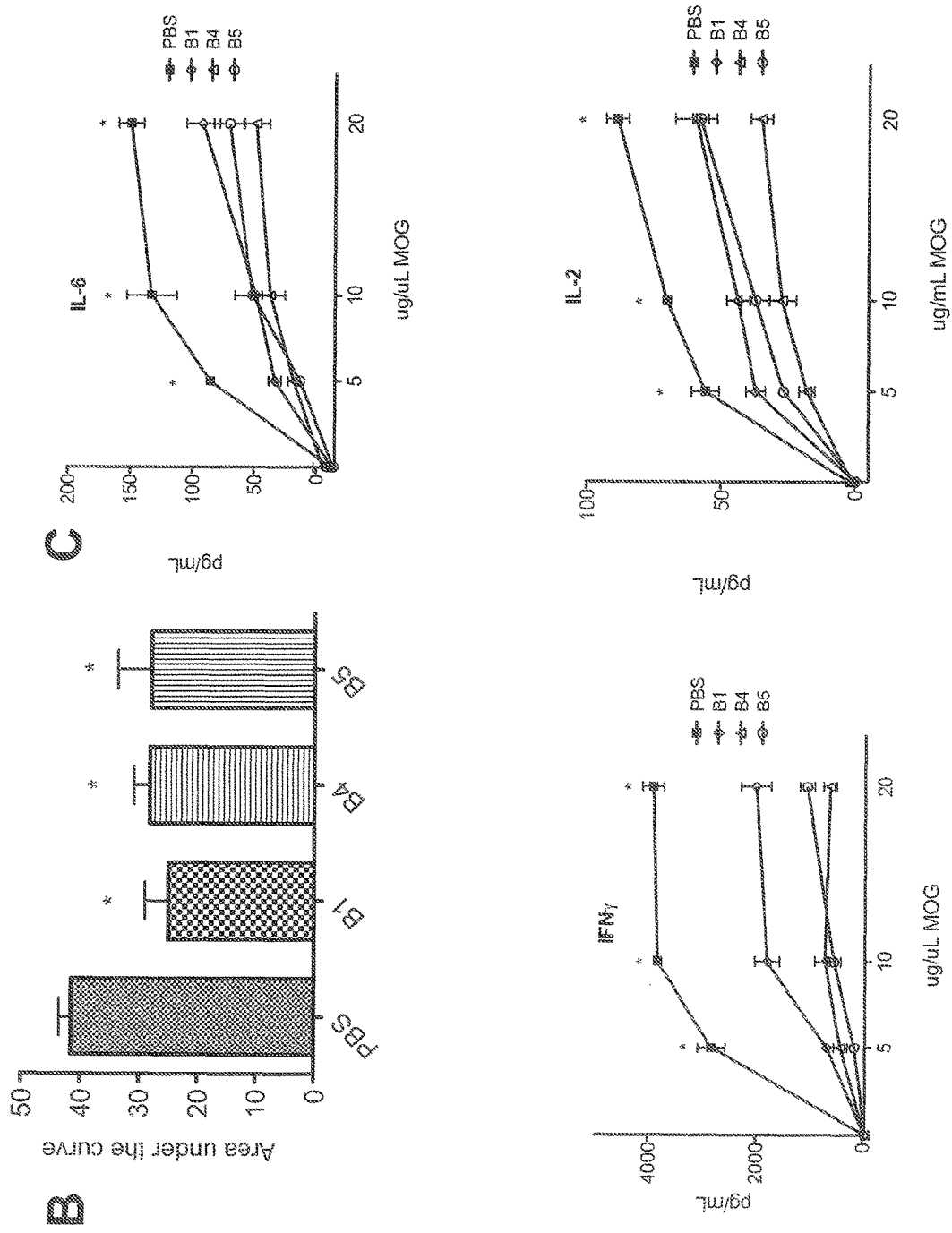
Figure 1B-C

SMALL HEAT SHOCK PROTEINS AND ACTIVE FRAGMENTS THEREOF AS A THERAPY FOR INFLAMMATION AND ISCHEMIA

BACKGROUND OF THE INVENTION

Small heat shock proteins are defined as having molecular weights between 12 and 43 kDa, distinguishing them in size from large heat shock proteins. There are ten human small heat shock proteins: HSPB1-HSPB10. They share common structural characteristics, including a highly conserved 90 amino acid long HSP20 domain and the capacity to form large dynamic oligomers. sHSPs also have the shared function of being intracellular molecular chaperones. As chaperone proteins, sHSPs bind misfolded proteins and prevent them from aggregating. However, they are unable to actively re-fold the protein themselves due to their lack of ATPase activity. Instead, sHSPs sequester the misfolded proteins within the cell to prevent aggregation until a large heat shock protein can assist in refolding.

Although sHSPs share both common structural and functional characteristics, they differ in tissue distribution and expression patterns. HSPB1, HSPB5, HSPB6, HSPB7, and HSPB8 are ubiquitously expressed, and are therefore constitutively present in the brain at low levels. HSPB4 is expressed solely in the lens of the eye, composing nearly 50% of the protein mass in the human lens. HSPB2 and HSPB3 are expressed in muscle and heart and may be selectively expressed in the brain. HSPB9 and HSPB10 are strictly expressed in the testes. HSPB1, HSPB5, and HSPB8 are induced in response to challenges such as heat, glucocorticoids, prostaglandins, and interferon-gamma.

Naturally occurring mutations in conserved regions in several human sHSPs have led to functional consequences including myopathies, cataracts, and Charcot Marie Tooth disease. The crystal structures for several sHSPs have been identified and greater insight has been made into the importance of sHSPs in the regulation of intracellular proteins. However, mounting evidence over the past two decades suggests that sHSPs may not only play a role in maintaining a healthy body, but that they also have protective functions in disease or injury to the central nervous system (CNS).

An upregulation of small heat shock proteins has been seen in many neurodegenerative and neuroinflammatory diseases in both human and rodent brain tissue. sHSPs are upregulated in most protein aggregation diseases of the CNS, and are upregulated in certain neurological diseases that lack classical protein aggregation such as multiple sclerosis and stroke.

Initial reports focusing on one of the small heat shock proteins, alpha B crystallin (HSPB5), suggested that this molecule might be a pathogenic autoantigen, but subsequent studies demonstrated that HSPB5 can be protective in neurological diseases with an inflammatory component. Exogenous administration of cryab can ameliorate the primary mouse model of multiple sclerosis, experimental autoimmune encephalomyelitis (EAE), making it a therapeutic to treat MS.

A further elucidation of the role of the HSPB family in inflammation and disease is of great interest.

Fragments of small heat shock proteins are described, inter alia, by Ghosh et al., US20080227700A1, US20080280824A1 and US20070185028A1; Ghosh et al. (2005) *Biochemistry* 44:14854-14869, "Interactive Domains for Chaperone Activity in the Small Heat Shock Protein, Human αB Crystallin"; Ghosh et al. (2006) *Cell Stress Chaperones* 11:187-197, "The function of the β3 interactive domain in the small heat shock protein and molecular chaperone, human αB crystallin"; Bhattacharyya et al. (2006) *Biochemistry* 45:3069-3076, "Mini-αB-Crystallin: A Functional Element of αB-Crystallin with Chaperone-like Activity"; Wieske et al. (2001) *Eur. J. Biochem.* 268:2083-2090, "Defined sequence segments of the small heat shock proteins HSP25 and αB-crystallin inhibit actin polymerization"; Santhoshkumar et al. (2006) *Protein Science* 15:2488-2498, "Conserved F84 and P86 residues in αB-crystallin are essential to effectively prevent the aggregation of substrate proteins"

Large heat shock proteins are discussed, for example, in Anderton et al. EP751957B1, "Peptide Fragments Of Microbial Stress Proteins and Pharmaceutical Composition Made Thereof for the Treatment And Prevention of Inflammatory Diseases"; Henning et al. US20080161258A1, "Hsp and Supraventricular Arrhythmia"; Gelf and et al. US20070179087A1, "Method for Treating Inflammatory Diseases using Heat Shock Proteins"; Dillmann et al. US20040132190A1, "Gene Therapy for Myocardial Ischemia".

References of interest also include Sanbe A et al. (2007) JOURNAL OF BIOLOGICAL CHEMISTRY 82:555-563, "Interruption of CryAB-Amyloid Oligomer Formation by HSP22"; Ye et al. (2011) *Med Hypotheses* 76:296-298, "Locally synthesized HSP27 in hepatocytes: Is it possibly a novel strategy against human liver ischemia/reperfusion injury?"; Lee et al. (2009) *J Control Release* 137:196-202, "Controlled delivery of heat shock protein using an injectable microsphere/hydrogel combination system for the treatment of myocardial infarction"; Badin et al. (2009) *J Cereb Blood Flow Metab* 29:254-263, "Protective effect of post-ischaemic viral delivery of heat shock proteins in vivo"; An et al. (2008) *FEBS J.* 275:1296-1308, "Transduced human PEP-1-heat shock protein 27 efficiently protects against brain ischemic insult"; Kwon et al. (2007) *Biochem Biophys Res Commun* 363:399-404, "Protective effect of heat shock protein 27 using protein transduction domain-mediated delivery on ischemia/reperfusion heart injury"; Brundel et al. (2006) *Circ Res* 99:1394-402 "Induction of heat shock response protects the heart against atrial fibrillation"; Badin et al. (2006) *J Cereb Blood Flow Metab* 26:371-381, "Neuroprotective effects of virally delivered HSPs in experimental stroke"; Martin et al. (1997) CIRCULATION 96:4343-4348, "Small heat shock proteins and protection against ischemic injury in cardiac myocytes"; Islamovic E et al. (2007) *J Mol Cell Cardiol* 42:862-869 "Importance of small heat shock protein 20 (hsp20) C-terminal extension in cardioprotection"; Sharma et al. (2000) *J Biol Chem* 275:3767-3771, "Synthesis and Characterization of a Peptide Identified as a Functional Element in αA-crystallin"; and Ghosh et al. (2008) *The International Journal of Biochemistry & Cell Biology* 40:954-967, "Interactive sequences in the molecular chaperone, human αB crystallin modulate the fibrillation of amyloidogenic proteins";

SUMMARY OF THE INVENTION

Composition and methods are provided for the treatment of inflammatory or ischemic disease. In the methods of the invention, an agent providing small heat shock protein activity is administered to a patient, where the dose is effective to suppress or prevent initiation, progression, or relapses of disease, usually prevention of the progression of disease or sequelae following an acute incident. The administration may be systemic, including intravenous, intramuscular, intra-peritoneal, sub-cutaneous, etc., and usually other than oral administration.

Inflammatory diseases of interest include neurological inflammatory diseases, which may be demyelinating autoimmune diseases, such as multiple sclerbsis (MS), neuromyelitis optica (NO) EAE, chronic inflammatory demyelinating polyneuropathy, and the like. In other embodiments, inflammatory diseases include, without limitation, rheumatoid arthritis, atherosclerosis, stroke, myocardial infarction and peripheral arterial vascular disease, Alzheimer's disease, Parkinson's disease and amyotrophic lateral sclerosis, also known as Lou Gehrig's disease. In the treatment of stroke, the agent may be administered with about 12 hours following the ischemic event, within about 10 hours of the ischemic event, within about 8 hours of the ischemic event, within about 6 hours of the ischemic event. The methods of the invention provide an advantage in being active when administered from between 8 to 12, or from between about 10 to 12 hours after the ischemic event.

In some embodiments of the invention, the agent providing small heat shock protein activity is a human small heat shock protein or active fragment thereof, including peptides which comprise or consist of at least about 15 amino acids, at least about 18 amino acids, including peptides of 20 amino acids, and not more than about 25 amino acids, not more than about 22 amino acids, where the amino acid sequence is usually a contiguous stretch of amino acids in a human HSPB protein; which protein may be selected from the group consisting of HSPB1, HSPB2, HSPB3, HSPB4, HSPB5, HSPB6, HSPB7, HSPB8, HSPB9, HSPB10. In some embodiments the protein is selected from the group consisting of HSPB1, HSPB4, HSPB5. In some embodiments the protein is a human small heat shock protein other than HSPB5. Peptides of interest include peptides having molecular chaperone activity.

Where the agent is a peptide, the peptide may consist or consist essentially of a peptide having an amino acid sequence corresponding to amino acid residues 11-25, 71-85, 131-145, 73-92 or 161-175 of HSPB5, for example any one of HSPB1, HSPB2, HSPB3, HSPB4, HSPB5, HSPB6, HSPB7, HSPB8, HSPB9, HSPB10 as shown in the alignment of FIG. 17.

Compositions for use in the methods of the invention include a protein or peptide providing small heat shock protein activity, e.g. providing molecular chaperone activity, in a pharmaceutically acceptable excipient, including an excipient suitable for systemic injection.

In some embodiments, the active agent is a nucleic acid that specifically enhances levels of small heat shock protein activity, e.g. by providing a nucleic acid that encodes small heat shock protein or peptide operably linked to a promoter.

In some methods of the invention, the subject is a human. In some methods, the level of small heat shock protein activity is monitored in a cell of the patient selected from the group consisting of a T cell, a neuron, a macrophage, a vascular endothelial cell, an astrocyte and a microglial cell during therapy. In some methods, the patient has ongoing inflammatory disease and the method further comprises monitoring a decrease in the symptoms of the patient responsive to the administering of small heat shock protein activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1A:
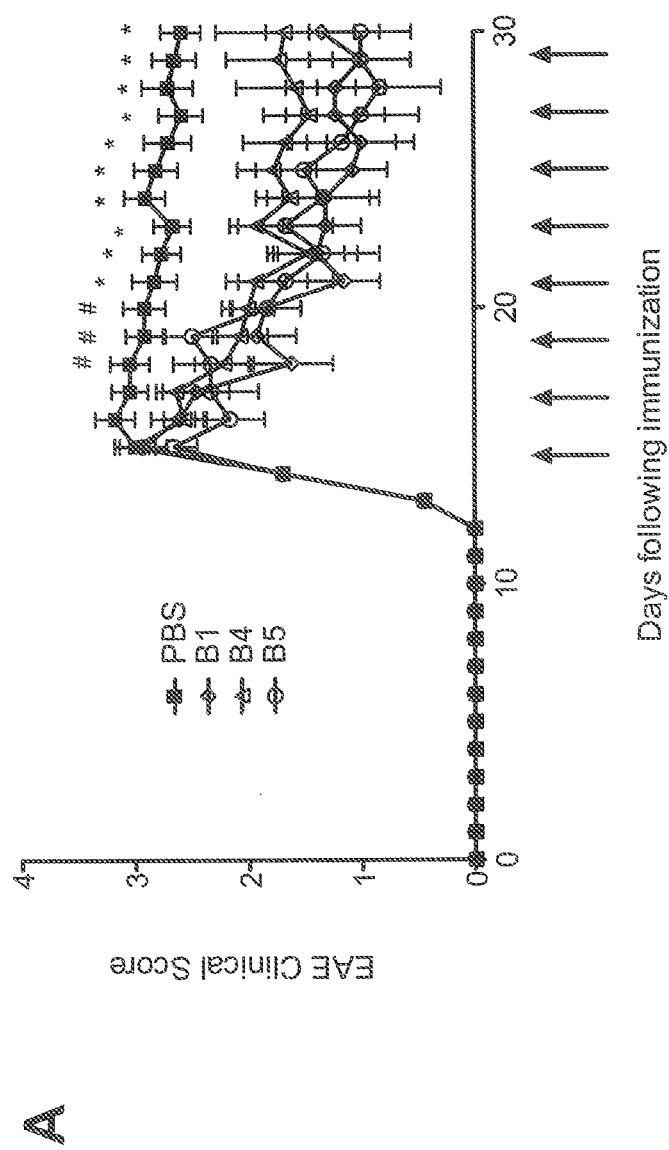
FIG. 1. HSPB1, HSPB4, and HSPB5 are therapeutic in EAE. a) 129Sv WT mice were immunized with MOG35-55/CFA and treated with either HSPB1, HSPB4, HSPB5 or PBS beginning at the peak of disease (n>10 mice per group, *p<0.05). b) Area under the curve was calculated for each mouse in each group and means were compared (*p<0.05). c) sHSPs suppressed splenocyte production of pro-inflammatory cytokine measured by cytokine specific ELISAs (*p<0.05).

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

"Activity" of small heat shock protein activity shall mean any enzymatic or binding function performed by that protein, usually molecular chaperone activity as described below, which may be measured as an ability to prevent aggregation of partially denatured proteins.

"Comparable cell" shall mean a cell whose type is identical to that of another cell to which it is compared. Examples of comparable cells are cells from the same cell line.

"Expressible nucleic acid" shall mean a nucleic acid encoding a nucleic acid of interest and/or a protein of interest, which nucleic acid is an expression vector, plasmid or other construct which, when placed in a cell, permits the expression of the nucleic acid or protein of interest. Expression vectors and plasmids are well known in the art.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may refer to a relapse in a patient that has ongoing relapsing remitting disease. The methods of the invention are specifically applied to patients that have been diagnosed with an autoimmune disease. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR System's, Reagents and Consumables (Perkin Elmer Catalogue 1996-1997, Roche Molecular Systems, Inc., Branchburg, N.J., USA).

Small heat shock proteins (sHsp) protect a variety of cells from heat and other forms of stress, such as hypoxia/ischemia, oxidative stress, or exposure to heavy metals in a wide range of different cell types. Members of the super-family are diverse in sequence and size, but are characterized by (i.) their conserved 90 amino acid hsp20 domain, (ii.) their small molecular weight between 12 and 43 kDa, (iii.) their capacity to form large oligomers, (iv.) their capacity to exhibit dynamic quarternary structure and (v.) and their ability to minimize protein aggregation when induced under conditions of stress via their chaperone activity. There are ten sHsps expressed in humans HspB1 (HSP27), HspB2 (myotonic dystrophy protein kinase binding protein, MKBP), HspB3, HspB4 (αA-crystallin), HspB5 (αB-crystallin), HspB6 (Hsp22), HSPB8 (Hsp20), HSPB9, and HSPB10 (sperm outer dense fiber protein, ODFP).

Figure 17:
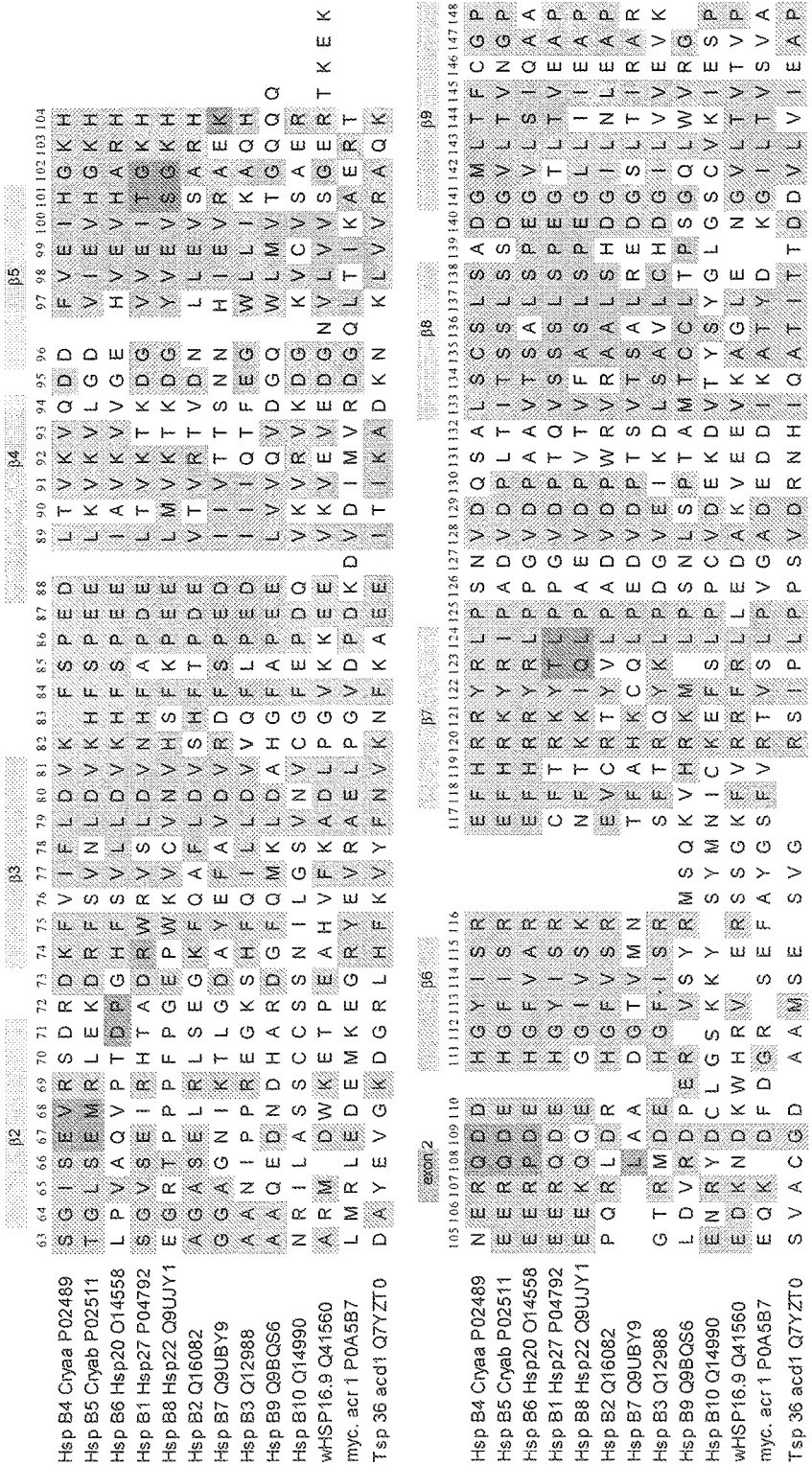
FIG. 17. Alignment of small heat shock protein sequences. Top to bottom, SEQ ID NOs: 25-37.

Small Hsps aggregate to form large oligomeric structures. They bind partially unfolded proteins through hydrophobic interactions, independent of ATP, and prevent and/or reverse protein aggregation. The ability of this family of proteins to act as chaperones increases with temperature. The rate of dissociation of the monomers from the aggregate also increases with temperature, and the hydrophobic sites involved in aggregation overlap with the sites that unfolded ligands bind. The sequences and Genbank accession numbers of the 10 human HSPB proteins is provided in FIG. 17.

In some embodiments an active fragment providing small heat shock protein activity consists, or consists essentially of a peptide of amino acid residues 73-92 (relative to HspB5), for example (SEQ ID NO:1) DKFVIFLDVKHF-SPEDLTVK (B4); (SEQ ID NO:2) DRFSVNLDVKHF-SPEELKVK (B5); (SEQ ID NO:3) DRWRVSLDVNHFAP-DELTVK (B1); (SEQ ID NO:4) GHFSVLLDVKHFSPEEIAVK (B6); (SEQ ID NO:5) EPWKVCVNVHSFKPEELMVK B8; (SEQ ID NO:6) GKFQAFLDVSHFTPDEVTVR (B2); (SEQ ID NO:7) DAYEFAVDVRDFSPEDIIVT (B7); (SEQ ID NO:8) SHFQILLDVVQFLQEDIIIQ (B3); (SEQ ID NO:9) DGFQMKLDAHGFAPEELVVQ (B9); (SEQ ID NO:10) SNILGSVNVCGFEPDQVKVR (B10); (SEQ ID NO:11) EAHVFKADLPGVKKEEVKVE (P16); (SEQ ID NO:12) GRYEVRAELPGVDPDKDVDIM (ACR1); (SEQ ID NO:13) LHFKVYFNVKNFKAEEITIK (ACD1).

Over-expression of small heat shock protein activity means an expression level that is greater than the mean plus one standard deviation of that in a population of normal individuals. Preferably the expression level is at least ten times the mean of that in a population of normal individuals.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression (a) more than the expression of any other protein, or (b) more than the expression of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen.

When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular (mediated by antigen-specific T cells or their secretion products) response, which may include a component that is directed against small heat shock protein activity. An "immunogen" is capable of inducing an immunological response against itself on administration to a mammal or due to autoimmune disease.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of pre-existing conditions. For example, the prevention of autoimmune disease may be accomplished by administration of the agent prior to development of a relapse. The treatment of ongoing disease, where the treatment stabilizes or improves the clinical symptoms of the patient, is of particular interest.

The invention provides methods for treating inflammatory diseases. Inflammatory diseases of interest include neurological inflammatory conditions, e.g. Alzheimer's Disease, Parkinson's Disease, Lou Gehrig's Disease, etc. and demyelinating diseases, such as multiple sclerosis, chronic inflammatory demyelinating polyneuropathy, etc. as well as inflammatory conditions such as rheumatoid arthritis. The methods of the invention comprise administering to the subject an effective amount of an agent that provides small heat shock protein activity activity, to suppress or prevent initiation, progression, or relapses of disease.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The delivery systems described herein, which employ a number of routinely used pharmaceutical carriers, are only representative of the many embodiments envisioned for administering the instant compositions.

Conditions for Analysis and Therapy

The compositions and methods of the invention find use in combination with a variety of inflammatory conditions, including neurological inflammatory conditions, relapsing autoimmune conditions, and relapsing neurological inflammatory conditions.

Inflammatory Disease.

Inflammation is a process whereby the immune system responds to infection or tissue damage. Inflammatory disease results from an activation of the immune system that causes illness, in the absence of infection or tissue damage, or at a response level that causes illness. Inflammatory disease includes autoimmune disease, which are any disease caused by immunity that becomes misdirected at healthy cells and/or tissues of the body. Autoimmune diseases are characterized by T and B lymphocytes that aberrantly target self-proteins, -polypeptides, -peptides, and/or other self-molecules causing injury and or malfunction of an organ, tissue, or cell-type within the body (for example, pancreas, brain, thyroid or gastrointestinal tract) to cause the clinical manifestations of the disease. Autoimmune diseases include diseases that affect specific tissues as well as diseases that can affect multiple tissues, which can depend, in part on whether the responses are directed to an antigen confined to a particular tissue or to an antigen that is widely distributed in the body.

The immune system employs a highly complex mechanism designed to generate responses to protect mammals against a variety of foreign pathogens while at the same time preventing responses against self-antigens. In addition to deciding whether to respond (antigen specificity), the immune system must also choose appropriate effector functions to deal with each pathogen (effector specificity).

Atherosclerosis is an inflammatory disease in which interferon (IFN)-γ, the signature cytokine of Th1 cells, plays a central role. Interleukin (IL)-17, the signature cytokine of Th17 cells, is also associated with human coronary atherosclerosis. IL-17 is produced concomitantly with IFN-γ by coronary artery-infiltrating T cells and that these cytokines act synergistically to induce proinflammatory responses in vascular smooth muscle cells. (see Eid et al. Circulation. 2009; 119:1424-1432.)

Inflammatory Demyelinating Disease.

The term "inflammatory" response is the development of a humoral (antibody mediated) and/or a cellular (mediated by antigen-specific T cells or their secretion products) response. Inflammatory demyelinating diseases of the central nervous system are of particular interest and include, without limitation, multiple sclerosis (MS), neuromyelitis optica (NO), and experimental acquired encephalitis (EAE). Demyelinating inflammatory diseases of the peripheral nervous system include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy.

Multiple sclerosis is characterized by various symptoms and signs of CNS dysfunction, with remissions and recurring exacerbations. Classifications of interest for analysis by the methods of the invention include relapsing remitting MS (RRMS), primary progressive MS (PPMS) and secondary progressive MS (SPMS). The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat can accentuate symptoms and signs.

The course is highly varied, unpredictable, and, in most patients, remittent. At first, months or years of remission can separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RR MS) is characterized clinically by relapses and remissions that occur over months to years, with partial or full recovery of neurological deficits between attacks. Such patients manifest approximately 1 attack, or relapse, per year. Over 10 to 20 years, approximately 50% of RR MS patients develop secondary progressive MS (SP MS) which is characterized by incomplete recovery between attacks and accumulation of neurologic deficits resulting in increasing disability.

Secondary Progressive Multiple Sclerosis (SPMS) (see Kappos et al. (2004) Neurology 63(10):1779-87) in a study with interferon beta-1b (IFNB-1b) in secondary progressive multiple sclerosis (SPMS) showed divergent results with regard to their primary outcome of sustained Expanded Disability Status Scale (EDSS) progression. Certain patients were found to benefit from the treatment, where pronounced disability progression and continuing relapse activity might help in identifying those patients in the secondary progressive phase of the disease who are more likely to benefit from treatment.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

MRI, the most sensitive diagnostic imaging technique, can show plaques. It can also detect treatable nondemyelinating lesions at the junction of the spinal cord and medulla (e.g., subarachnoid cyst, foramen magnum tumors) that occasionally cause a variable and fluctuating spectrum of motor and sensory symptoms, mimicking MS. Gadolinium-contrast enhancement can distinguish areas of active inflammation from older brain plaques. MS lesions can also be visible on contrast-enhanced CT scans; sensitivity can be increased by giving twice the iodine dose and delaying scanning (double-dose delayed CT scan).

Conventional treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFN gamma antibody, CTLA4-Ig (Abetacept), anti-CD20 (Rituxan), and other anti-cytokine agents are in clinical development for MS.

Peripheral neuropathies include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

Neuromyelitis optica (NMO), or Devic's disease, is an autoimmune, inflammatory disorder of the optic nerves and spinal cord. Although inflammation can affect the brain, the disorder is distinct from multiple sclerosis, having a different pattern of response to therapy, possibly a different pattern of autoantigens and involvement of different lymphocyte subsets.

The main symptoms of Devic's disease are loss of vision and spinal cord function. As for other etiologies of optic neuritis, the visual impairment usually manifests as decreased visual acuity, although visual field defects, or loss of color vision can occur in isolation or prior to formal loss of acuity. Spinal cord dysfunction can lead to muscle weakness, reduced sensation, or loss of bladder and bowel control. The damage in the spinal cord can range from inflammatory demyelination to necrotic damage of the white and grey matter. The inflammatory lesions in Devic's disease have been classified as type II lesions (complement mediated demyelinization), but they differ from MS pattern II lesions in their prominent perivascular distribution. Therefore, the pattern of inflammation is often quite distinct from that seen in MS.

Attacks are treated with short courses of high dosage intravenous corticosteroids such as methylprednisolone IV. When attacks progress or do not respond to corticosteroid treatment, plasmapheresis can be used. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. The monoclonal antibody rituximab is under study.

The disease can be monophasic, i.e. a single episode with permanent remission. However, at least 85% of patients have a relapsing form of the disease with repeated attacks of transverse myelitis and/or optic neuritis. In patients with the monophasic form the transverse myelitis and optic neuritis occur simultaneously or within days of each other. On the other hand, patients with the relapsing form are more likely to have weeks or months between the initial attacks and to have better motor recovery after the initial transverse myelitis event. Relapses usually occur early with about 55% of patients having a relapse in the first year and 90% in the first 5 years. Unlike MS, Devic's disease rarely has a secondary progressive phase in which patients have increasing neurologic decline between attacks without remission. Instead, disabilities arise from the acute attacks.

The term "stroke" broadly refers to the development of neurological deficits associated with impaired blood flow to the brain regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardic arrest, cardiogenic shock, septic shock, head trauma, spinal cord trauma, seizure, bleeding from a tumor, or other blood loss. By "ischemic episode" is meant any circumstance that results in a deficient supply of blood to a tissue. When the ischemia is associated with a stroke, it can be either global or focal ischemia, as defined below. The term "ischemic stroke" refers more specifically to a type of stroke that is of limited extent and caused due to blockage of blood flow. Cerebral ischemic episodes result from a deficiency in the blood supply to the brain. The spinal cord, which is also a part of the central nervous system, is equally susceptible to ischemia resulting from diminished blood flow.

By "focal ischemia," as used herein in reference to the central nervous system, is meant the condition that results from the blockage of a single artery that supplies blood to the brain or spinal cord, resulting in damage to the cells in the territory supplied by that artery.

By "global ischemia," as used herein in reference to the central nervous system, is meant the condition that results from a general diminution of blood flow to the entire brain, forebrain, or spinal cord, which causes the death of neurons in selectively vulnerable regions throughout these tissues. The pathology in each of these cases is quite different, as are the clinical correlates.

Parkinson's disease is an idiopathic, slowly progressive, degenerative CNS disorder characterized by slow and decreased movement, muscular rigidity, resting tremor, and postural instability. Diagnosis is clinical. Treatment is with levodopa plus carbidopa, other drugs, and, for refractory symptoms, surgery. In Parkinson's disease, pigmented neurons of the substantia nigra, locus ceruleus, and other brain stem dopaminergic cell groups are lost. Loss of substantia nigra neurons, which project into the caudate nucleus and putamen, depletes dopamine in these areas.

The presence of complement proteins, including all components of the membrane attack complex, has been shown intracellularly on Lewy bodies and on oligodendroglia in the substantia nigra in PD and familial PD. Such oligodendroglia have been described as complement activated oligodendroglia.

A profusion of reactive microglia is seen in the substantia nigra and striatum, not only in idiopathic PD, but also in familial PD, as well as in the parkinsonism-dementia complex of Guam. Reactive microglia are also seen in the basal ganglia in 6-hydroxydopamine and MPTP animal models of PD, and there are several reports that anti-inflammatories inhibit dopaminergic neurotoxicity in such animal models. Microglia can be activated by products of the classical complement cascade, by various inflammatory cytokines, and by chromogranin A, which has been reported to occur in PD substantia nigra.

Increased levels of interleukin-1$\beta$, interleukin-6, and TNF$\alpha$ have been found in the basal ganglia and CSF of PD patients. The presence of glial cells immunoreactive for TNF$\alpha$ and/or interleukin-1$\beta$ has also been reported in the substantia nigra of PD patients.

Alzheimer's disease causes progressive cognitive deterioration and is characterized by senile plaques, $\beta$-amyloid deposits, and neurofibrillary tangles in the cerebral cortex and subcortical gray matter. Most cases are sporadic, with late onset (>60 yr) and unclear etiology. However, about 5 to 15% are familial; ½ of these cases have an early onset (<60 yr) and are typically related to specific genetic mutations. Typically, extracellular $\beta$-amyloid deposits, intracellular neurofibrillary tangles (paired helical filaments), and senile plaques develop, and neurons are lost. Cerebrocortical atrophy is common, and use of cerebral glucose is reduced, as is perfusion in the parietal lobe, temporal cortices, and prefrontal cortex.

One of the characteristic pathological features of Alzheimer disease (AD) is a robust inflammatory response associated with extracellular deposition of amyloid $\beta$-protein (A$\beta$). Microglia are the predominant immune cells in the brain that participate in the inflammatory response in AD. Activation of microglia may contribute to the neurodegenerative process by the elaboration of proinflammatory cytokines, such as interleukin-1$\beta$, IL-6 and tumor necrosis factor-$\alpha$, as well as other neurotoxic factors. Epidemiological studies indicate that there might be a reduced risk of AD in patients who have been treated with non-steroidal anti-inflammatory drugs, suggesting that inflammation may contribute to disease progression.

Amyotrophic lateral sclerosis (ALS): ALS (Lou Gehrig disease, Charcot's syndrome) is the most common motor neuron disease. Patients present with random, asymmetric symptoms, consisting of cramps, weakness, and muscle atrophy of the hands (most commonly) or feet. Fasciculations, spasticity, hyperactive deep tendon reflexes, extensor plantar reflexes, clumsiness, stiffness of movement, weight loss, fatigue, and difficulty controlling facial expression and tongue movements soon follow. Other symptoms include hoarseness, dysphagia, slurred speech, and a tendency to choke on liquids. Late in the disorder, inappropriate, involuntary, and uncontrollable excesses of laughter or crying (pseudobulbar affect) occur. Death is usually caused by failure of the respiratory muscles.

Experimental evidence supports a model for ALS neurodegeneration in which nonneuronal cells such as microglia contribute to the demise of motor neurons. Over the course of the disease, spinal cord microglial cells may become activated and acquire the capacity of oxidatively damaging nearby macromolecules and cells homed within inflamed ALS tissues. Evidence of microgliosis, NADPH oxidase up-regulation, and protein carbonylation has also been found in postmortem spinal cords from human sporadic ALS cases, supporting the conclusion that the occurrence of inflammation-mediated oxidative damage is also a pathological hallmark of the prevalent nonfamilial, sporadic form of ALS.

Rheumatoid Arthritis is a chronic syndrome characterized by usually symmetric inflammation of the peripheral joints, potentially resulting in progressive destruction of articular and periarticular structures, with or without generalized manifestations. The cause is unknown. A genetic predisposition has been identified and, in white populations, localized to a pentapeptide in the HLA-DR beta1 locus of class II histocompatibility genes. Environmental factors may also play a role. Immunologic changes may be initiated by multiple factors. About 0.6% of all populations are affected, women two to three times more often than men. Onset may be at any age, most often between 25 and 50 yr.

Prominent immunologic abnormalities that may be important in pathogenesis include immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

In chronically affected joints, the normally delicate synovium develops many villous folds and thickens because of increased numbers and size of synovial lining cells and colonization by lymphocytes and plasma cells. The lining cells produce various materials, including collagenase and stromelysin, which can contribute to cartilage destruction; interleukin-1, which stimulates lymphocyte proliferation; and prostaglandins. The infiltrating cells, initially perivenular but later forming lymphoid follicles with germinal centers, synthesize interleukin-2, other cytokines, RF, and other immunoglobulins. Fibrin deposition, fibrosis, and necrosis also are present. Hyperplastic synovial tissue (pannus) may erode cartilage, subchondral bone, articular capsule, and ligaments. PMNs are not prominent in the synovium but often predominate in the synovial fluid.

Onset is usually insidious, with progressive joint involvement, but may be abrupt, with simultaneous inflammation in multiple joints. Tenderness in nearly all inflamed joints is the most sensitive physical finding. Synovial thickening, the most specific physical finding, eventually occurs in most involved joints. Symmetric involvement of small hand joints (especially proximal interphalangeal and metacarpophalangeal), foot joints (metatarsophalangeal), wrists, elbows, and ankles is typical, but initial manifestations may occur in any joint.

Atherosclerosis.

Atherosclerotic plaque consists of accumulated intracellular and extracellular lipids, smooth muscle cells, connective tissue, and glycosaminoglycans. Macrophages are integral to the development of atherosclerosis. The modified or oxidized LDL is chemotactic to monocytes, promoting their migration into the intima, their early appearance in the fatty streak, and their transformation and retention in the subintimal compartment as macrophages. Scavenger receptors on the surface of macrophages facilitate the entry of oxidized LDL into these cells, transferring them into lipid-laden macrophages and foam cells. Oxidized LDL is also cytotoxic to endothelial cells and may be responsible for their dysfunction or loss from the more advanced lesion.

The chronic endothelial injury hypothesis postulates that endothelial injury by various mechanisms produces loss of endothelium, adhesion of platelets to subendothelium, aggregation of platelets, chemotaxis of monocytes and T-cell lymphocytes, and release of platelet-derived and monocyte-derived growth factors that induce migration of smooth muscle cells from the media into the intima, where they replicate, synthesize connective tissue and proteoglycans, and form a fibrous plaque. Other cells, e.g. macrophages, endothelial cells, arterial smooth muscle cells, also produce growth factors that can contribute to smooth muscle hyperplasia and extracellular matrix production.

Endothelial dysfunction includes increased endothelial permeability to lipoproteins and other plasma constituents, expression of adhesion molecules and elaboration of growth factors that lead to increased adherence of monocytes, macrophages and T lymphocytes. These cells may migrate through the endothelium and situate themselves within the subendothelial layer. Foam cells also release growth factors and cytokines that promote migration of smooth muscle cells and stimulate neointimal proliferation, continue to accumulate lipid and support endothelial cell dysfunction. Clinical and laboratory studies have shown that inflammation plays a major role in the initiation, progression and destabilization of atheromas.

Atherosclerosis is characteristically silent until critical stenosis, thrombosis, aneurysm, or embolus supervenes. Initially, symptoms and signs reflect an inability of blood flow to the affected tissue to increase with demand, e.g. angina on exertion, intermittent claudication. Symptoms and signs commonly develop gradually as the atheroma slowly encroaches on the vessel lumen. However, when a major artery is acutely occluded, the symptoms and signs may be dramatic.

Currently, due to lack of appropriate diagnostic strategies, the first clinical presentation of more than half of the patients with coronary artery disease is either myocardial infarction or death. Further progress in prevention and treatment depends on the development of strategies focused on the primary inflammatory process in the vascular wall, which is fundamental in the etiology of atherosclerotic disease.

Therapeutic Agents

In one embodiment of the invention, agents that provide small heat shock protein activity, e.g. proteins and peptides as described above, and, nucleic acids encoding the same, and the like are used in the treatment of diseases as described above.

In some embodiments of the invention, a protein or peptide of a small heat shock protein, or a functional fragment thereof is administered to a patient. Polypeptides useful in this invention also include derivatives, variants, and biologically active fragments of naturally occurring polypeptides, and the like. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

The sequence of peptides described herein may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins in a fusion protein, typically where the two proteins are not normally joined, such as the Fc of an IgG isotype, which may be complement binding, with a toxin, such as ricin, abrin, diphtheria toxin, or the like, or with specific binding agents that allow targeting to specific moieties on a target cell.

The active peptide fragment or protein may be fused to another polypeptide to provide for added functionality, e.g. to increase the in vivo stability. Generally such fusion partners are a stable plasma protein, which may, for example, extend the in vivo plasma half-life when present as a fusion, in particular wherein such a stable plasma protein is an immunoglobulin constant domain.

In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the αBC also will be produced and employed as a multimer having substantially the same structure as the stable plasma protein precursor. These multimers will be homogeneous with respect to the peptide they comprise, or they may contain more than one peptide.

Stable plasma proteins are proteins typically having about from 30 to 2,000 residues, which exhibit in their native environment an extended half-life in the circulation, i.e. greater than about 20 hours. Examples of suitable stable plasma proteins are immunoglobulins, albumin, lipoproteins, apolipoproteins and transferrin. The peptide typically is fused to the plasma protein, e.g. IgG at the N-terminus of the plasma protein or fragment thereof which is capable of conferring an extended half-life upon the peptide. Increases of greater than about 100% on the plasma half-life of the peptide are satisfactory. Ordinarily, the peptide is fused C-terminally to the N-terminus of the constant region of immunoglobulins in place of the variable region(s) thereof, however N-terminal fusions may also find use.

Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The site at which the fusion is made may be selected in order to optimize the biological activity, secretion or binding characteristics of the peptide. For some embodiments fusions will containing peptide immune epitopes that are recognized by antibodies. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basiciour chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

The peptides for use in the subject methods may be produced from eukaryotic or prokaryotic cells, or may be synthesized in vitro. Where the peptide is produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The peptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the a peptide consists essentially of a peptide sequence provided herein. By "consisting essentially of" in the context of a polypeptide described herein, it is meant that the polypeptide is composed of the provided peptide sequence, which sequence is optionally flanked by one or more amino acid or other residues that do not materially affect the basic characteristic(s) of the polypeptide.

The invention includes nucleic acids encoding peptide sequences provided herein. The nucleic acid sequences encoding the small heat shock proteins polypeptides may be accessed from public databases, as set forth in FIG. 17.

Coding sequences can be generated by methods known in the art, e.g. by in vitro synthesis, recombinant methods, etc. to provide a coding sequence. Using the known genetic code, one can produce a suitable coding sequence. Double or single stranded fragments can be obtained from the DNA sequence by chemically synthesizing oligonucleotides in accordance with conventional methods, by restriction enzyme digestion, by PCR amplification, etc.

Expression vectors may be used to introduce a coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The nucleic acid may be introduced into tissues or host cells by any number of routes, including viral infection, microinjection, or fusion of vesicles. Jet injection may also be used for intramuscular administration, as described by Furth et al. (1992) *Anal Biochem* 205:365-368. The DNA may be coated onto gold microparticles, and delivered intradermally by a particle bombardment device, or "gene gun" as described in the literature (see, for example, Tang et al. (1992) *Nature* 356:152-154), where gold microprojectiles are coated with the alpha B crystallin or DNA, then bombarded into skin cells.

The method also provide for combination therapy, where the combination may provide for additive or synergistic benefits. Combinations of an agent providing small heat shock protein activity may be combined with a second agent selected from one or more of the general classes of drugs commonly used in the non-antigen specific treatment of inflammatory disease, which include corticosteroids and disease modifying drugs; or from an antigen-specific agent. Corticosteroids have a short onset of action, but many disease modifying drugs take several weeks or months to demonstrate a clinical effect. These agents include methotrexate, leflunomide (Arava™), etanercept (Enbrel™), infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like.

Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Disease modifying anti-rheumatoid drugs, or DMARDs have been shown to alter the disease course and improve radiographic outcomes in RA. It will be understood by those of skill in the art that these drugs are also used in the treatment of other autoimmune diseases.

Methotrexate (MTX) is a frequent first-line agent because of its early onset of action (4-6 weeks), good efficacy, favorable toxicity profile, ease of administration, and low cost. MTX is the only conventional DMARD agent in which the majority of patients continue on therapy after 5 years. MTX is effective in reducing the signs and symptoms of RA, as well as slowing or halting radiographic damage. Although the immunosuppressive and cytotoxic effects of MTX are in part due to the inhibition of dihydrofolate reductase, the anti-inflammatory effects in rheumatoid arthritis appear to be related at least in part to interruption of adenosine and TNF pathways. The onset of action is 4 to 6 weeks, with 70% of patients having some response. A trial of 3 to 6 months is suggested.

Specific peptides, altered peptides, proteins or coding sequences may be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8). Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Science 263:1139).

Pharmaceutical Compositions

Active peptides or polynucleotides can serve as the active ingredient in pharmaceutical compositions formulated for the treatment of various disorders as described above. The active ingredient is present in a therapeutically effective amount, i.e., an amount sufficient when administered to treat a disease or medical condition mediated thereby. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

When the pharmaceutical composition includes a polypeptide as the active ingredient, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which are composed of the packaged active ingredient with a suppository base. Suitable suppository bases include natural or synthetic triglycerides or paraffin hydrocarbons. In addition, it is also possible to use gelatin rectal capsules, which are composed of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

Methods of Treatment

The compositions may be administered in a single dose, or in multiple doses, usually multiple doses over a period of time, e.g. daily, every-other day, weekly, semi-weekly, monthly etc. for a period of time sufficient to reduce severity of the inflammatory disease, which may comprise 1, 2, 3, 4, 6, 10, or more doses.

Determining a therapeutically or prophylactically effective amount an agent that provides small heat shock protein activity can be done based on animal data using routine computational methods. In one embodiment, the therapeutically or prophylactically effective amount contains between about 0.1 mg and about 1 g of nucleic acid or protein, as applicable. In another embodiment, the effective amount contains between about 1 mg and about 100 mg of nucleic acid or protein, as applicable. In a further embodiment, the effective amount contains between about 10 mg and about 50 mg of the nucleic acid or protein, as applicable. The effective dose will depend at least in part on the route of administration. The agents may be administered orally, in an aerosol spray; by injection, e.g. i.m., s.c., i.p., i.v., etc. In some embodiments, administration by other than i.v. may be preferred. The dose may be from about 0.1 µg/kg patient weight; about 1 µg/kg; about 10 µg/kg; to about 100 µg/kg.

The compositions are administered in a pharmaceutically acceptable excipient. The term "pharmaceutically acceptable" refers to an excipient acceptable for use in the pharmaceutical and veterinary arts, which is not toxic or otherwise inacceptable. The concentration of active agent in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Treating, treatment, or therapy of a disease or disorder shall mean slowing, stopping or reversing the disease's progression by administration of a composition of the invention. In the preferred embodiment, treating a disease means reversing the disease's progression, ideally to the point of eliminating the disease itself. As used herein, ameliorating a disease and treating a disease are equivalent. Preventing, prophylaxis or prevention of a disease or disorder as used in the context of this invention refers to the administration to prevent the occurrence or onset of a disease or disorder or some or all of the symptoms of a disease or disorder or to lessen the likelihood of the onset of a disease or disorder.

This invention will be better understood by reference to the Examples which follow, but those skilled in the art will readily appreciate that the information detailed is only illustrative of the invention as described more fully in the claims which follow thereafter.

EXPERIMENTAL

Example 1

Molecular Chaperone Dependent Therapeutic Function of Small Heat Shock Proteins in Autoimmune Demyelination Since cryab mRNA and protein levels have been shown to be upregulated in MS brains, we investigated if it was also elevated in the plasma of MS patients and EAE mice. We found that plasma levels of cryab were significantly higher in MS patients compared to normal healthy individuals and this difference was also seen in plasma samples taken from EAE mice. This suggested that endogenous cryab is not just being produced intracellularly in the brain, but that this molecule is being released into the bloodstream where it might be mediating its therapeutic effects.

Plasma levels of HSPB1 were then measured. It was found that HSPB1 plasma levels were also elevated in plasma from both MS patients and EAE mice. The protective and therapeutic function of cryab may not be specific to cryab, but rather might be a common characteristic of the family of small heat shock proteins.

HSPB1, HSPB4, and HSPB5 are all therapeutic in EAE. To investigate if the therapeutic efficacy of HSPB5 is a common feature of the whole family of small heat shock proteins, we expressed recombinant HSPB1, HSPB4, and HSPB5. We then treated EAE mice every other day starting at the peak of disease, when clinical paralysis is apparent, with an intraperitoneal (IP) administration of 10 µg of either HSPB1, HSPB4, HSPB5, or PBS as the vehicle control. We saw that all three members of the small heat shock protein family significantly ameliorated clinical paralysis and improved the clinical scores of mice with EAE (FIG. 1a). HSPB1, HSPB4, and HSPB5 all significantly improved EAE clinical scores over the course of the whole experiment (FIG. 1b). Treating mice in vivo with HSPB1, HSPB4, or HSPB5 led to a reduction in the production of pro-inflammatory cytokines by MOG stimulated splenocytes taken from MOG immunized mice (FIG. 1c). Improvement of the clinical score was dependent on continued dosing of the sHSP. After dosing was stopped, symptoms returned, and paralysis worsened after 96 hours.

Figure 2:
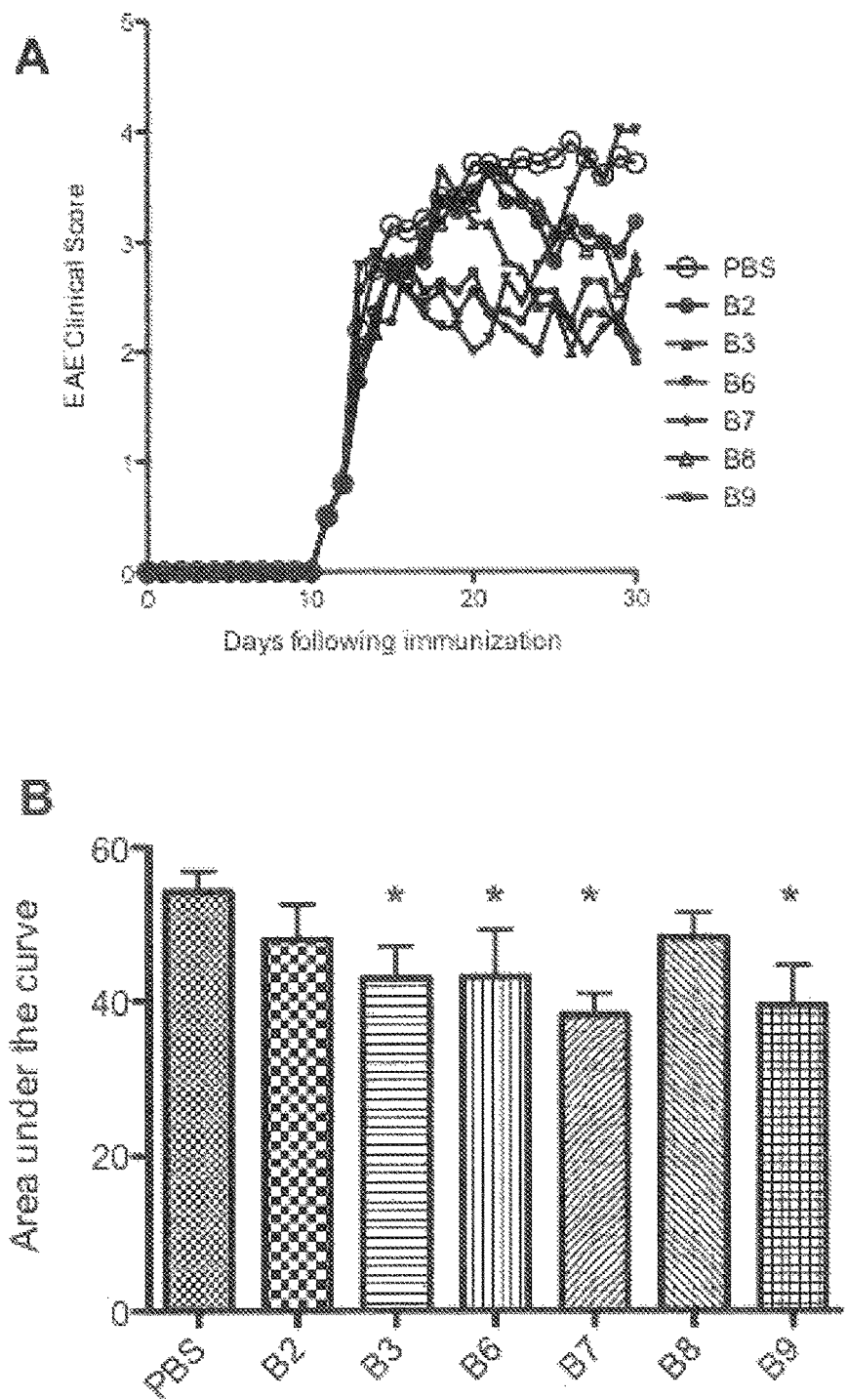
FIG. 2. The entire family of small heat shock proteins is therapeutic in EAE a) 129Sv WT mice were immunized with MOG35-55/CFA and treated beginning at the peak of disease with an intraperitoneal injection of 10 ug of each sHSP every other day. Clinical scores were taken daily. (n>10 mice per group, *p<0.05). b) Area under the curve was calculated for each mouse in each group and means were compared (*p<0.05)

To further our understanding of the whole family of small heat shock proteins, we expressed recombinant HSPB2, HSPB3, HSPB6, HSPB7, HSPB8, and HSPB9 and treated EAE mice with an intraperitoneal dose of bug every other day starting at the peak of disease. All other members of the small heat shock protein family ameliorated EAE (FIG. 2).

Figure 3A:
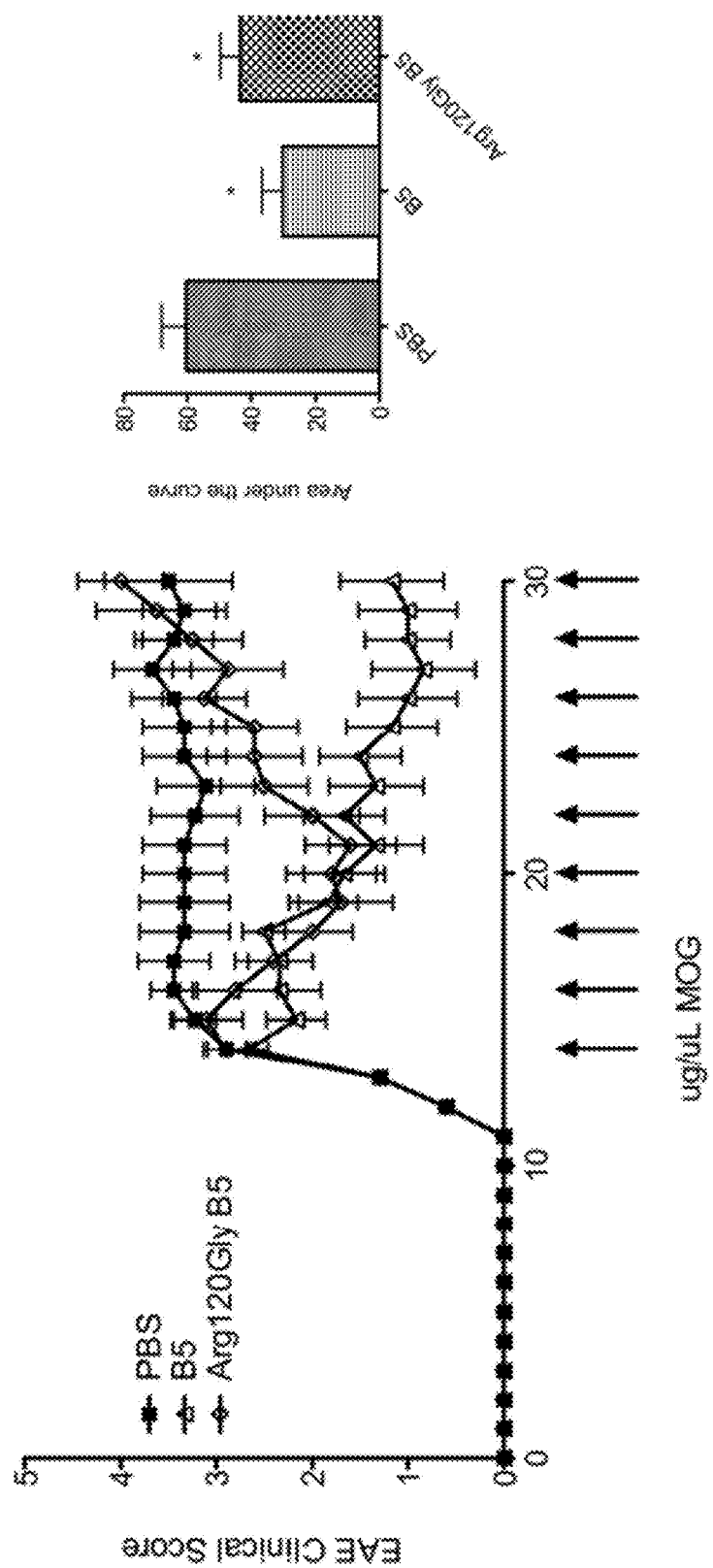
FIG. 3. Arg120Gly HSPB5 is therapeutic. a) 129Sv WT mice were immunized with MOG35-55/CFA and treated beginning at the peak of disease with an intraperitoneal injection of 10 ug of each sHSP every other day. Clinical scores were taken daily (n>10 mice per group). Area under the curve was calculated for each mouse in each group and means were compared (*p<0.05). Arg120Gly ameliorated EAE just as well as HSPB5. b) Arg120Gly suppressed pro-inflammatory cytokines in a similar way to HSPB5 (*p<0.05).
Figure 3B:
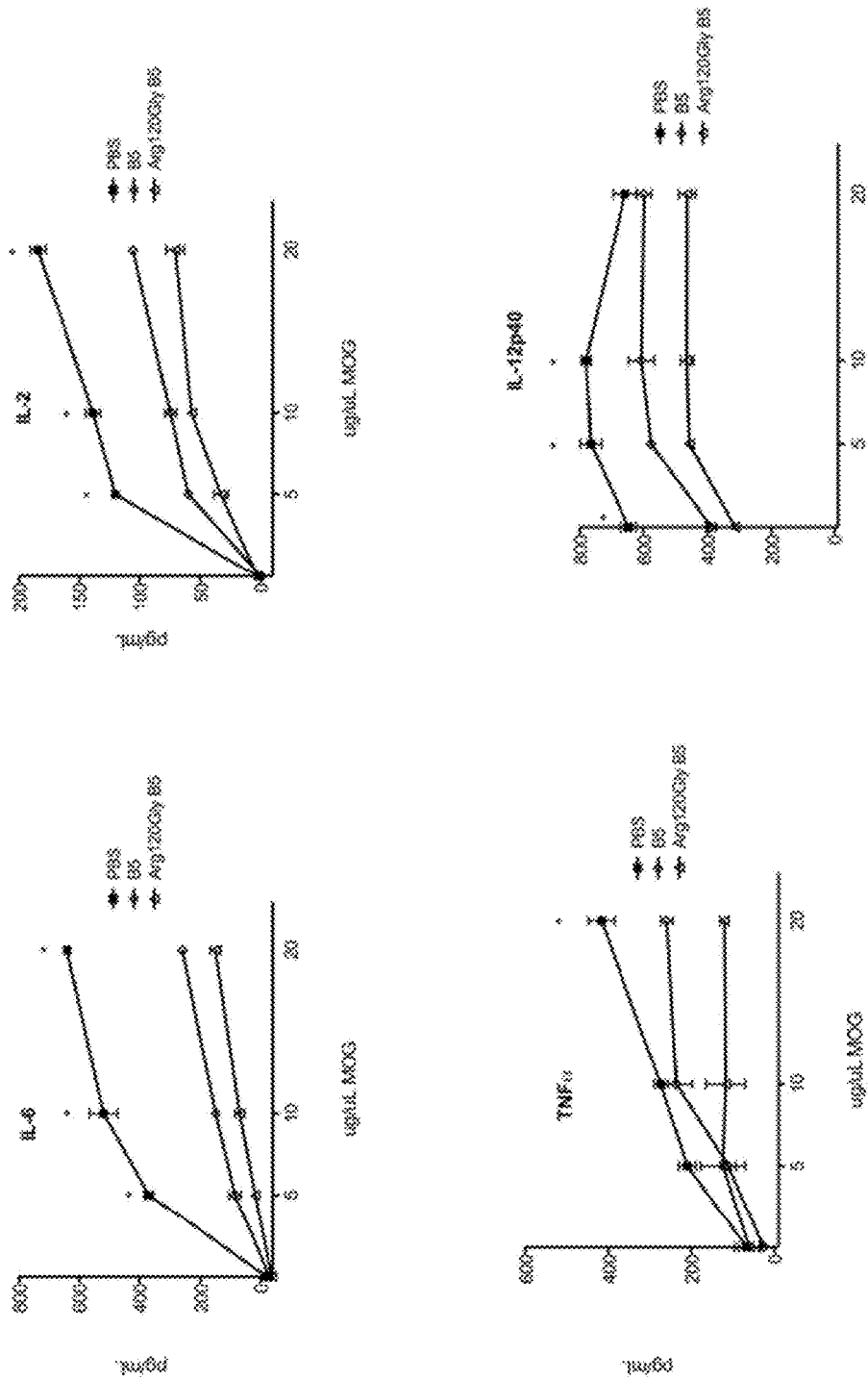

HSPB5 Mutant Arg120Gly Therapeutic for EAE. We studied a naturally occurring mutated HSPB5, Arg120Gly. This mutation of an arginine to a glycine at amino acid position 120 in HSPB5 (Arg120Gly) leads to a loss of normal protein conformation and a partial loss of molecular chaperone activity. Functionally, this naturally occurring mutation leads to a cardiomyopathy and cataract formation. Mutations in similar positions in HSPB1, HSPB4, and HSPB8 also lead to pathologies such as Charcot-Marie-Tooth disease and distal hereditary motor neuropathy. We treated mice at the peak of disease with either Arg120Gly or PBS. Interestingly, Arg120Gly did improve clinical scores despite this mutation (FIG. 3a). Additionally, it led to a decrease in peripheral immune activation with a reduction in production of pro-inflammatory cytokines in stimulated splenocytes from MOG immunized mice (FIG. 3b).

Figure 4:
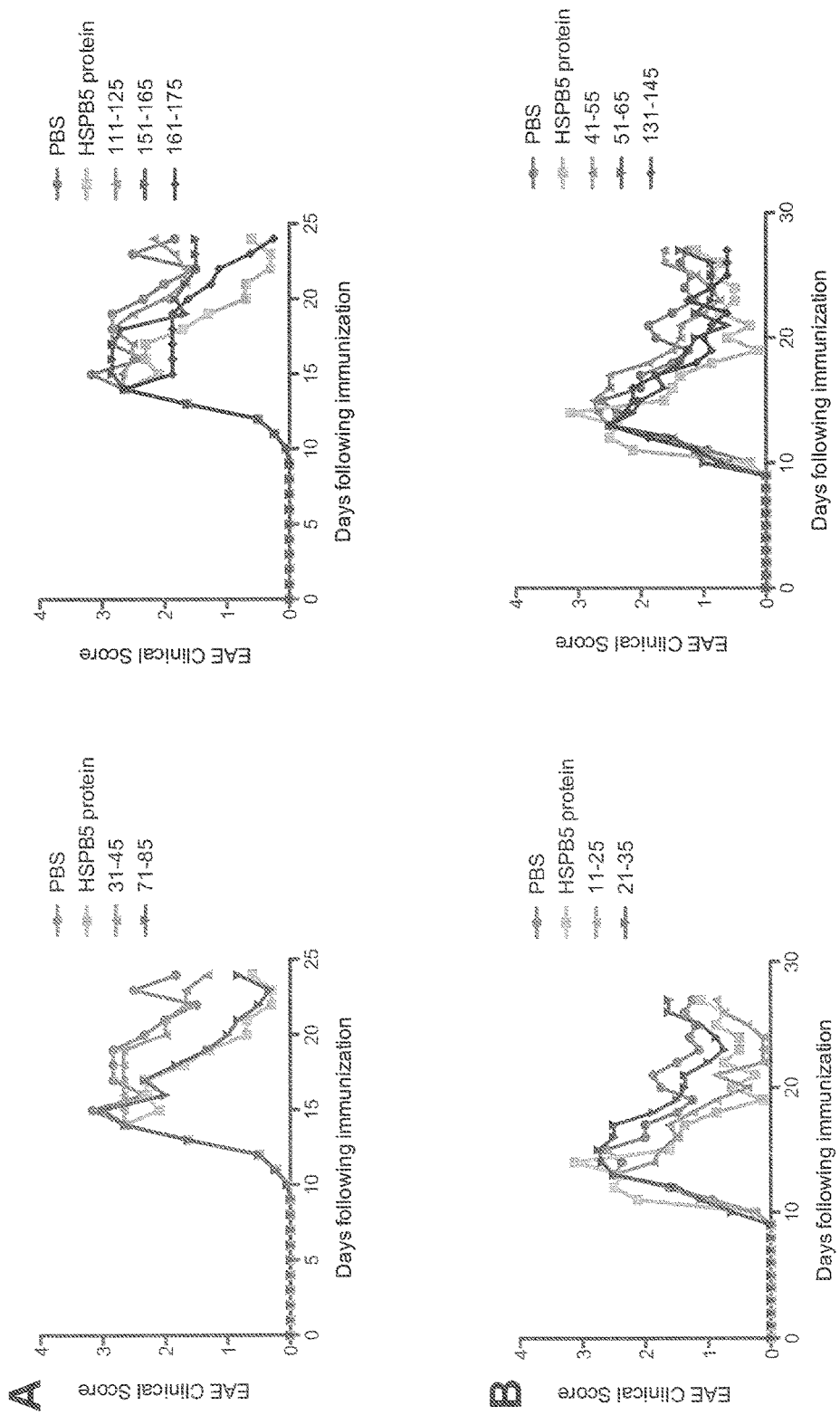
FIG. 4. HSPB5 peptide screen shows that 11-25, 71-85, 131-145, and 161-175 are therapeutic in EAE. a and b) 129Sv WT mice were immunized with MOG35-55 and CFA. Mice were treated every other day starting at the peak of the disease with bug of each peptide as a screen (n=5 mice per group, n=2 experiments total).

Therapeutic Peptides from HSPB5 in EAE. Since therapeutic efficacy in EAE was shown to be a common feature of all small heat shock proteins, we studied the domains within sHSPs that might contribute to their therapeutic efficacy. We made a series of overlapping, 15-mer peptide fragments of HSPB5 and treated mice at the peak of disease with 10 µg of each peptide every other day, using HSPB5 as a positive control and PBS as a negative control. In the initial screen, we found that four out of the ten 15-mer sequences were therapeutic, with peptide 71-85 demonstrating marked therapeutic efficacy (FIG. 4 and Table 1).

Figure 5A:
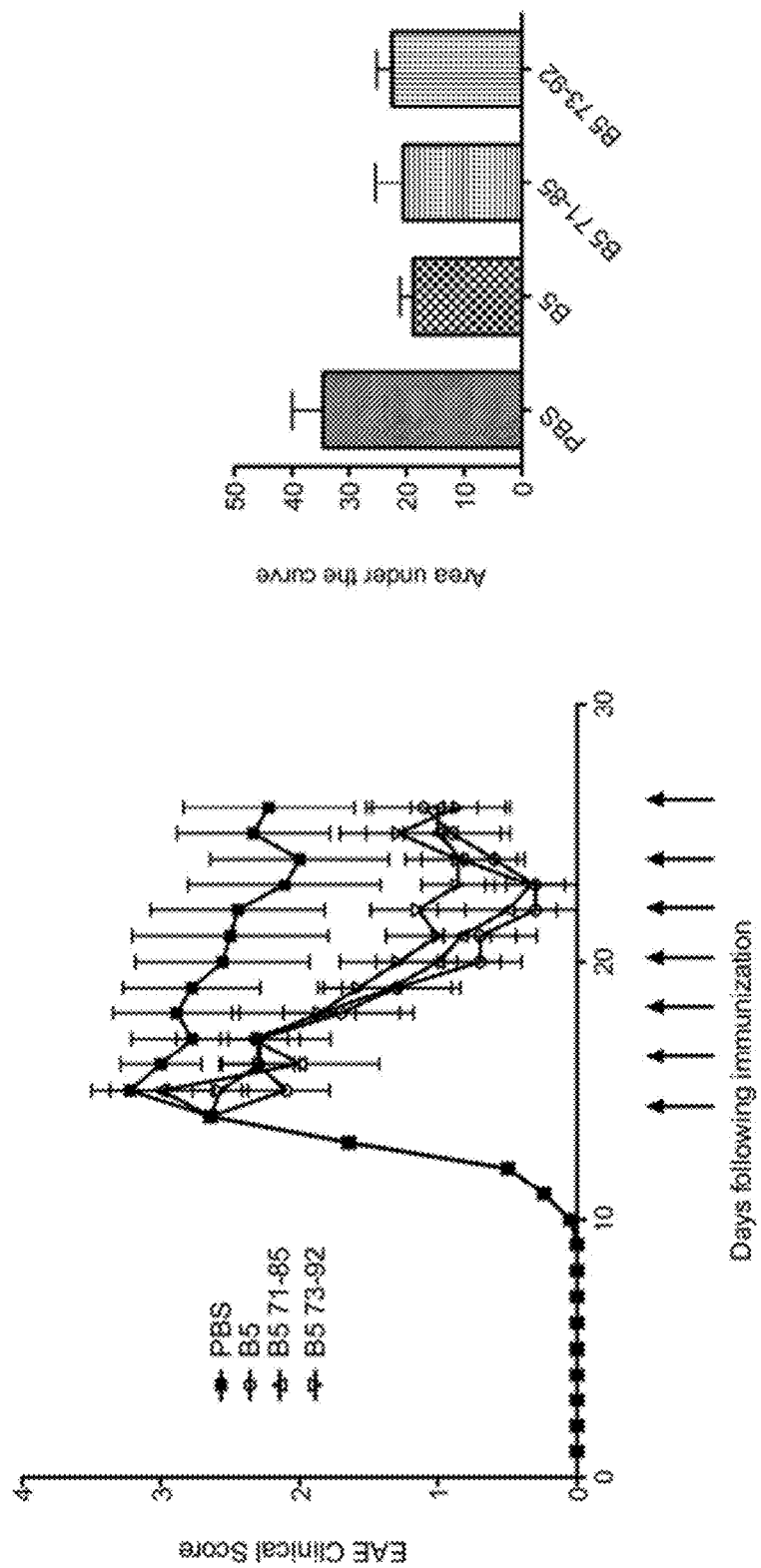
FIG. 5. Peptide sequence 73-92 is therapeutic in EAE. a) 129Sv WT mice were immunized with MOG25-55/CFA and 10 μg of HSPB5 peptide sequence 71-8 and 73-92 were given every other day beginning at the peak of disease. HSPB5 73-92 is as therapeutic as HSPB5 71-85 (n>9 mice per group, *p<0.05). b) 73-93 peptide region in both HSPB1 and HSPB4 are as therapeutic as full length proteins when given at the peak of disease in equal molar ratios (1 μg/peptide and 10 μg/protein, n>10 mice per group, *p<0.05). c) 73-92 is capable of suppressing splenocyte pro-inflammatory cytokine production (triplicates, n=3 experiments, *p<0.05).
Figure 5B:
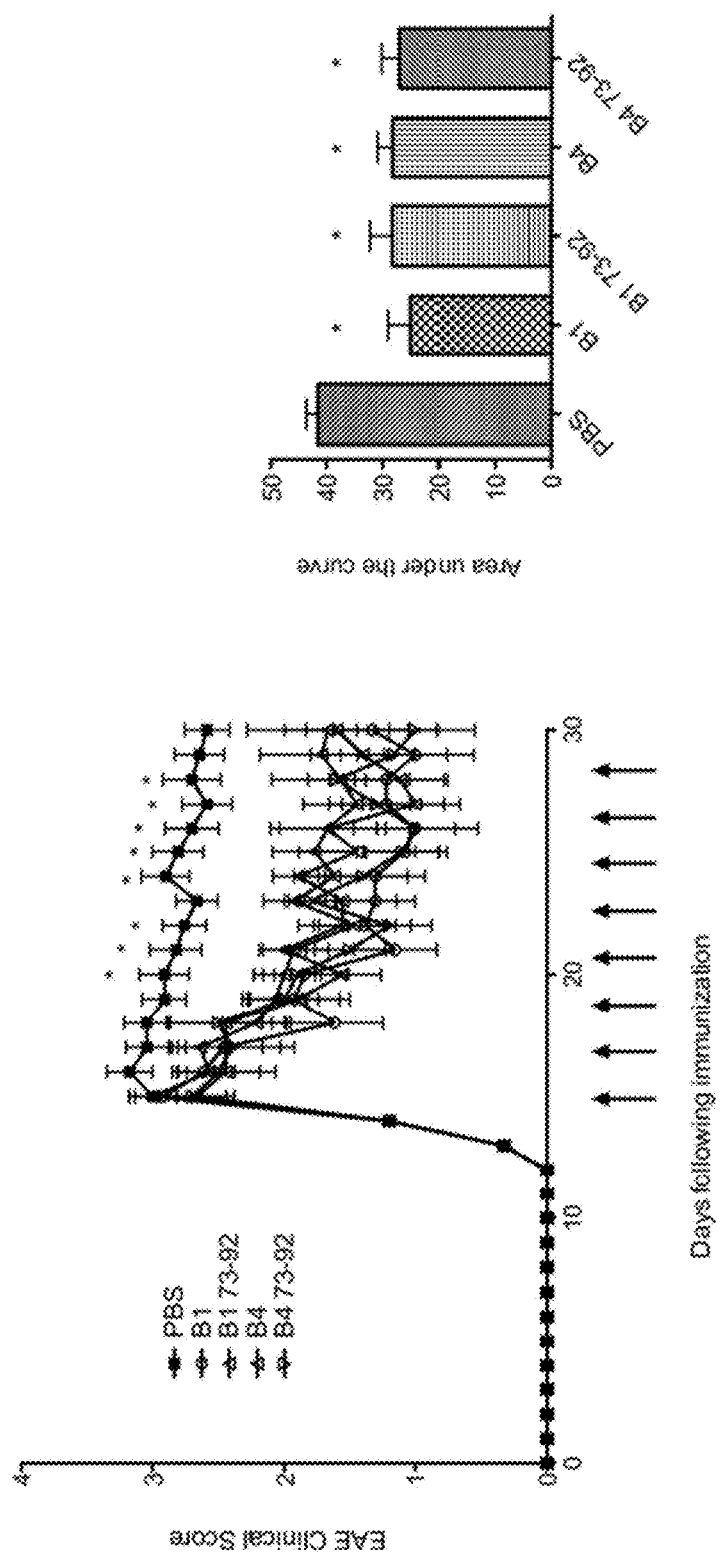
Figure 5C:
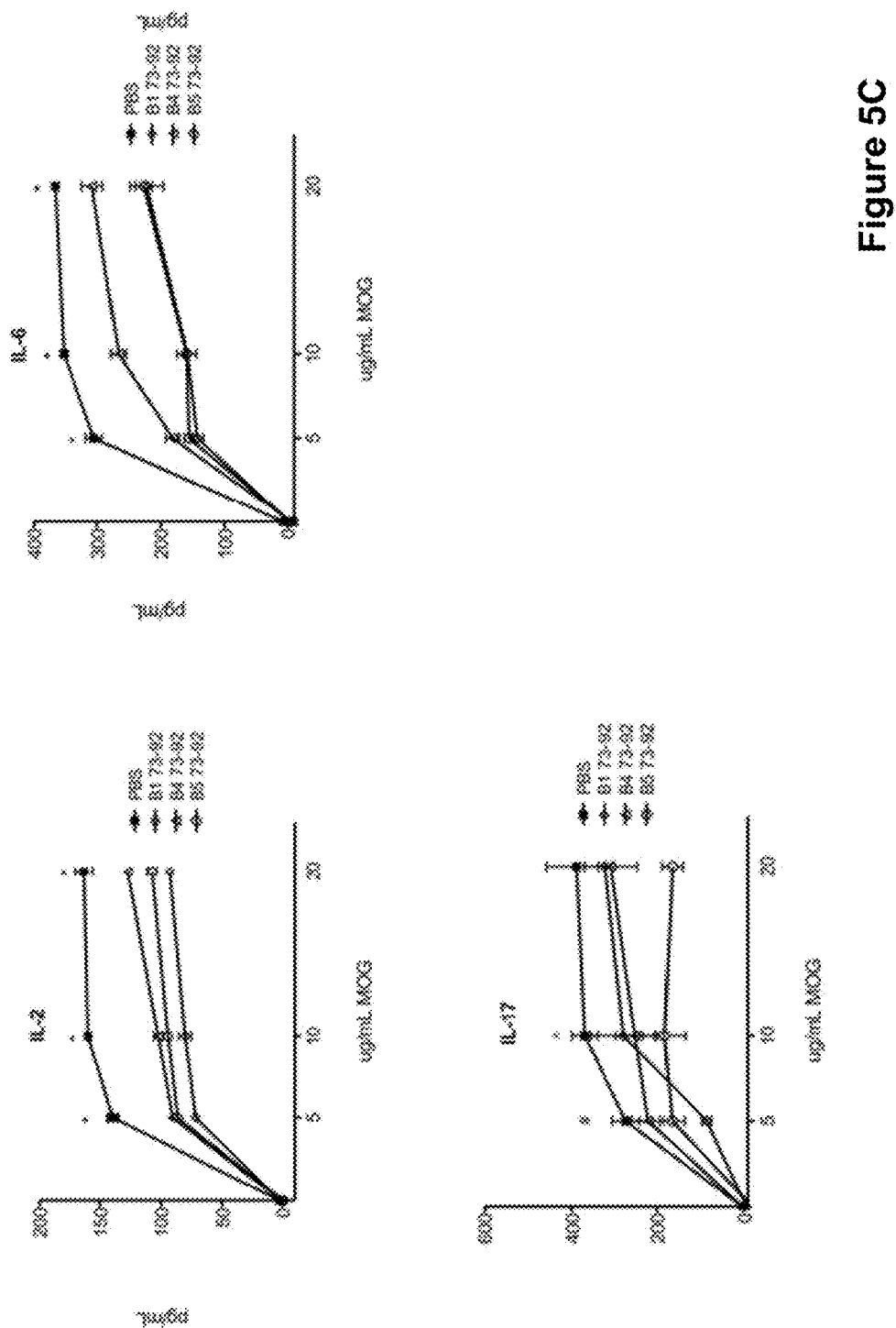

HSPB5 73-92 has been shown to be important for molecular chaperone activity in vitro, so we treated EAE mice at the peak of disease with HSPB5 73-92 and found that equal molar ratios of full length protein and peptide were comparably therapeutic (FIG. 5a). Since molecular chaperone activity was a common feature of the whole family of small heat shock proteins and there was 75% amino acid similarity between HSPB1, HSPB4, and HSPB5 in this peptide region, we investigated whether this peptide sequence of HSPB1 or HSPB4 was therapeutic. We found that peptide sequence 73-92 in both HSPB1 and HSPB4 was therapeutic in EAE, similar to the HSPB5 peptide 73-92 (FIG. 5b). HSPB1 73-92, HSPB4 73-92, and HSPB5 73-92 were all also to decrease peripheral immune activation, measured by the MOG stimulated production of pro-inflammatory cytokines from the spleens of MOG immunized mice (FIG. 5c).

TABLE 2

Figure 6A:
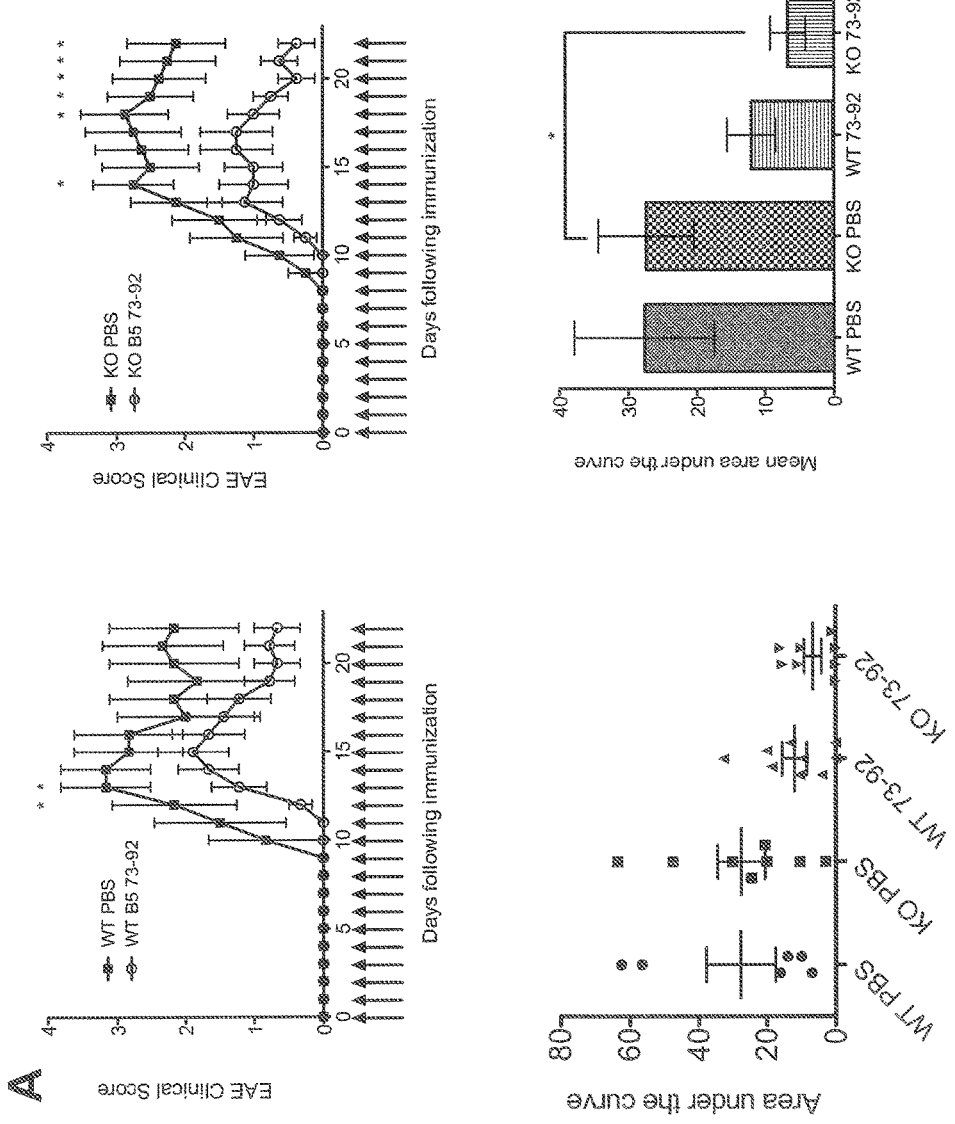
FIG. 6. Rescue with HSPB5 73-92 peptide reduces disease severity of EAE in WT and HSPB5 KO mice. a) 129Sv WT mice and 129Sv HSPB5−/− mice were immunized with MOG35-55/CFA and treated with 10 μg of peptide every day beginning at Day 0 (n>8 mice per group). HSPB5 73-92 ameliorated EAE in both WT and HSPB5−/− (*p<0.05). b) 129Sv HSPB5−/− mice were immunized with MOG35-55/CFA and treated with 10 ug of peptide every other day beginning at the peak of disease. HSPB5 73-92 was sufficient to ameliorate disease in the HSPB5 deficient mice (n>6 mice per group, *p<0.05).

Pre-treatment with HSPB5 73-92 peptide delays onset of EAE in HSPB5 KO mice. HSPB5−/− mice were immunized with MOG35-55/CFA and treatment with HSPB5 73-92 began at Day 0 (FIG. 6). Mice treated with peptide had a delayed onset and lower incidence of disease than mice treated with PBS (n > 8 mice per group).

|  | Day 11 | Day 12 | Day 13 | Day 14 | Day 15 | Day 16 | Day 17 | Day 18 |
|---|---|---|---|---|---|---|---|---|
| PBS | 0% | 0% | 56% | 56% | 78% | 100% | 100% | 100% |
| HSPB5 73-92 | 0% | 0% | 11% | 33% | 33% | 33% | 66% | 66% |

Previously it had been established that HSPB5 was therapeutic in EAE and acted through its anti-inflammatory effects. This study extends that work and demonstrates that the therapeutic efficacy of HSPB5 is a characteristic com-

TABLE 1

Summary table of HSPB5 peptide screen. The area under the curve was calculated for the average EAE scores for HSPB5 peptides that were screened in FIG. 4 normalized to PBS.

| HSPB5 PEPTIDE | AMINO ACID SEQUENCE | AREA UNDER THE CURVE (amount higher than HSPB5 normalized to PBS) | THERAPEUTIC (less than 0.10) |
|---|---|---|---|
| 11-25 | RRPFFPFHSPSRLFD (SEQ ID NO: 14) | −0.11 | + |
| 21-35 | SRLFDQFFGEHLLES (SEQ ID NO: 15) | 0.28 | − |
| 31-45 | HLLESDLFPTSTSLS (SEQ ID NO: 16) | 0.33 | − |
| 41-55 | STSLSPFYLRPPSFL (SEQ ID NO: 17) | 0.28 | − |
| 51-65 | PPSFLRAPSWFDTGL (SEQ ID NO: 18) | 0.10 | − |
| 71-85 | EKDRFSVNLDVKHFS (SEQ ID NO: 19) | 0.06 | + |
| 111-125 | HGFISREFHRKYRIP (SEQ ID NO: 20) | 0.33 | − |
| 131-145 | LTITSSLSSDGVLTV (SEQ ID NO: 21) | 0.08 | + |
| 151-165 | QVSGPERTIPITREE (SEQ ID NO: 22) | 0.29 | − |
| 161-175 | ITREEKPAVTAAPKK (SEQ ID NO: 23) | 0.08 | + |

Figure 6B:
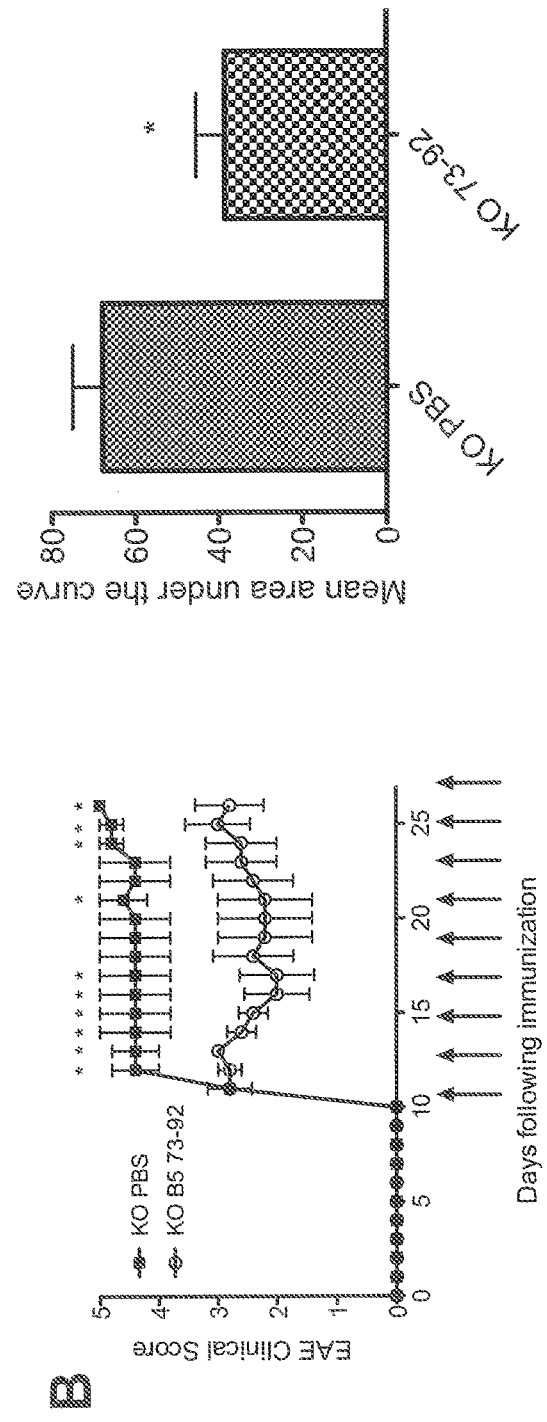

Efficacy of HSPB5 73-92 in EAE in HSPB5 deficient mice. We tested whether HSPB5 73-92 alone was sufficient to rescue EAE in alpha B crystallin deficient (HSPB5−/−) mice. Previously published data had shown that full-length HPPBS was able to treat not only WT mice, but also HSPB5 deficient mice. WT mice treated in a prevention paradigm with B5 73-92 starting at Day 0 had lower disease severity (FIG. 6a) and a delayed onset of disease (Table 2). When HSPB5−/− mice were treated with B5 73-92 beginning at Day 0, mice showed both lower EAE clinical scores (FIG. 6a) and delayed onset of disease (Table 2) compared to HSPB5−/− mice treated with PBS. HSPB5−/− mice treated at the peak of disease with HSPB5 73-92 also showed lower disease scores (FIG. 6b).

mon to all members of the small heat shock protein family. Furthermore, it establishes that the therapeutic effect of HSPB5 is independent of its tertiary structure and that small peptide fragments have similar therapeutic effects as full-length proteins. This study also illustrates the use of small heat shock proteins as therapeutics for neurological diseases like multiple sclerosis, and neurological diseases with an inflammatory component, such as Alzheimer's disease, Parkinson's disease, epilepsy, or even prions.

Materials and Methods

Cloning, expression, and purification of T7-human sHspB1-9. The full-length clones of human sHspB1-8 were obtained from Open Biosystems. The proteins were cloned by introducing an Eco R1, an ATG site, a HindII, and stop site using PCR. The resulting sHsp PCR fragments were ligated into the EcoR1-HindIII restriction site of pET21b (+) (Novagen) in frame with the amino terminal T7-tag. One-shot TOP10 cells (Invitrogen) were transformed with the resulting plasmid. Several of the resulting colonies were selected, expanded, and the insertion was verified by restriction digest with EcoR1 and HindIII, and sequencing. The proteins were produced in small scale by transforming BL21 Codon Plus cells (Stratagene) for protein expression. Larger scale production and purification of T7-HspB1-8 was accomplished by growing selected colonies in 250-1000 ml of LB broth with carbenicillin, induced with IPTG, and isolating the bacteria 4-12 hours later. The cells were lysed with a bacterial protein extraction buffer (Thermo) with sonication while being cooled on ice, and the supernatant collected after centrifugation, saturated ammonium sulfate was added to 20% v/v, and the mixture centrifuged. Sufficient saturated ammonium sulfate was added to the supernatant to increase the concentration of the solution to 45% v/v. After centrifugation the pellet containing HspB1-8 was resuspended in 50 mM NaCl and 50 mM Tris pH 8.0. Additional sHsp was recovered by extracting the initial pellet in the 20% ammonium sulfate precipitation with 6M guanidine hydrochloride 100 mM Tris pH8.0 and dialysis against 50 mM NaCl and 50 mM Tris pH 8.0. The dialyzed mixture was spun and the supernatant combined with the resuspended pellet from the 50% ammonium sulfate precipitation and applied to DEAE fast flow column to remove DNA and negatively charged glycosoaminoglycans. The flow through was concentrated and applied to a Sephacryl S-300 column. The fractions corresponding to the large Mr sHsp (approx. 400 kD) were pooled and concentrated, and finally applied to an anti-T7 column, and the T7-sHsps were eluted with glycine buffer pH3.0. The eluate was neutralized with 1M Tris pH 8.0, concentrated. The purity of the protein was established using Coomassie stained SDS PAGE gels, while the structure was confirmed by mass spectrometry. The quaternary structure was established using gel filtration on Sephacryl S-300 and by dynamic light scattering.

EAE induction and scoring. Mice were immunized subcutaneously with 100 µL of myelin oligodendrocyte glycoprotein (MOG) peptide 35-55 (2 mg/mL) and Complete Freund's adjuvant (CFA) (4 mg/mL) on Day 0. Mice were monitored until they showed clinical signs of sickness around Day 12 to Day 20. Mice were randomized at the peak of disease into the treatment groups where they received 10 ug/200 µL of sHSP, 1 µg/200 uL of sHSP peptide, or 200 µL of PBS (vehicle) every other day. Mice were scored every day on a clinical scoring system: 0, healthy mouse; 1, limp tail; 2, weak hindlimbs; 3, complete hindlimb paralysis; 4, weak forelimbs and paralyzed hindlimbs; 5, dead.

Peripheral immune cell activation and cytokine analysis. Spleens and lymph nodes were isolated from mice 9 days after immunization with MOG35-55 and CFA. Spleens were mechanically disrupted to isolate single cell splencytes suspension. Cells were cultured in flat bottomed, 96-well plates in media (RPMI 1640 supplemented with 2 mL L-glutamine, 1 mM sodium pyruvate, 0.1 mM non-essential amino acids, 100 U/mL penicillin, 0.1 mg/mL streptomycin, 0.5 uM 2-mercaptoethanol, and 10% fetal calf serum). Cells were stimulated with MOG35-55 (5 ug/mL, 10 ug/mL, and 20 ug/mL). For all activation assays, splenocytes were pooled from three mice per group and triplicate wells were plated. Supernatants of cells were collected at the time of peak production for each cytokine (48 hrs: IL-2, IL-12p40, IL-6; 72 hrs: TNFα and IFNγ; 96 hrs: IL-17; 120 hrs: IL-10). Cytokines were measured in the supernatants using anti-mouse OPTEIA ELISA kits (BD Pharmingen for IFNγ, IL-10, IL-2, IL-6, and IL-12p40; R&D Systems for IL-17 and TNFα).

Example 2

Alpha B Crystallin is an Endogenous Immunomodulatory Response Element that can be Used as a Therapeutic 12 Hours after Stroke This report describes an effective treatment of stroke, even 12 h after onset, by the administration of alphaB-crystallin (Cryab), an endogenous immunomodulatory neuroprotectant. In Cryab$^{-/-}$ mice, there was increased lesion size and diminished neurologic function after stroke compared to wild-type mice. This difference was in part due to deficiency of Cryab in the immune system. Increased plasma Cryab was detected after experimental stroke in mice and after stroke in human patients. Administration of Cryab even 12 hours post-experimental stroke provided clinical benefit and reduced stroke pathology. Inflammatory cytokines associated with stroke pathology were reduced with exogenous administration. Cryab is an endogenous anti-inflammatory and neuroprotectant molecule produced after stroke, whose beneficial properties can be augmented when administered therapeutically after stroke.

Figure 7:
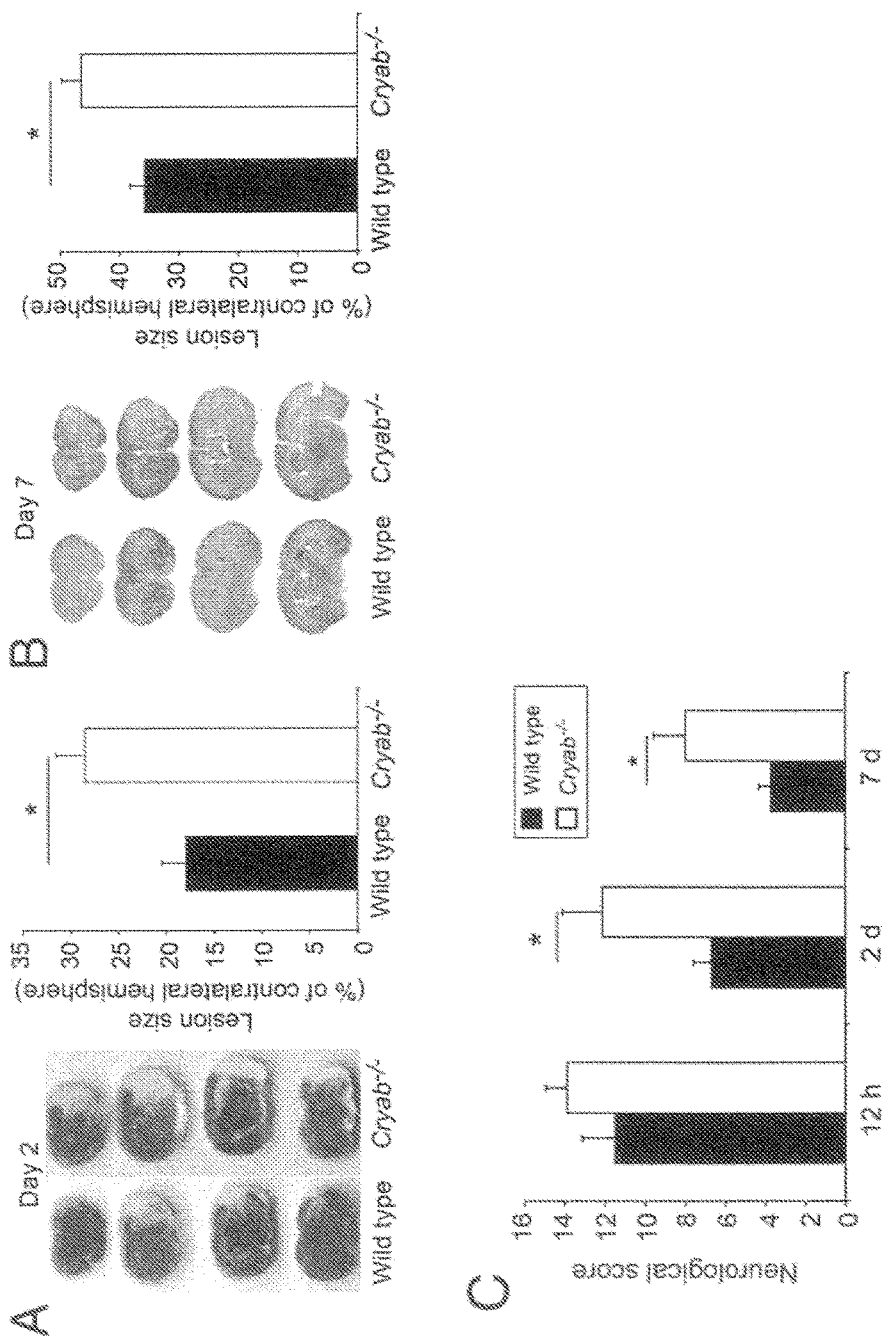
FIG. 7. Cryab$^{-/-}$ mice have larger lesions and worse neurological scores. (a) Representative images of TTC-stained brain sections of wild-type and Cryab$^{-/-}$ mice (left panel) and quantification of lesion sizes at 2 d after stroke (right panel, n=10 per group). (b) Representative images of silver stained brain sections (left panel) and quantification of lesion sizes at 7 d after stroke (right panel). (c) Quantification of 28-point neurological scoring in wild-type and Cryab$^{-/-}$ mice at 12 h, 2 d and 7 d after stroke. For b and c, n=10 and 7 for wild-type and Cryab$^{-/-}$ groups, respectively. *P<0.05, Student's t-test.
Figure 8:
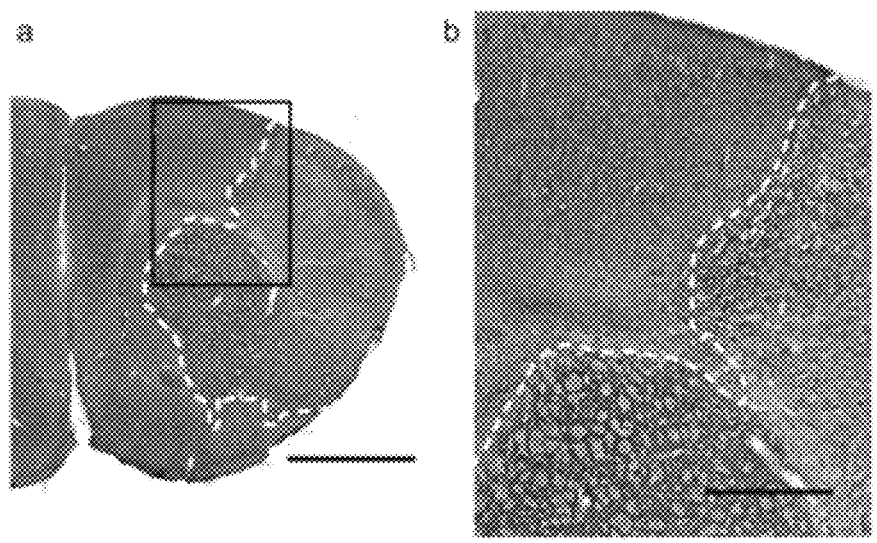
FIG. 8. High-contrast silver stain images. (a) Representative higher magnification silver stained images of brain sections 7 d after stroke, scale bar=2 mm. (b) higher magnification of the black lined rectangle in a, scale bar=500 μm. The dashed white lines indicate the border between the healthy and lesion areas.
Figure 9:
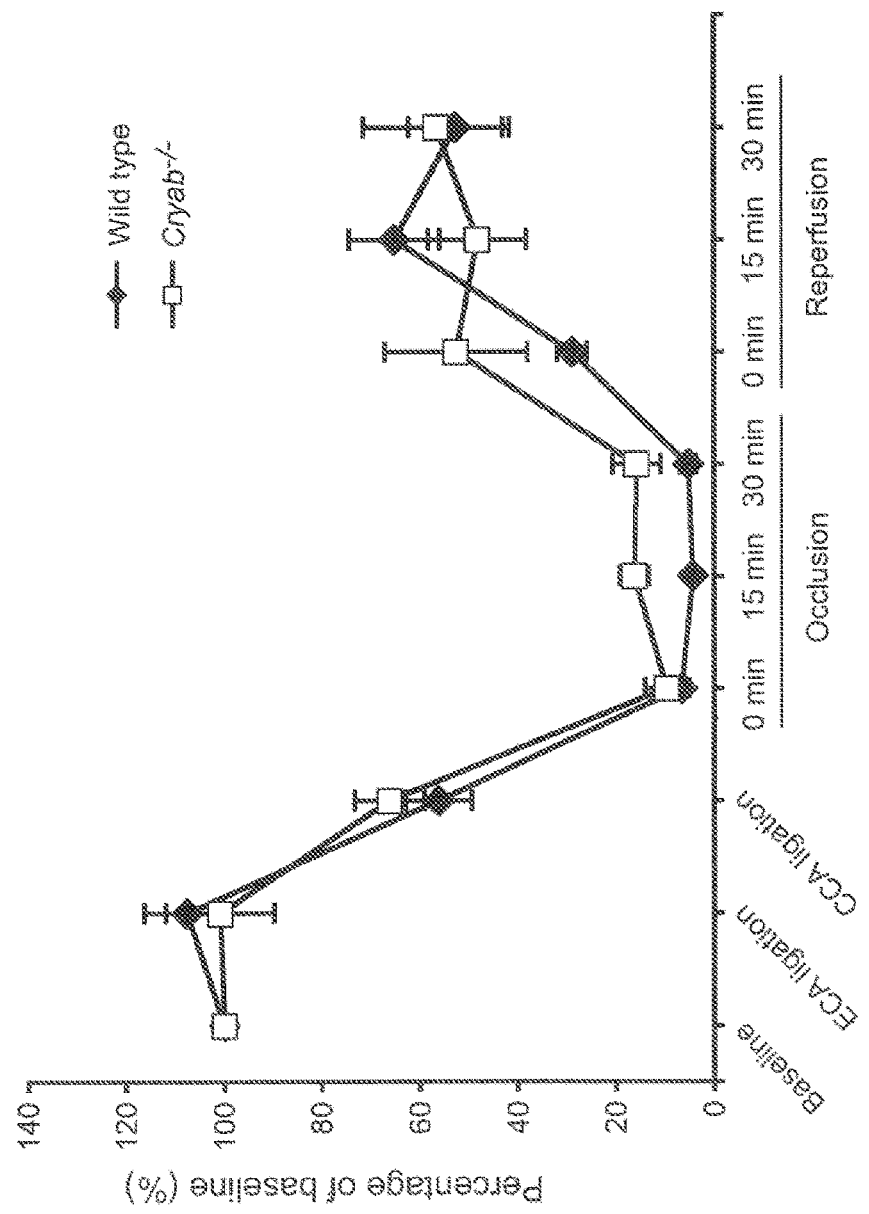
FIG. 9. Cerebral blood flow change during and after stroke surgery between wild-type and Cryab-/- mice is not different. The laser Doppler flowmeter results of wild-type and Cryab-/- mice before and during the MCA occlusion and up to 30 min after reperfusion. n=4 per group.

Cryab$^{-/-}$ mice have larger lesion sizes. To investigate the effects of Cryab deficiency on cerebral ischemia, wild-type and Cryab$^{-/-}$ mice were exposed to 30 minutes of middle cerebral artery occlusion. The Cryab$^{-/-}$ mice had significantly larger lesion sizes at 2 days (2 d) as assessed by triphenyltetrazolium chloride (TTC) staining (FIG. 7a). This difference remained at 7 days (7 d) after stroke as assessed by silver stain (FIG. 7b and FIG. 8), indicating that the deficiency of Cryab affected both the early and delayed phases of ischemic damage. Functional outcome was assessed by a 28-point neurological scoring test. The Cryab$^{-/-}$ mice had significantly worse scores at both 2 d and 7 d time points compared to wild-type controls (FIG. 7c). No differences were seen in cerebral blood flow measured by laser doppler flow-meter immediately after the occlusion and at 15 and 30 minutes of reperfusion between the groups (FIG. 9).

Figure 10:
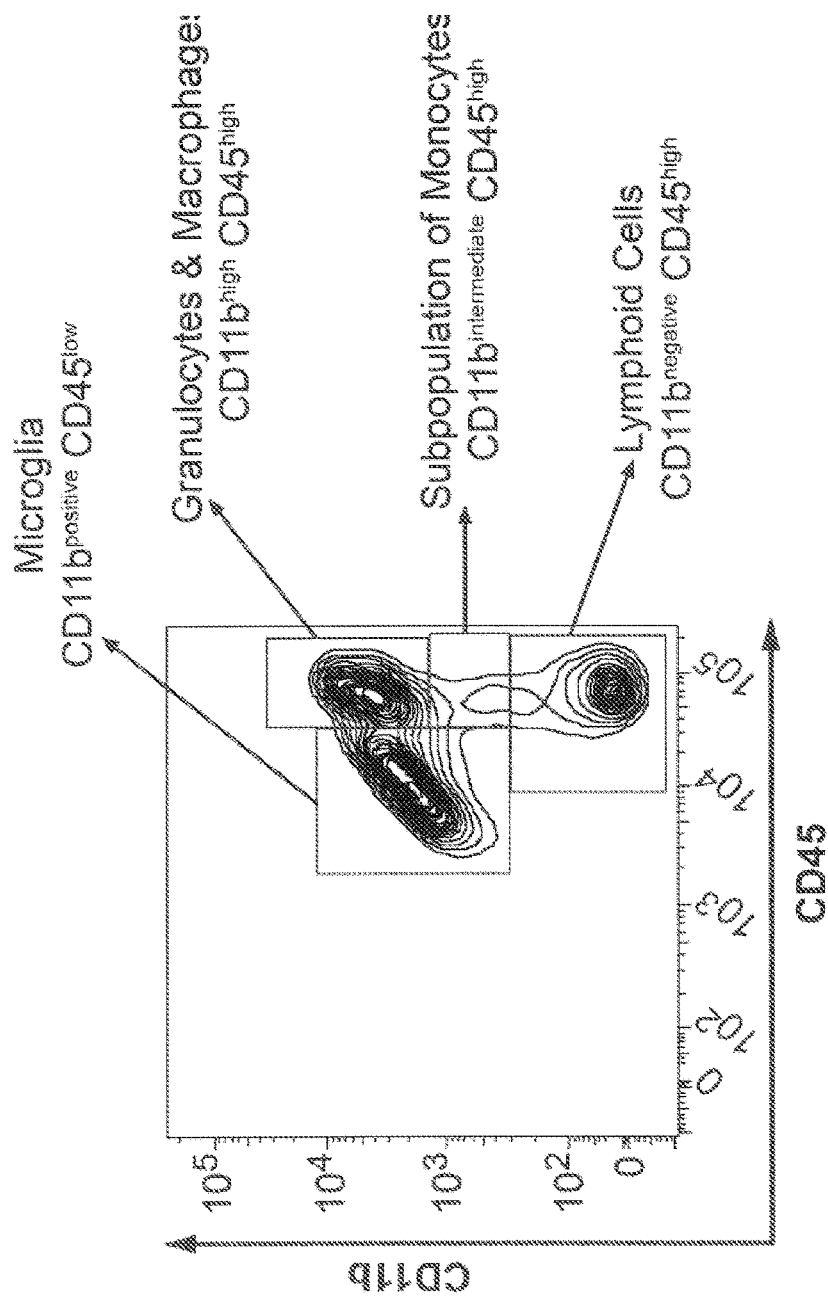
FIG. 10. Representative CD11b and CD45 plot of brain immune cells after stroke. Four populations were identified according to the CD11b and CD45 expression pattern. CD11b$_{positive}$CD45$_{low}$: Microglia; CD11b$_{high}$CD45$_{high}$: Granulocytes & Macrophages; CD11b$_{low}$CD45$_{high}$: Subpopulation of monocytes; CD11b$_{negative}$CD45$_{high}$: Lymphoid cells.
Figure 11:
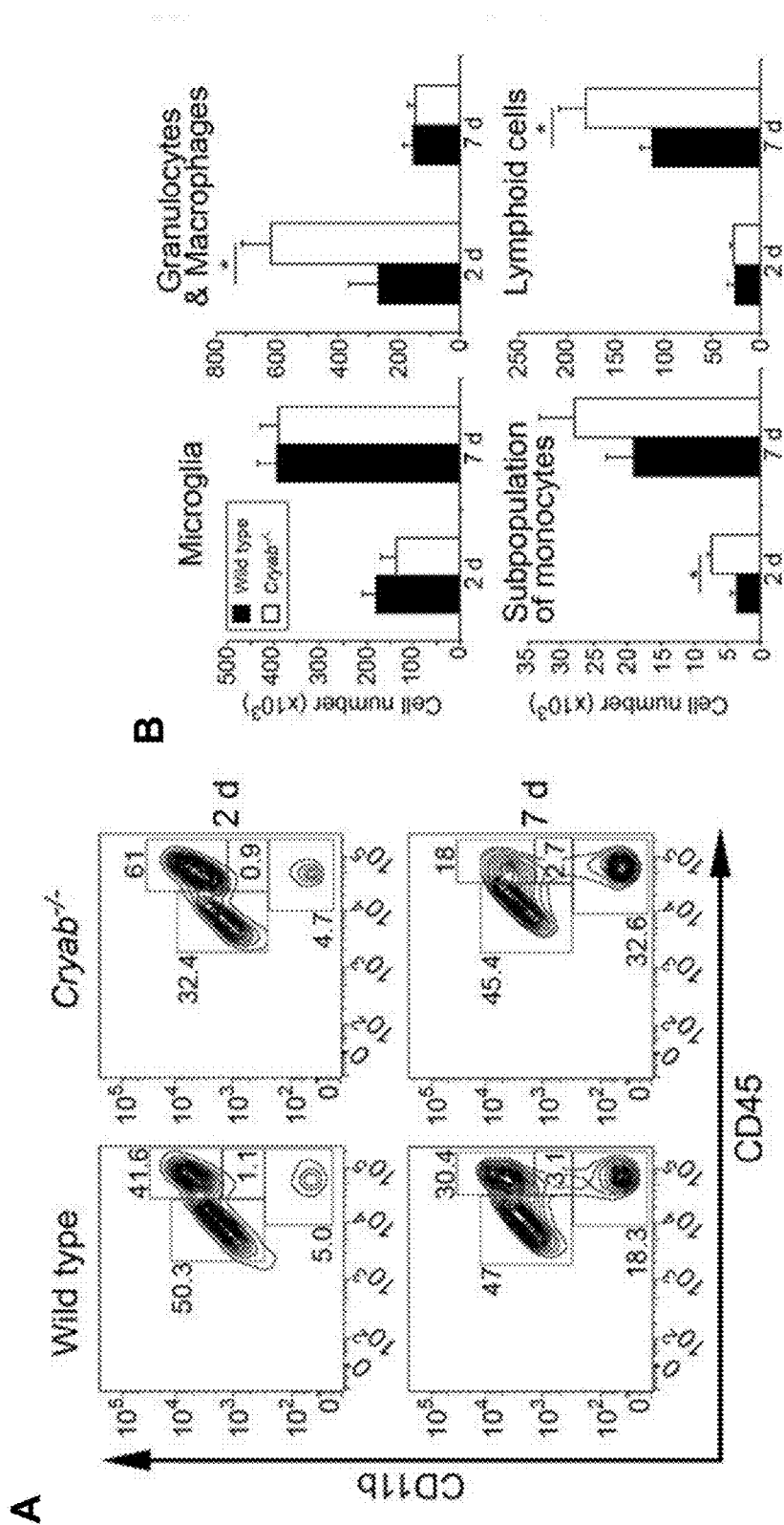
FIG. 11. There is more immune cell infiltration in brains of Cryab$^{-/-}$ mice and Cryab deficiency in the immune system causes larger lesion sizes after stroke. (a) Representative CD45 vs CD11b flow cytometry plots of brain immune cells in wild-type and Cryab$^{-/-}$ mice at 2 d and 7 d after stroke. (b) Quantification of total cell numbers of microglia (CD11b$^+$CD45$^{low}$), granulocyte and macrophages (CD11b$^{high}$CD45$^{high}$), subpopulation of monocytes (CD11b$^{low}$CD45$^{high}$), lymphoid cells (CD11b$^{negative}$CD45$^{high}$) in wild-type and Cryab$^{-/-}$ mice brains at 2 d and 7 d after stroke. (c) Schematic plots showing the analysis method with F4/80 and Gr1 markers of CD11b$^{high}$CD45$^{high}$ population (F4/80$^{negative}$Gr1$^+$: granulocytes, F4/80$^+$Gr1$^+$: activated macrophages, F4/80$^+$Gr1$^{negative}$: macrophages). (d) Quantification of granulocytes, activated (act.) macrophages and macrophages in wild-type and Cryab$^{-/-}$ mice brains at 2 d and 7 d after stroke. (e) Representative CD45 vs CD3 flow cytometry plots of brain immune cells in wild-type and Cryab$^{-/-}$ mice at 2 d and 7 d after stroke. (f) Quantification of number of CD3$^+$, CD3$^+$ CD4$^+$, CD3$^+$CD8$^+$ and CD3$^+$γδTCR$^+$ T cells. n=6 per group for each time point. *P<0.05, Mann-Whitney analysis. (g) Number of T cells vs. IL-17a. (h) Scheme of timetable for the bone-marrow chimeric mice experiments. (i) Quantification of lesion sizes at 7 d after stroke in the bone-marrow chimeric mice, wild-type cells into wild-type host: WT→WT, Cryab$^{-/-}$ cells into wild-type host: KO→WT, wild-type cells into Cryab$^{-/-}$ host: WT→KO, Cryab$^{-/-}$ cells into Cryab$^{-/-}$ host: KO→KO, n=10 for all groups except KO→KO (n=6). *P<0.05, **P<0.01, $^\#$P=0.063, Student's t-test. Data represent means±s.e.m.
Figure 11:
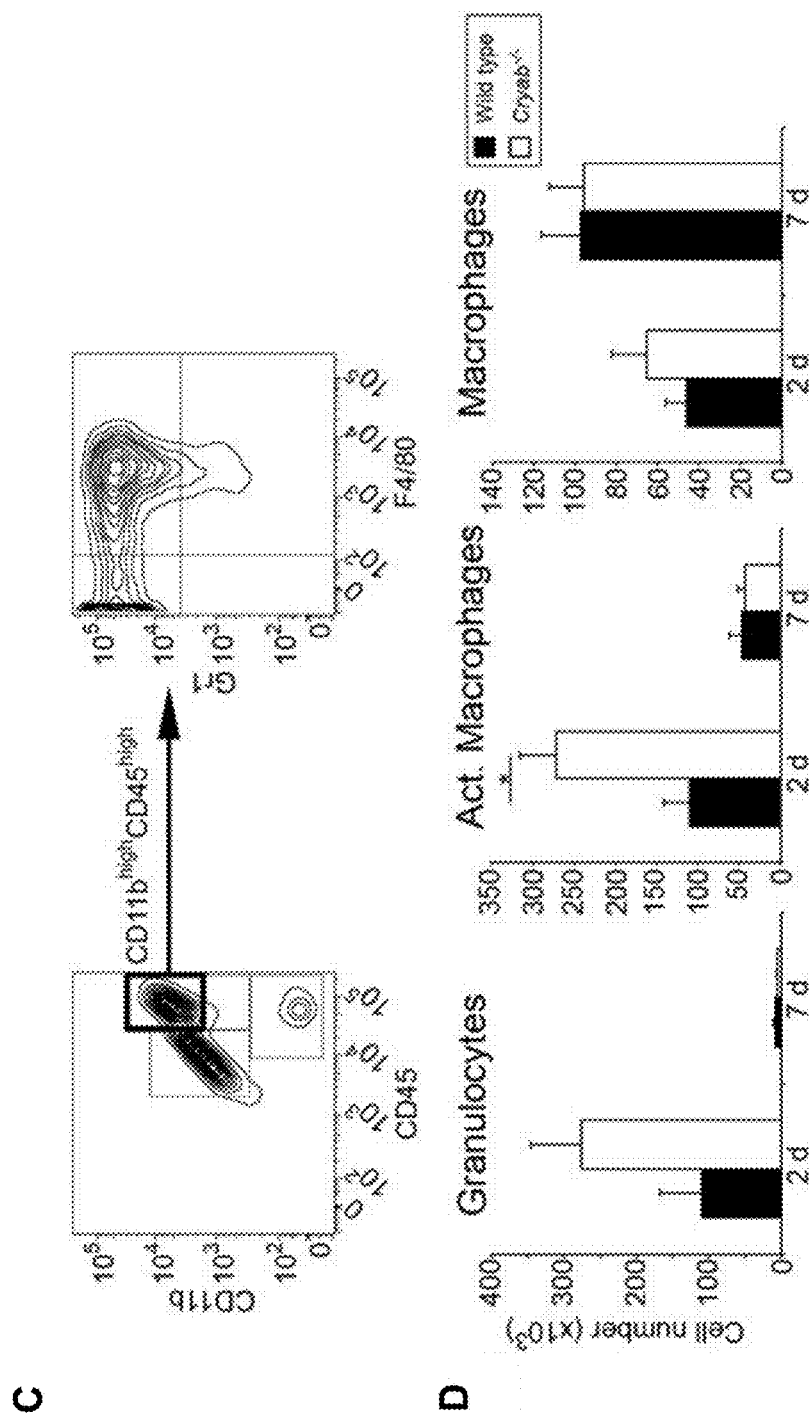
Figure 11:
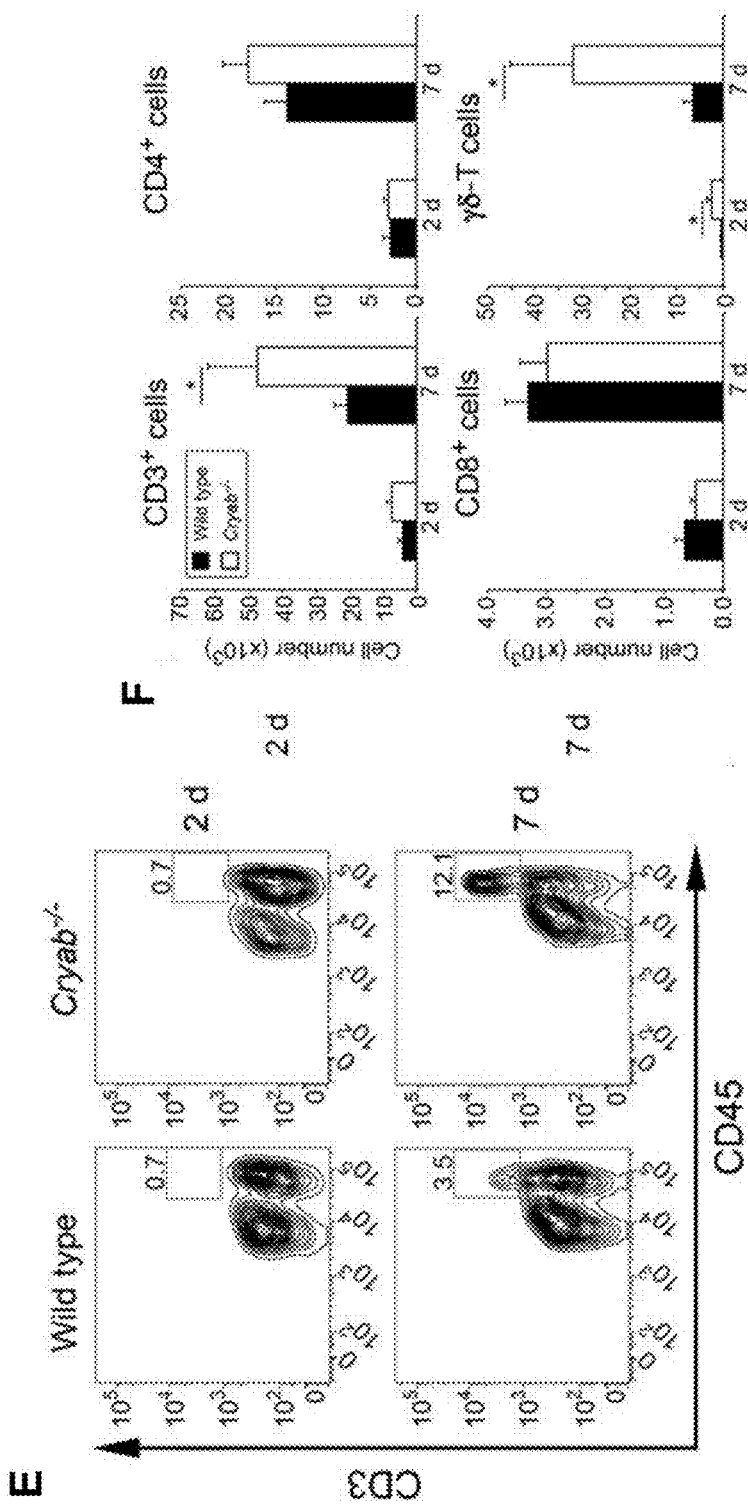
Figure 11:
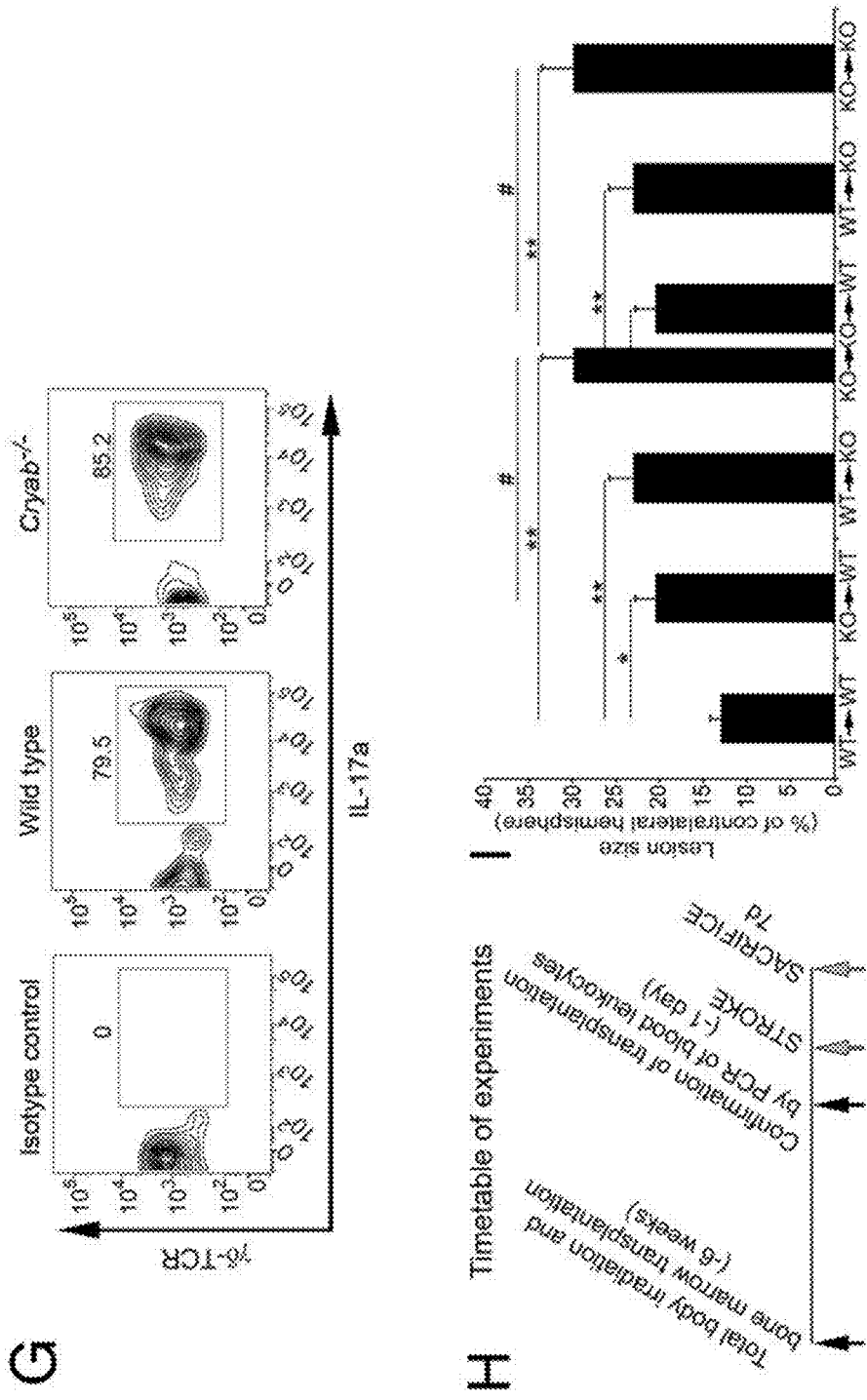

Cryab$^{-/-}$ immune system causes larger lesions after stroke. To investigate the role of the immune system in ischemic neuropathology associated with stroke, the profile of mononuclear cells in the ischemic wild-type and Cryab$^{-/-}$ brains was characterized. We identified four distinct cell populations according to their CD45 and CD11b expression patterns: CD11b$^+$CD45$^{low}$ (microglia), CD11b$^{high}$CD45$^{high}$ (granulocytes and macrophages), CD11b$^{low}$CD45$^{high}$ (subpopulation of monocytes), and CD11b$^{negative}$CD45$^{high}$ (lymphoid cells) (FIG. 10). The brain invasion of granulocytes and macrophages was higher in both groups at the earlier (2 d) time point whereas the lymphoid cells increased more at the later (7 d) time points (FIG. 11a), consistent with other reports[273]. The total number of microglial cells was equivalent in wild-type and Cryab$^{-/-}$ mice at both the 2 d and 7 d time points (FIG. 11b). However, the numbers of granulocyte and macrophage populations and the subpopulation of monocytes were significantly higher in the Cryab$^{-/-}$ mice brains at 2 d but not at 7 d compared to wild-type mice (FIG. 11b). Moreover, the numbers of lymphoid cells were significantly higher in the Cryab$^{-/-}$ group at 7 d (FIG. 11b).

The granulocyte and macrophage population was further analyzed with Gr1 and F4/80 markers to identify granulocytes and macrophages separately. In the CD11b$^{high}$CD45$^{high}$ population, three subpopulations were identified (FIG. 11c): F4/80$^{negative}$Gr1$^{positive}$ (granulocytes), F4/80$^{positive}$Gr1$^{positive}$ (activated macrophages), F4/80$^{positive}$Gr1$^{negative}$ (macrophages). There were more granulocytes and significantly higher numbers of activated macrophages in Cryab$^{-/-}$ mice at 2 d (FIG. 11d). The number of macrophages was equivalent at both time points between the groups (FIG. 11d).

The analysis of T cells (CD3') showed that the total number of T cells increased at 7 d compared to 2 d in both groups and there were significantly more T cells in the brains of Cryab$^{-/-}$ mice than wild-type mice at 7 d (FIG. 11e, f). When we analyzed the T cell subpopulations, no difference in CD4$^+$ and CD8$^+$ T cells were observed between wild-type and Cryab$^{-/-}$ groups (FIG. 11f). However, there were significantly more gd-TCR$^+$ (gd-T) cells in the brains of Cryab$^{-/-}$ mice at 2 d and 7 d after ischemia (FIG. 11f). Moreover, these gd-T cells were producing IL-17 (FIG. 11g), hence, causing damage rather than tolerance as suggested before.

The number of all cell populations in the spleens of Cryab$^{-/-}$ mice was significantly decreased at 2 d after stroke, suggesting a stronger inflammatory response associated with larger lesion sizes (Tables 3, 4). There was no difference in the numbers of splenocyte populations before and 7 d after stroke between wild-type and Cryab$^{-/-}$ mice (Tables 3, 4). There were no differences in the number of CD11b$^+$ cells and CD3$^+$, CD4$^+$ and CD8$^+$ T cells in blood of wild-type and Cryab$^{-/-}$ mice before, 2 d and 7 d after stroke (Table 5, 6). However, there were more gd-T cells in blood of Cryab$^{-/-}$ mice before and 7 d after, but not 2 d after stroke (Table 7). The difference of blood gd-T cell numbers between Cryab$^{-/-}$ and wild-type mice was 2.7-fold before stroke whereas it was 6-fold at 7 d, implying a stronger inflammatory response in Cryab$^{-/-}$ mice (Table 7). There were no differences in the number of any mononuclear cell populations in the brains of wild-type and Cryab$^{-/-}$ mice before stroke (Table 8). Overall, these data suggest that the deficiency of Cryab leads to a more vigorous inflammatory response to stroke. The extent of inflammation can be proportional to the lesion size and various inflammatory markers correlate with clinical outcome after stroke.

Cryab has been shown to have both anti-inflammatory properties by inhibition of NF-kB and p38 MAP kinase as well as anti-apoptotic properties by inhibition of activation of caspase-3. To further dissect whether the more vigorous inflammatory response seen in Cryab mice might be due to the larger lesion sizes in Cryab$^{-/-}$ mice, or vice versa, we performed bone marrow chimera experiments. After a lethal dose of total body gamma irradiation, wild-type or Cryab$^{-/-}$ bone-marrow cells were injected into either wild-type or Cryab$^{-/-}$ mice to regenerate the immune system. We had four groups: wild-type cells transferred to wild-type hosts (WT→WT), wild-type cells transferred to Cryab$^{-/-}$ hosts (WT→KO), Cryab$^{-/-}$ cells transferred to wild-type hosts (KO→WT), and Cryab$^{-/-}$ cells transferred to Cryab$^{-/-}$ hosts (KO→KO). Death within two weeks of irradiated WT and Cryab$^{-/-}$ mice that were not given cells to repopulate their immune systems confirmed that it was a lethal irradiation. Six weeks after the irradiation, we confirmed the chimerism by PCR of blood leukocytes for Cryab, so that the mice that were given wild-type and Cryab$^{-/-}$ cells had only wild-type and Cryab$^{-/-}$ genotypes in their immune system, respectively (FIG. 11h). The KO→KO group had significantly larger lesion sizes than WT→WT group (FIG. 11i). This is concordant with the previous finding of Cryab$^{-/-}$ mice having larger lesions than wild-type mice. The KO→WT group had significantly larger lesions than WT→WT group (FIG. 11i). There was also a trend of larger lesions in KO→KO group than WT→KO group (FIG. 11i). Taken together these studies all indicate that a deficiency of Cryab in the immune system is associated with larger lesions in both wild-type and Cryab$^{-/-}$ hosts. Therefore, the presence or absence of Cryab in the immune system is critical in the evolution of infarct. Furthermore, WT→KO group had significantly larger lesions than WT→WT group (FIG. 11i). There was also a trend of larger lesions in KO→KO group than KO→WT group (FIG. 11i). This suggests that the difference in lesion sizes between wild-type and Cryab$^{-/-}$ mice is not only due to the Cryab deficiency in the immune system but also due to the deficiency of Cryab outside the immune system, and within the central nervous system, as well. These results indicate that Cryab deficiency in both the immune system and as well as Cryab deficiency in brain each independently contribute to the larger lesions in Cryab$^{-/-}$ mice compared to wild-type mice.

TABLE 3

The number of cells in various splenocyte populations in wild-type and Cryab$^{-/-}$ mice before and 2 d and 7 d after stroke (×10$^4$ cells)

| | | CD11b$^{negative}$ CD45$^{high}$ | CD11b$^{negative}$ CD45$^{high}$ | CD11b$^{high}$ CD45$^{high}$ | CD11b$^{high}$CD45$^{high}$ F4/80$^{negative}$Gr1$^+$ |
|---|---|---|---|---|---|
| Naive | Wild-type | 8797 ± 414 | 149 ± 8 | 193 ± 29 | 76 ± 15 |
| | Cryab$^{-/-}$ | 8036 ± 883 | 150 ± 24 | 154 ± 37 | 66 ± 16 |
| 2 d | Wild-type | 4237 ± 422 | 46 ± 4 | 149 ± 27 | 88 ± 16 |
| | Cryab$^{-/-}$ | 1401 ± 350* | 17 ± 4* | 50 ± 18* | 33 ± 11* |
| 7 d | Wild-type | 5310 ± 961 | 121 ± 27 | 445 ± 88 | 304 ± 62 |
| | Cryab$^{-/-}$ | 4530 ± 1076 | 105 ± 25 | 488 ± 163 | 345 ± 119 |

*P < 0.05 compared to corresponding wild-type 2 d group. Mann-Whitney U test.
Data represent means ± s.e.m.

TABLE 4

The number of cells in various T cell subpopulations in spleens of wild-type and Cryab$^{-/-}$ mice before and 2 d and 7 d after stroke ($\times 10^4$ cells)

|  |  | CD11b$^{negative}$ CD45$^{high}$ | CD11b$^{low}$ CD45$^{high}$ | CD11b$^{high}$ CD45$^{high}$ | CD11b$^{high}$CD45$^{high}$ F4/80$^{negative}$Gr1$^+$ |
|---|---|---|---|---|---|
| Naive | Wild-type | 8797 ± 414 | 149 ± 8 | 193 ± 29 | 76 ± 15 |
|  | Cryab$^{-/-}$ | 8036 ± 883 | 150 ± 24 | 154 ± 37 | 66 ± 16 |
| 2 d | Wild-type | 4237 ± 422 | 46 ± 4 | 149 ± 27 | 88 ± 16 |
|  | Cryab$^{-/-}$ | 1401 ± 350* | 17 ± 4* | 50 ± 18* | 33 ± 11* |
| 7 d | Wild-type | 5310 ± 961 | 121 ± 27 | 445 ± 88 | 304 ± 62 |
|  | Cryab$^{-/-}$ | 4530 ± 1076 | 105 ± 25 | 488 ± 163 | 345 ± 119 |

*$P < 0.05$ compared to corresponding wild-type 2 d group. Mann-Whitney U test.
Data represent means ± s.e.m.

TABLE 5

The concentration of blood immune cells in wild-type and Cryab$^{-/-}$ mice before and 2 d and 7 d after stroke (cells/μL)

|  |  | CD11b$^{negative}$ CD45$^{high}$ | CD11b$^{low}$ CD45$^{high}$ | CD11b$^{high}$ CD45$^{high}$ | CD11b$^{high}$CD45$^{high}$ F4/80$^{negative}$Gr1$^+$ |
|---|---|---|---|---|---|
| Naive | Wild-type | 8797 ± 414 | 149 ± 8 | 193 ± 29 | 76 ± 15 |
|  | Cryab$^{-/-}$ | 8036 ± 883 | 150 ± 24 | 154 ± 37 | 66 ± 16 |
| 2 d | Wild-type | 4237 ± 422 | 46 ± 4 | 149 ± 27 | 88 ± 16 |
|  | Cryab$^{-/-}$ | 1401 ± 350* | 17 ± 4* | 50 ± 18* | 33 ± 11* |
| 7 d | Wild-type | 5310 ± 961 | 121 ± 27 | 445 ± 88 | 304 ± 62 |
|  | Cryab$^{-/-}$ | 4530 ± 1076 | 105 ± 25 | 488 ± 163 | 345 ± 119 |

*$P < 0.05$ compared to corresponding wild-type 2 d group. Mann-Whitney U test.
Data represent means ± s.e.m.

TABLE 6

The concentration of blood T cells in wild-type and Cryab$^{-/-}$ mice before and 2 d and 7 d after stroke (cells/μL)

|  |  | CD11b$^{negative}$ CD45$^{high}$ | CD11b$^{low}$ CD45$^{high}$ | CD11b$^{high}$ CD45$^{high}$ | CD11b$^{high}$CD45$^{high}$ F4/80$^{negative}$Gr1$^+$ |
|---|---|---|---|---|---|
| Naive | Wild-type | 8797 ± 414 | 149 ± 8 | 193 ± 29 | 76 ± 15 |
|  | Cryab$^{-/-}$ | 8036 ± 883* | 150 ± 24 | 154 ± 37 | 66 ± 16 |
| 2 d | Wild-type | 4237 ± 422 | 46 ± 4 | 149 ± 27 | 88 ± 16 |
|  | Cryab$^{-/-}$ | 1401 ± 350* | 17 ± 4* | 50 ± 18* | 33 ± 11* |
| 7 d | Wild-type | 5310 ± 961 | 121 ± 27 | 445 ± 88 | 304 ± 62 |
|  | Cryab$^{-/-}$ | 4530 ± 1076 | 105 ± 25 | 488 ± 163 | 345 ± 119 |

*$P < 0.05$ compared to corresponding wild-type 2 d group. Mann-Whitney U test.
Data represent means ± s.e.m.

TABLE 7

The number of mononuclear cells in the brains of naïve wild-type and Cryab$^{-/-}$ mice ($\times 10^3$ cells)

|  |  | CD11b$^{negative}$ CD45$^{high}$ | CD11b$^{low}$ CD45$^{high}$ | CD11b$^{high}$ CD45$^{high}$ | CD11b$^{high}$CD45$^{high}$ F4/80$^{negative}$Gr1$^+$ |
|---|---|---|---|---|---|
| Naive | Wild-type | 8797 ± 414 | 149 ± 8 | 193 ± 29 | 76 ± 15 |
|  | Cryab$^{-/-}$ | 8036 ± 883 | 150 ± 24 | 154 ± 37 | 66 ± 16 |
| 2 d | Wild-type | 4237 ± 422 | 46 ± 4 | 149 ± 27 | 88 ± 16 |
|  | Cryab$^{-/-}$ | 1401 ± 350* | 17 ± 4* | 50 ± 18* | 33 ± 11* |
| 7 d | Wild-type | 5310 ± 961 | 121 ± 27 | 445 ± 88 | 304 ± 62 |
|  | Cryab$^{-/-}$ | 4530 ± 1076 | 105 ± 25 | 488 ± 163 | 345 ± 119 |

*$P < 0.05$ compared to corresponding wild-type 2 d group. Mann-Whitney U test.
Data represent means ± s.e.m.

Increased plasma Cryab levels confer protection. Several reports have shown that Cryab expression is up-regulated in neurons and astrocytes after cerebral ischemia, although some reports indicate that it is not up-regulated in brain after ischemia. We analyzed levels of Cryab in plasma in wild-type mice before and at 12 h, 2 d and 7 d after stroke onset by ELISA. The mouse Cryab levels were significantly increased at the 12 h time point with a gradual decrease over the ensuing seven day time period (FIG. 12a).

Figure 12:
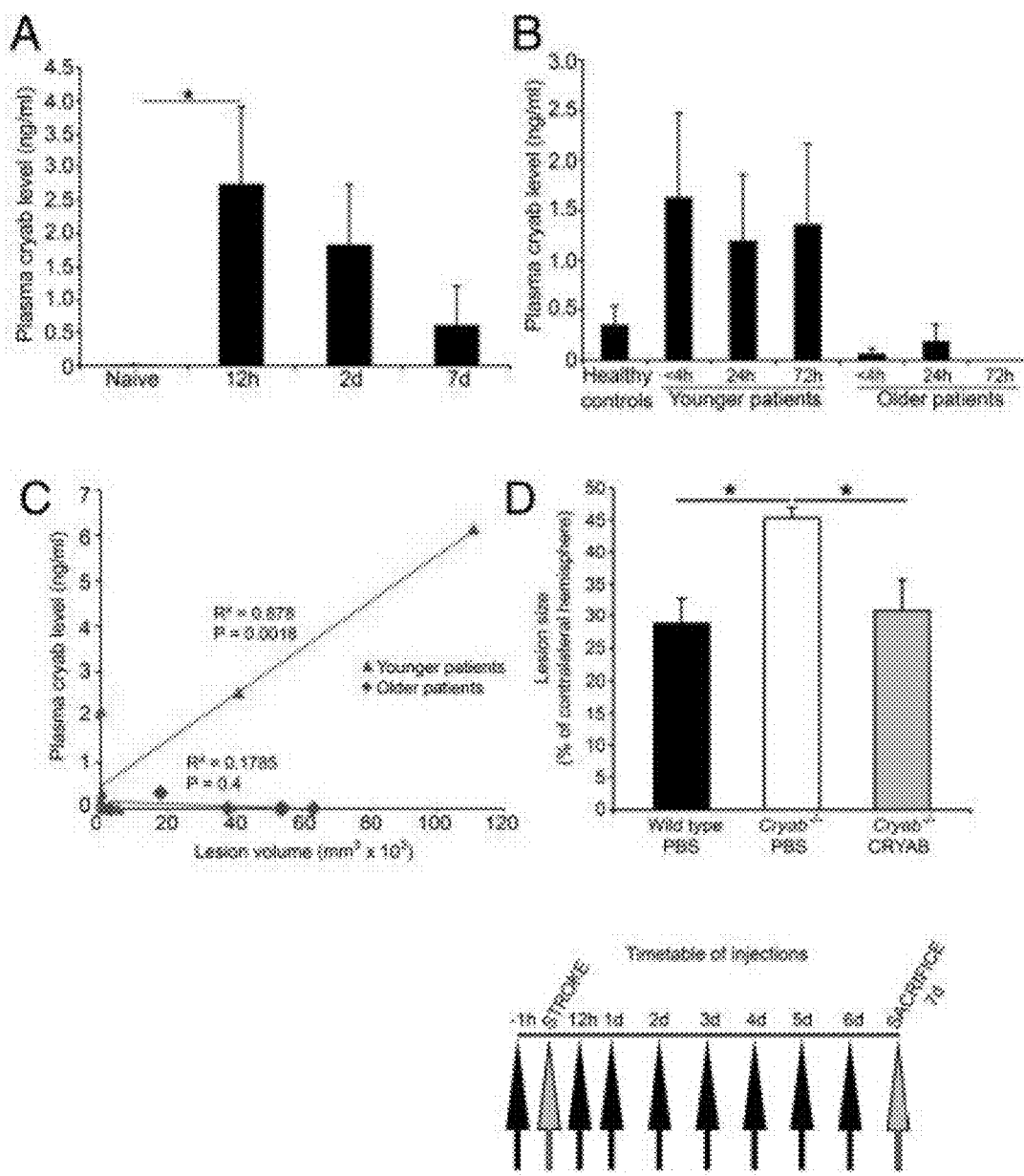
FIG. 12. Plasma Cryab increases after stroke and restoration of plasma Cryab in Cryab$^{-/-}$ mice confers neuroprotection and modulates the peripheral immune response. (a) Quantification of plasma Cryab levels in naïve mice and in mice at 12 h, 2 d and 7 d after stroke, n=8, 11, 10 and 8 for naïve, 12 h, 2 d and 7 d groups, respectively. *P<0.05, Kruskal-Wallis analysis. (b) Quantification of the levels of Cryab in human plasma and (c) Correlation of lesion volume with the levels of Cryab in human plasma at presentation (<4 h), 24 h and 72 h after the symptom onset, n=5, 7 and 6 for healthy controls, younger patients, and older patients, respectively. (d) Quantification of lesion sizes in PBS treated wild-type, PBS treated Cryab$^{-/-}$ and Cryab treated Cryab$^{-/-}$ mice at 7 d after stroke as assessed by silver stain (upper panel) and timetable of Cryab injections as indicated by vertical black arrows (lower panel), n=15, 12, and 13 for PBS treated wild-type, PBS treated Cryab$^{-/-}$ and Cryab$^-$ treated Cryab$^{-/-}$ groups, respectively. *P<0.05, One-way ANOVA. (e) Quantification of cytokines after stimulation with anti-CD3/anti-CD28, Concanavalin-A (ConA) or LPS, representative graphs from one of the two experiments with similar results. *P<0.05, P<0.01, *P<0.005, $^\#$P=0.053, $^{\#\#}$P=0.056, $^§$ P=0.06, Student's t-test.
Figure 12:
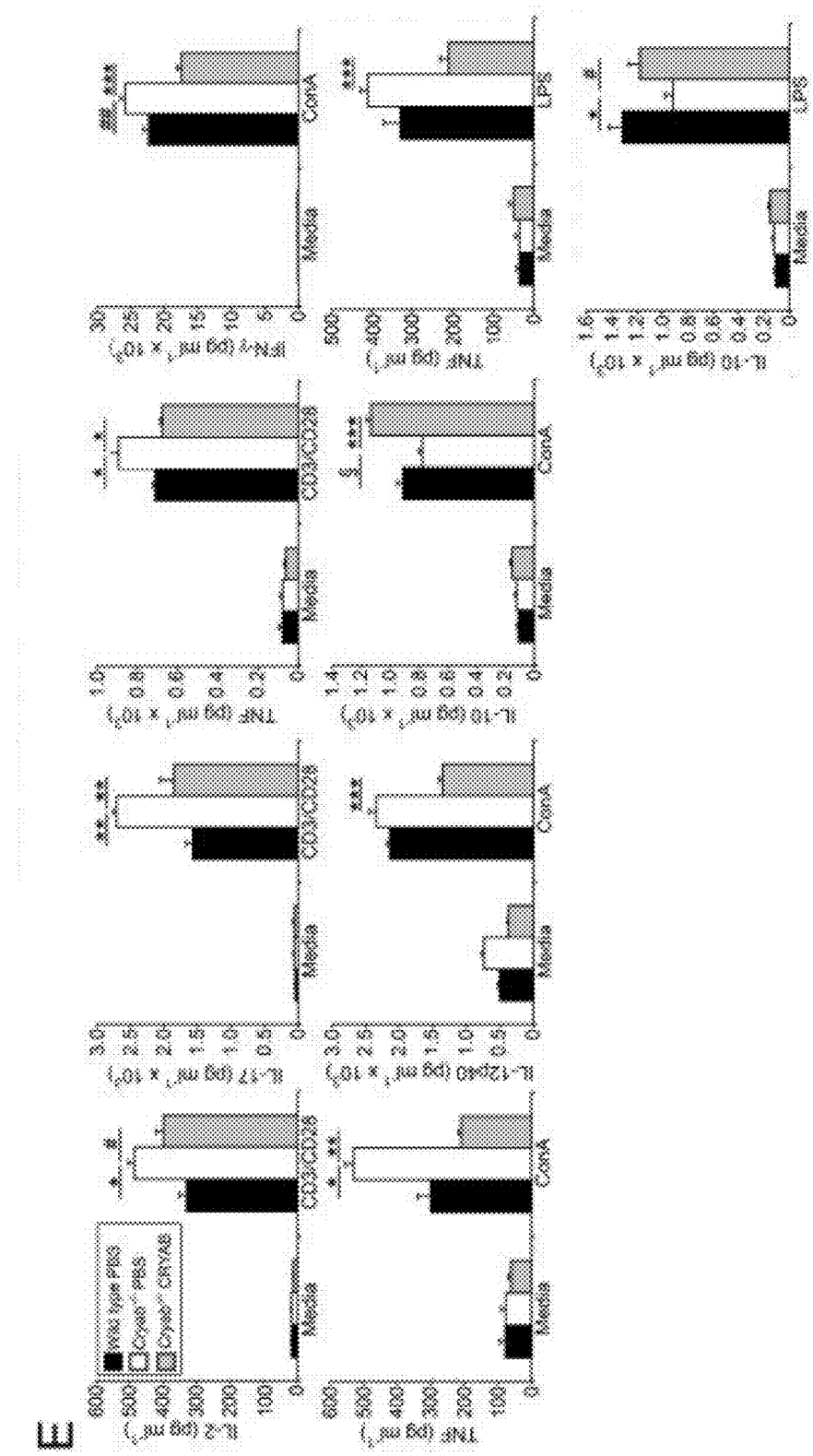
Figure 13:
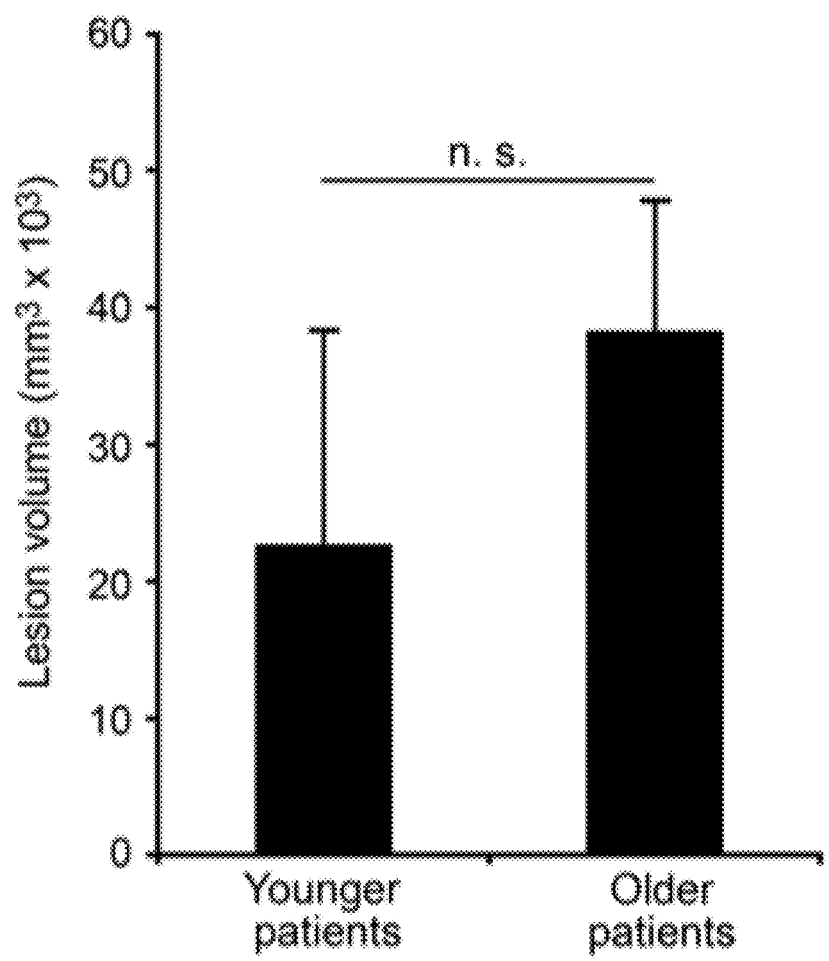
FIG. 13. The lesion volumes of stroke patients. Quantification of the lesion volumes assessed by DWI-MR imaging of younger and older stroke patient groups. n=7 and 6 for younger and older patient groups, respectively. n.s.=non-significant. Student's t-test.

We also examined the plasma concentrations of Cryab in patients with ischemic stroke who were admitted to Stanford Stroke Center and healthy young individuals. The patients were grouped according to their age, as younger (age between 39 and 66) and older (age between 82 and 93). All patients were treated according to Stanford Stroke Center's current protocols. The Cryab levels at presentation to the hospital (less than 4 h after symptom onset for all patients) were higher in the younger patient population compared to the control group (FIG. 12$b$). However, the older patients did not show increased levels of Cryab (FIG. 12$b$). Because the lesion size might affect the response, the lesion volumes were determined by diffusion-weighted magnetic resonance imaging. Although the mean lesion volume was higher in the older population, there was no significant difference between older and younger patient groups (FIG. 13). Interestingly, the lesion volume and the plasma Cryab levels at presentation highly correlated only in the younger patient group and not in the older group (FIG. 12$c$), perhaps indicating that the body's endogenous response to stroke is age-dependent. These findings have not been observed before for any small heat shock protein after stroke.

To test if increased plasma Cryab after stroke was beneficial, Cryab$^{-/-}$ mice were given intraperitoneal injections of recombinant Cryab protein starting 1 h before stroke onset and continuing at 12 h, 24 h and daily afterwards for seven days in total. The lesion sizes in the Cryab treated Cryab$^{-/-}$ mice were significantly decreased, to the levels of PBS treated wild-type mice, compared to PBS treated Cryab$^{-/-}$ mice (FIG. 12$d$).

The effects of Cryab treatment on splenocytes isolated from PBS treated wild-type and Cryab$^{-/-}$ mice and Cryab treated Cryab$^{-/-}$ mice were assessed at 7 d after stroke. Splenocytes from PBS treated Cryab$^{-/-}$ mice produced more pro-inflammatory IL-2, IL-17 and TNF when stimulated with anti-CD3/anti-CD28 than both PBS-treated wild-type mice and Cryab-treated Cryab$^{-/-}$ mice splenocytes (FIG. 12$e$). When stimulated by concanavalin-A, splenocytes from PBS treated Cryab$^{-/-}$ mice produced more pro-inflammatory IFN-$\gamma$, TNF, IL-12p40 and less anti-inflammatory IL-10 compared to the splenocytes from both PBS treated wild-type and Cryab treated Cryab$^{-/-}$ mice (FIG. 12$e$). When stimulated with LPS, splenocytes from PBS treated Cryab$^{-/-}$ mice produced more TNF and less IL-10 compared to the splenocytes from both PBS treated wild-type mice and Cryab treated Cryab$^{-/-}$ mice (FIG. 12$e$). These data indicate that restoration of plasma Cryab by systemic treatment modulates the peripheral inflammatory response and is sufficient to decrease the lesion sizes in Cryab$^{-/-}$ mice to the levels of wild-type mice after stroke.

Figure 14:
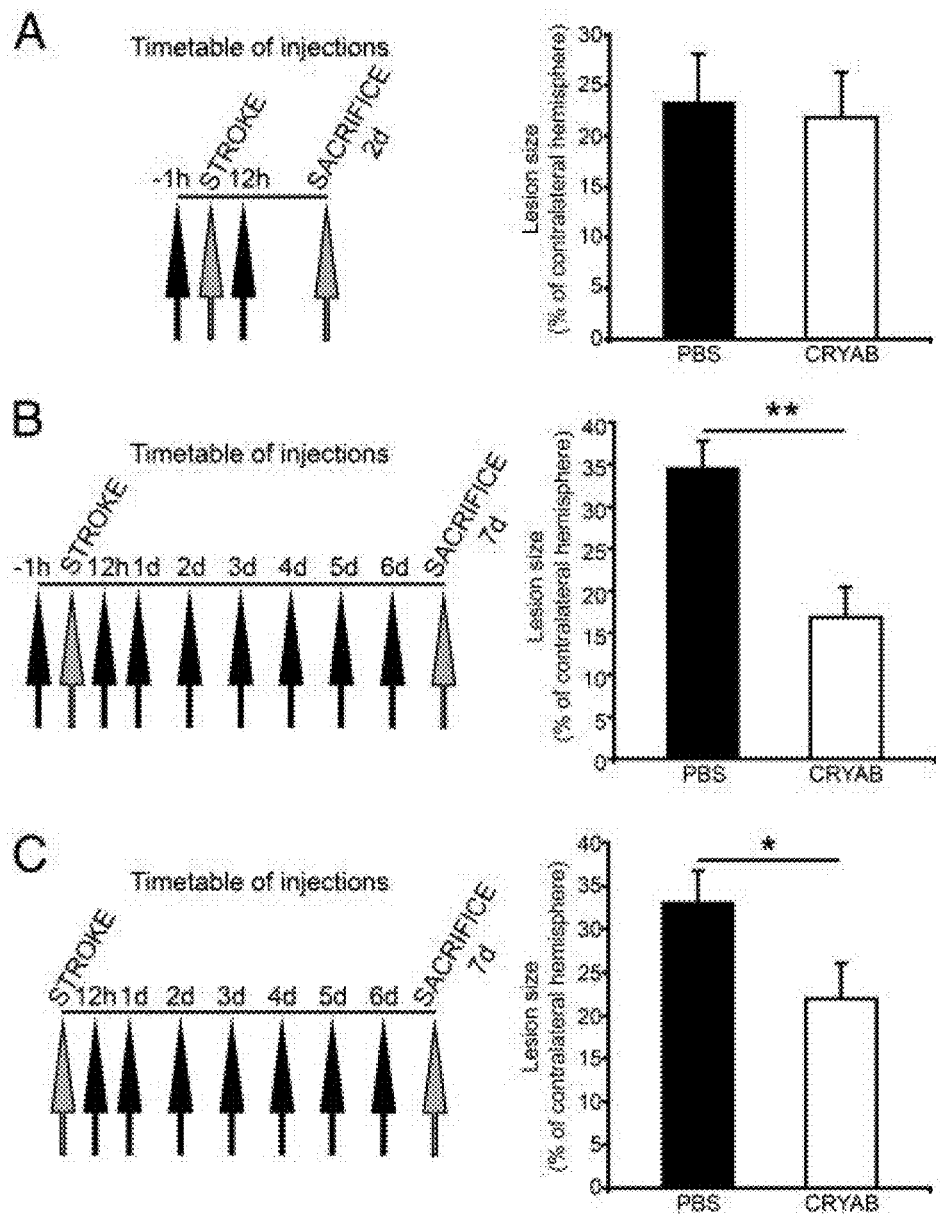
FIG. 14. Cryab administration to wild-type mice reduces the lesion size after stroke and modulates the peripheral immune response. (a) Quantification of lesion sizes in PBS and Cryab treated wild-type mice at 2 d after stroke as assessed by TTC staining (upper panel) and timetable of injections (lower panel), n=7 per group. (b) Quantification of lesion sizes in PBS and Cryab treated (starting the treatment 1 h before stroke) wild-type mice at 7 d after stroke as assessed by silver stain (upper panel) and timetable of injections (lower panel), n=7 per group. (c) Quantification of lesion sizes in PBS and Cryab treated (starting the treatment 12 h after stroke) wild-type mice at 7 d after stroke as assessed by silver stain (upper panel) and timetable of injections (lower panel), n=14 and 15 for PBS and Cryab treated groups, respectively. *P<0.05, **P<0.005, Student's t-test. Quantification (d-k) of IL-2, IL-17, IFN-γ, IL-12p40, IL-6, IL-10 and TNF levels after concanavalin A (Con A) and LPS stimulation of splenocytes from PBS and Cryab-treated mice at 7 d after stroke, representative graphs from one of the four experiments with similar results. *P<0.05, P<0.01, *P<0.005, $^\#$P=0.053. Student's t-test.
Figure 14:
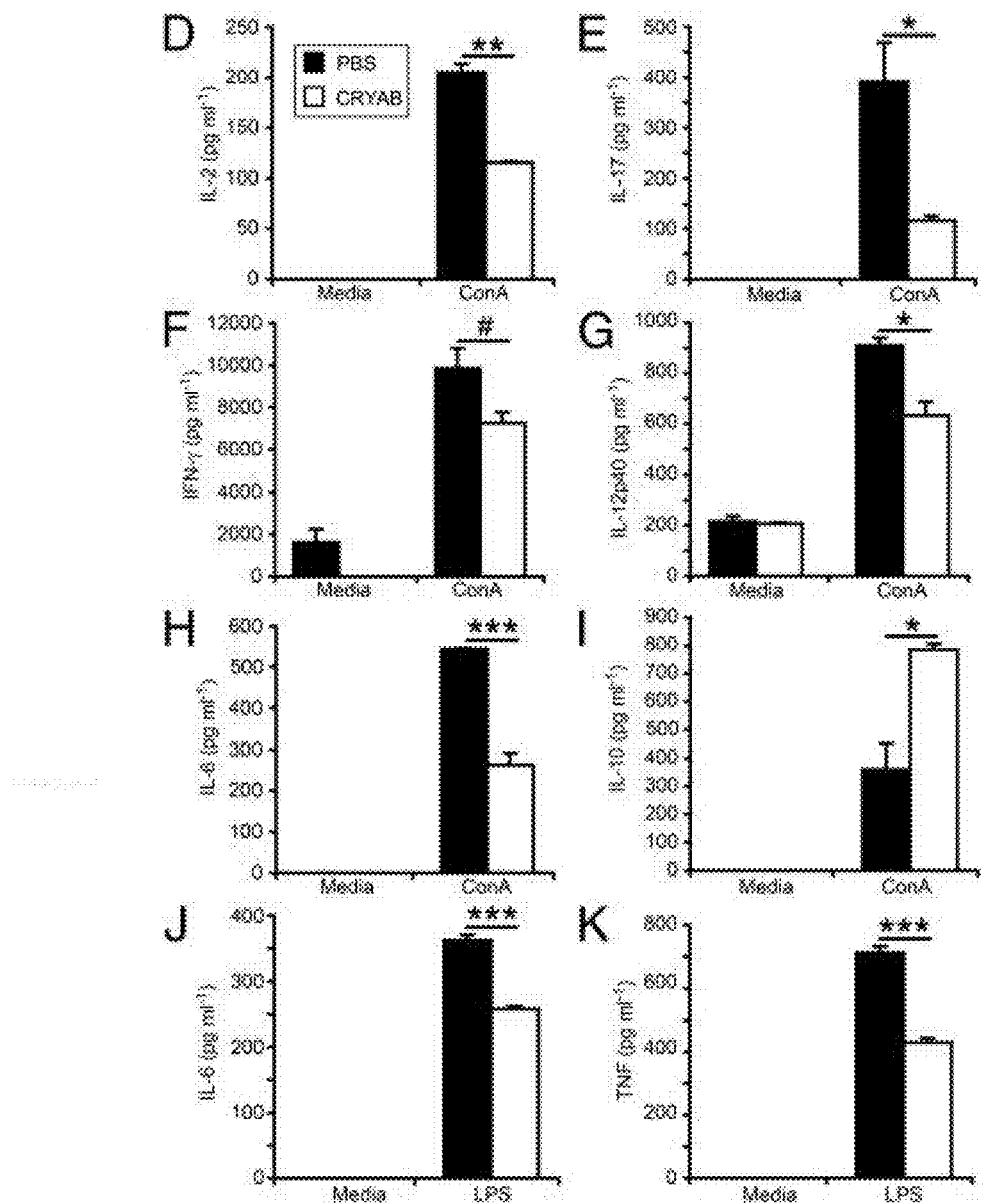

Because the restoration of plasma Cryab in Cryab$^{-/-}$ mice decreased the lesion size, we next investigated whether administration of Cryab into wild-type mice would have a similar effect. When Cryab was administered beginning 1 h before stroke onset and then at 12 hrs after, the lesion size at 2 d was not different between PBS and Cryab treated wild-type mice groups (FIG. 14$a$). However, when it was administered 1 h before, 12 h and 24 h after and daily afterwards for seven days in total, the lesion sizes were significantly reduced in Cryab treated group compared to the PBS treated group (FIG. 14$b$). Moreover, even starting the initial treatment 12 h after the stroke onset, making the treatment highly relevant if translated into the clinic, conferred neuroprotection in the Cryab-treated group (FIG. 14$c$). There were no differences between PBS and Cryab treated groups in blood pressure, pulse rate, plasma glucose and lactate levels and arterial blood gas analysis before, during or after cerebral ischemia.

Effects of Cryab treatment on immune system. The effects of Cryab treatment on the splenocyte cytokine response were assessed at 7 d after stroke in wild-type mice. The total number of splenocytes in PBS and Cryab treated mice was equivalent at 7 d after stroke (data not shown). When stimulated by concanavalin A, splenocytes from Cryab treated mice produced fewer pro-inflammatory IL-2, IL-17, IFN-g, IL-12p40, IL-6 and more anti-inflammatory IL-10 than the splenocytes from PBS treated mice (FIG. 14$d$-$i$). When stimulated by LPS, Cryab-treated mice splenocytes produced fewer pro-inflammatory IL-6 and TNF than the splenocytes from PBS-treated mice (FIG. 14$j$, $k$).

Figure 15:
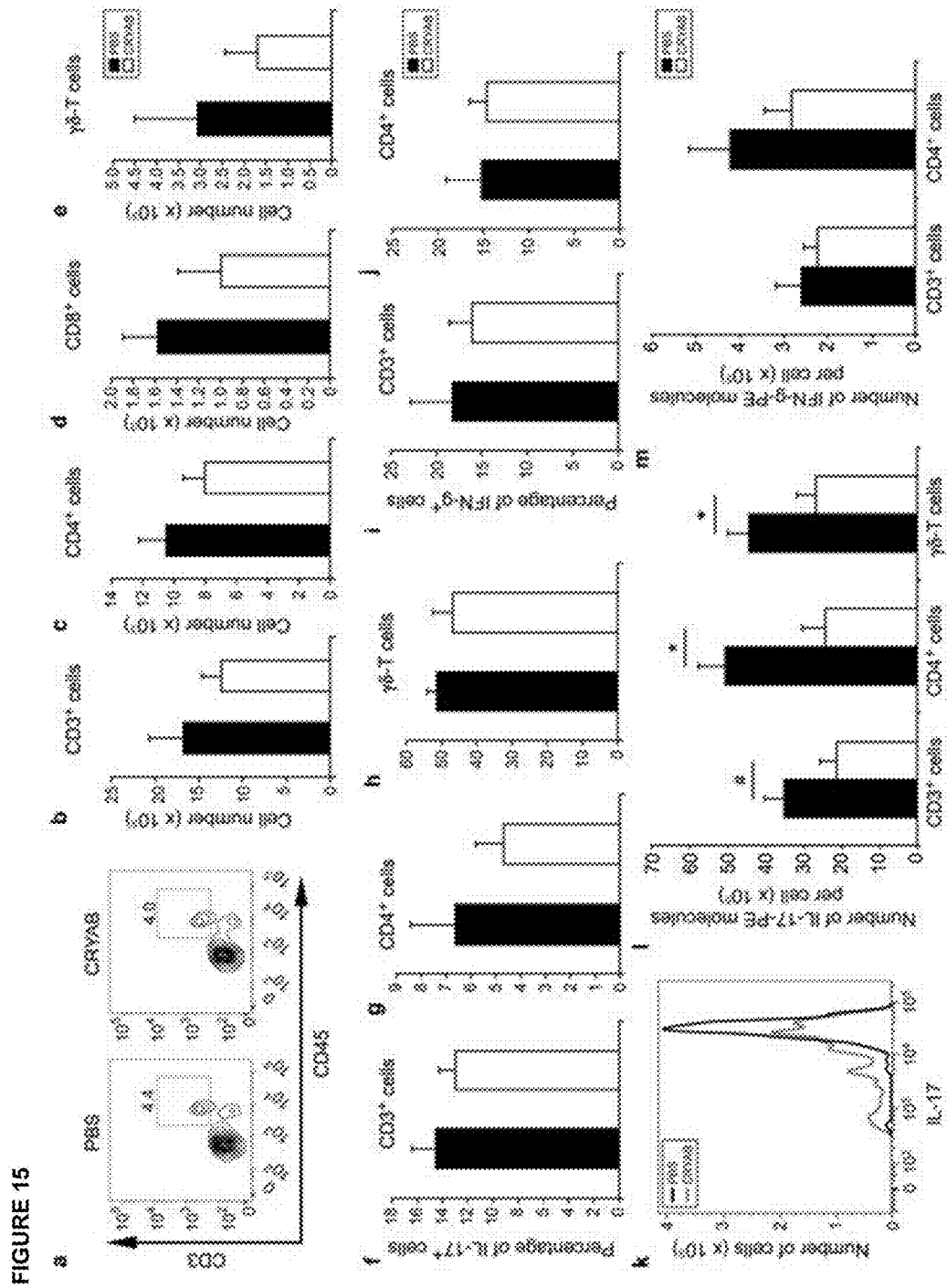
FIG. 15. The effect of Cryab treatment on brain T cells after stroke. (a) Representative flow cytometry plots of CD3+ cells from PBS and Cryab-treated mice brains at 7 d after stroke. (b-e) Quantification of CD3$^+$, CD4$^+$, CD8$^+$ and γδ-T cells in brains of PBS and Cryab-treated mice at 7 d after stroke, n=6 and 7, respectively, pooled analysis of two experiments with similar results. (f-h) Quantification of IL-17$^+$ cell percentages among CD3$^+$, CD4$^+$ and γδ-T cells in brains of PBS and Cryab-treated mice at 7 d after stroke, n=10 and 11, respectively, pooled analysis of three experiments with similar results. (i-j) Quantification of IFN-γ$^+$ cell percentages among CD3$^+$, CD4$^+$ and γδ-T cells in brains of PBS and Cryab-treated mice at 7 d after stroke, n=4 and 6, respectively, pooled analysis of two experiments with similar results. (k) Representative histogram analysis of IL-17$^+$ γδ-T cells in brains of PBS and Cryab-treated mice at 7 d after stroke. (l) Quantitative analysis of number of IL-17-PE molecules per cell in brains of PBS and Cryab-treated mice at 7 d after stroke, n=10 and 11, respectively, pooled analysis of three experiments with similar results. *P<0.05, #P=0.053, Student's t-test. (m) Quantitative analysis of number of IFN-γ-PE molecules per cell in brains of PBS and Cryab-treated mice at 7 d after stroke, n=4 and 6, respectively, pooled analysis of two experiments with similar results.

The T cell populations in brain were analyzed at 7 d after stroke. Cryab treatment did not change the total number of the brain CD3$^+$, CD4$^+$, CD8$^+$ and gd-T cells (FIG. 15$a$-$e$). Moreover, there were no differences in the percentages of IL-17$^+$ cells among CD3$^+$, CD4$^+$ or gd-T cells and of IFN-g$^+$ cells among CD3$^+$ or CD4+ cells between Cryab-treated and PBS-treated mice brains at 7 d after stroke (FIG. 15$f$-$j$). However, when we quantitatively analyzed how many cytokine molecules existed per cell, we found fewer IL-17-PE molecules per CD3$^+$, CD4$^+$ and gd-T cells in Cryab-treated mice brains compared to PBS-treated ones (FIG. 15$k$, $l$). There were no differences in the number of IFN-g-PE molecules per CD3$^+$ or CD4$^+$ cells between the groups (FIG. 15$m$).

Our findings describe a therapeutic role for Cryab in stroke, and emphasize how it functions as an endogenous neuroprotectant in stroke by modulating the immune system. Administration of Cryab is augments a naturally occurring anti-inflammatory pathway.

Cryab is a key protective response element of the body after stroke. Variation in plasma Cryab levels may be one of the several differences between younger and older patients to explain the worse outcome in older patients. Earlier studies have described Cryab as a 'guardian molecule' in brain inflammation in multiple sclerosis, and this descriptive name clearly translates to its role in stroke. Its presence as an endogenous protectant can be exploited by administering it in larger quantities as a therapeutic agent. Its benefit seen with starting the treatment 12 hours after stroke would represent a decisive improvement over tPA.

Methods

Mice. All the animal procedures were approved by Stanford University Administrative Panel on Laboratory Animal Care. Cryab$^{-/-}$ mice were first generated with a 129S4/SvJae background and maintained in 12956/SvEvTac×129S4/Sv-Jae background. They are fertile and viable with normal lens transparency and without any apparent prenatal defects. At around 40 weeks of age they start to show postural defects and progressive myopathy. Since we studied younger mice (12-14-week-old), we do not anticipate any possible effects of myopathy in our study. The Cryab$^{-/-}$ mice have also a deletion of Hspb2. However, since it is not normally expressed in brain and in any lymphoid cell, it is unlikely that it would have any effects on the neurobiological and immunological processes involved in this study. Additionally, unlike Cryab, Hspb2 is not heat-shock inducible so it is unlikely for it to act as a general chaperone. Therefore, the effects observed in this study can be attributed to Cryab deficiency only and not Hspb2 deficiency. The Cryab$^{-/-}$ mice were maintained and bred in our animal colony. Age matched, male 129S6/SvEvTac mice (Taconic Farms) were used as the wild-type controls.

Induction of cerebral ischemia. We used 12 to 14-week-old, male mice weighing 25-30 g. The weights of the animals in all experimental groups were similar. We used filament occlusion model of cerebral ischemia as described. Briefly, mice were anesthetized with 2% isoflurane in a mixture of 20% oxygen and 80% air. After the surgical exposure, the left external and common carotid arteries were permanently ligated. Then, a 7-0 mm, silicon rubber-coated, reusable monofilament (Doccol Inc, 70SPRe2045) was inserted into the left common carotid artery and advanced towards the left internal carotid artery 9-10 mm after the left carotid bifurcation. The core body temperature was checked by a rectal probe and maintained at 37° C. throughout the surgery by a heating pad and lamp. The cerebral blood flow was measured by a laser Doppler flow-meter and at least 80% reduction compared to presurgical baseline values was achieved after the insertion of the filament. The flowmeter probe was placed 2 mm posterior and 5-6 mm lateral to the bregma on the skull. The reperfusion was achieved by withdrawal of the filament 30 min after the insertion. After the closure of the surgical wound and the mice were returned to their cages with free access to water and food.

Bone marrow-chimeric mice. 8-week-old, male SV129 wild-type and Cryab recipient mice underwent a lethal dose of 1000 cGy total body gamma irradiation in two split doses given with a 3 h interval. Within 3 h after the second dose, 5.5×10$^6$ bone marrow cells from 6-week-old, male wild-type and Cryab$^{-/-}$ mice were injected intravenously. 3 wild-type and 3 Cryab$^{-/-}$ mice were not given the cells and they all died within two weeks after the irradiation, confirming that the irradiation was lethal without the reconstitution of the bone marrow. 6 weeks later, appropriate reconstitution was confirmed by PCR of blood leukocytes.

Human subjects and sample collection. Patients who presented to the emergency department with acute ischemic stroke were prospectively enrolled. Plasma samples were collected at presentation as well as 24 and 72+/−8 hours after presentation. All patients underwent a detailed clinical history including stroke risk factors, physical exam, National Institutes of Health Stroke Scale (NIHSS), and basic laboratory testing. All patients initially had computer tomography imaging to rule out intracranial hemorrhage and then went on to obtain magnetic resonance imaging with diffusion-weighted imaging. If patients were within the time window for intravenous tPA or catheter based procedures they were treated accordingly. The healthy individuals (ages between 23 and 33, 2 females and 3 males) without any chronic medical condition were included into the study and used as the healthy control group. Blood drawn was stored in EDTA tubes, placed on ice for transport and processed within 1 hour of venipuncture. The tubes were centrifuged at 3500 g for 5 minutes at 4° C. The plasma fraction was then separated and aliquoted into separate tubes stored at −80° C. prior to processing.

Measurement of Cryab in mouse and human plasma. 1 ml mouse blood was collected in syringes containing 50 ml 0.5M EDTA via cardiac puncture, placed on ice, centrifuged at 3000 g for 10 minutes at 4° C. The plasma fraction was collected and stored in separate tubes at −80° C. until further processing. The plasma levels of Cryab were assessed in duplicates by using a Cryab-specific ELISA kit (Stressgen Inc) according to manufacturer's protocol.

Statistical analysis. All values were expressed as mean±s.e.m. For lesion size and neuroscore test, we performed two-tailed Student's t test for comparison of two groups and analysis of variance followed by post hoc Tukey test for multiple comparisons, respectively, after confirming the normal distribution of the datasets by Kolmogorov-Smirnov test. The non-parametric data were analyzed by Mann-Whitney U test for comparison of two groups and Kruskal-Wallis test with post hoc Dunn test for multiple group comparisons. We used GraphPad Instat 3.05 (GraphPad Software Inc). P values<0.05 were considered statistically significant.

Example 3

A Peptide Exhibiting Chaperone Activity From Alpha B Crystallin in Therapeutic in EAE Alpha B crystallin, also known as heat shock protein B5, HspB5, is a member of small heat shock protein (sHsp) family. It is a temperature sensitive chaperone known to inhibit the aggregation of partially denatured proteins, which do not use ATP to refold proteins. The family of small heat shock proteins bind partially unfolded, hydrophobic structures and prevent their aggregation, and are expressed in a variety of long-lived cells including neurons and muscle. Transcription is induced by a variety of cellular insults such as free radical oxidation, temperature increase, or hypoxia.

The crystal structure has been determined, and it has been shown that the beta barrels of each subunit form an extended beta pleated sheet creating a major groove between the two subunits. Electron density was found in the groove corresponding to residues from one of the amino terminal extensions, which could dissociate at elevated temperatures, creating two new binding sites for the chaperone and explaining the increase in chaperone function at temperatures greater than 37° C.

Figure 16:
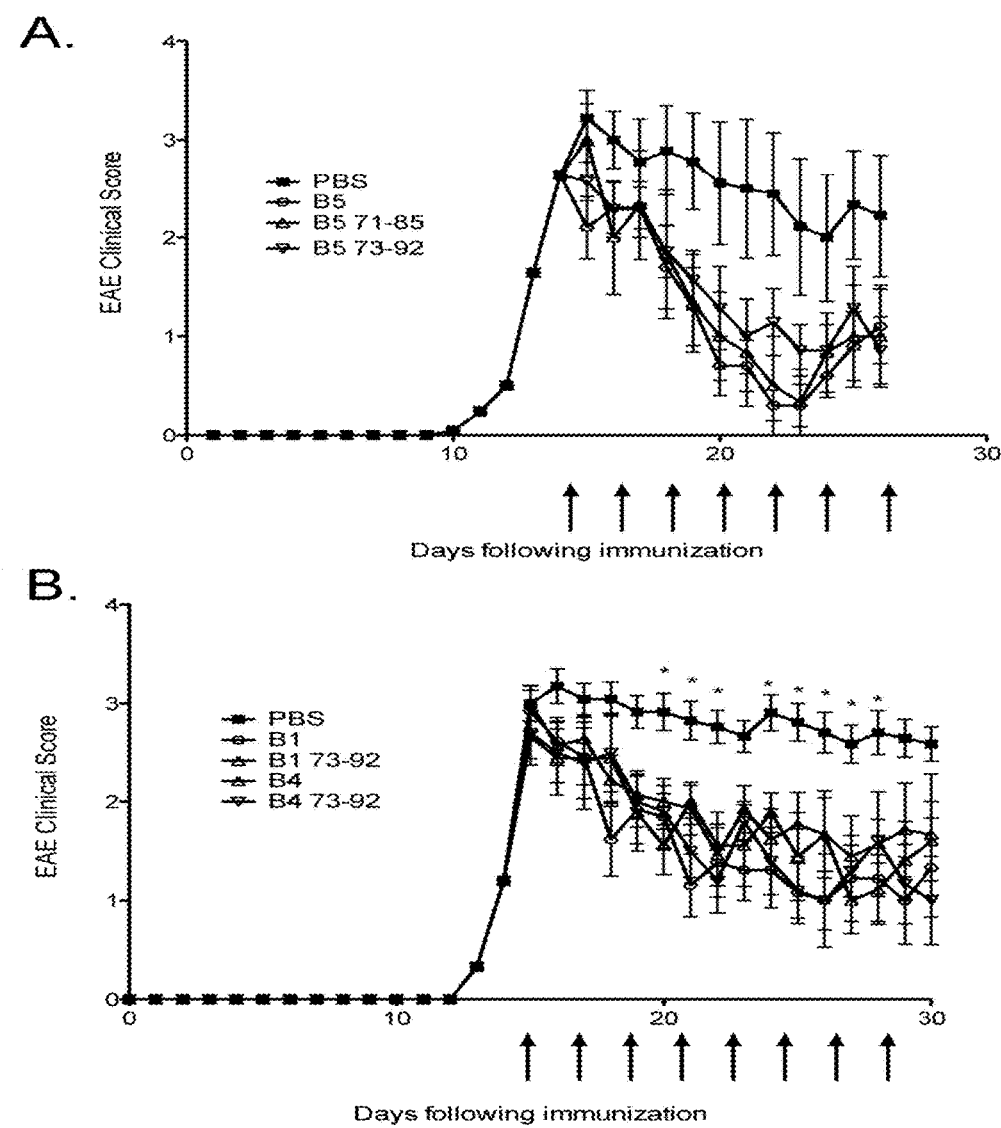
FIG. 16. Graphical representation of ability of intact sHsps and the peptide 73-92 to reduce symptoms of EAE.

The gene encoding HspB5 was the most highly induced when tissue from human multiple sclerosis plaques was compared with normal brain tissue. HspB5 knockout animals exhibited significantly greater degrees of clinical paralysis than genetically similar wild type animals. Intravenous administration of HspB5 to mice with EAE resulted in dramatic reduction of symptoms (FIG. 16). Symptoms in animals returned soon after cessation of the administration of the protein, establishing that the protein was acting as a biological inhibitor. Intraperitoneal administration of 10-50 μg (moles) of HspB1, 4 and 5 in mice with EAE every other day starting at the peak of disease resulted in significant reduction of clinical paralysis and improved the clinical scores of mice with EAE (FIGS. 16A & B).

HspB1, B4, and B5 are homologous proteins, but only exhibit approximately 40% identity. Their chaperone activity may be the key characteristic responsible for their therapeutic activity. It has been demonstrated that residues 73-92 in both HspB4 and B5 are sufficient to as molecular chaperones (Bhattacharyya et al. 2006. Biochemistry 45: 3069-3076).

TABLE 8

Sequence of residues 73-92 of HspB5 and the corresponding regions in HspB1 and B4.
Hydrophobic amino acids and secondary structure in the beta barrel as
shown in Figure 1 are highlighted in grey.

| | | | | | | β3 | | | | | | | | | | | β4 | | |
|---|---|---|---|---|---|---|---|---|---|---|---|---|---|---|---|---|---|---|---|
| 73 | 74 | 75 | 76 | 77 | 78 | 79 | 80 | 81 | 82 | 83 | 84 | 85 | 86 | 87 | 88 | 89 | 90 | 91 | 92 |
| Hsp B4 | D | K | F | V | I | F | L | D | V | K | H | F | S | P | E | D | I | T | V | K |
| Hsp B5 | D | R | F | S | V | N | L | D | V | K | H | F | S | P | E | E | I | K | V | K |
| Hsp B1 | D | R | W | R | V | S | L | D | V | N | H | F | A | P | D | E | I | T | V | K |

It was tested if the chaperone function of residues 73-92 of HspB5 were capable of reducing the symptoms of experimental allergic encephalomyelist (EAE), by inducing EAE in 9-week old female C57BL/6J by immunized subcutaneously with an emulsion containing 200 μg myelin oligodendrocyte glycoprotein 35-55 (MOG35-55; MEVGWYR-SPFSRVVHLYRNGK (SEQ ID NO:24)) in saline and an equal volume of complete Freund's adjuvant. Intraperitoneal injection of pertussis toxin at 0 and 48 h post-immunization results in paralysis beginning at day 12. The neurological impairment scoring: 0, no clinical disease; 1, tail weakness; 2, hind limb weakness; 3, complete hind limb paralysis; 4, hind limb paralysis and some forelimb weakness; 5, moribund or dead Mice treated with either 10 ug of intact sHsp, Mr 22kD, or 1 ug HspB5 73-92, Mr 2kD, every other day, beginning when the animals exhibited peak disease Treatment with equimolar amounts of the peptide and the intact protein resulted in equivalent reduction in symptoms (FIG. 16). Relatively short linear peptides corresponding to residues 73-92 of three different sHsps were equally potent therapeutics on a molar basis as the intact proteins in reducing the symptoms of EAE in mice. A combination of the thermal sensitivity of the proteins combined with the high local concentration of the proinflammatory ligands may explain the paradox of how a protein believed to exhibit nonspecific binding can selectively bind the inflammatory mediators and modulate inflammation.

What is claimed is:

1. A method for treating pre-existing multiple sclerosis in a patient previously diagnosed with multiple sclerosis, the method comprising:
   administering to said patient a therapeutically effective dose of a polypeptide consisting of amino acid residues 71-85 of human HSPB5 (SEQ ID NO:26).

2. A method for treating pre-existing multiple sclerosis or neuromyelitis optica in a patient, the method comprising:
   administering to said patient a therapeutically effective dose of a polypeptide consisting of amino acid residues 73-92 of HSPB5 (SEQ ID NO:26).

* * * * *

```
                        SEQUENCE LISTING

<160> NUMBER OF SEQ ID NOS: 37

<210> SEQ ID NO 1
<211> LENGTH: 20
<212> TYPE: PRT
<213> ORGANISM: Homo sapiens

<400> SEQUENCE: 1

Asp Lys Phe Val Ile Phe Leu Asp Val Lys His Phe Ser Pro Glu Asp
1               5                   10                  15

Leu Thr Val Lys
            20

<210> SEQ ID NO 2
<211> LENGTH: 20
<212> TYPE: PRT
<213> ORGANISM: Homo sapiens

<400> SEQUENCE: 2

Asp Arg Phe Ser Val Asn Leu Asp Val Lys His Phe Ser Pro Glu Glu
1               5                   10                  15

Leu Lys Val Lys
            20

<210> SEQ ID NO 3
<211> LENGTH: 20
<212> TYPE: PRT
<213> ORGANISM: Homo sapiens

<400> SEQUENCE: 3

Asp Arg Trp Arg Val Ser Leu Asp Val Asn His Phe Ala Pro Asp Glu
1               5                   10                  15

Leu Thr Val Lys
            20
```

```
<210> SEQ ID NO 4
<211> LENGTH: 20
<212> TYPE: PRT
<213> ORGANISM: Homo sapiens

<400> SEQUENCE: 4

Gly His Phe Ser Val Leu Leu Asp Val Lys His Phe Ser Pro Glu Glu
1               5                   10                  15

Ile Ala Val Lys
            20

<210> SEQ ID NO 5
<211> LENGTH: 20
<212> TYPE: PRT
<213> ORGANISM: Homo sapiens

<400> SEQUENCE: 5

Glu Pro Trp Lys Val Cys Val Asn Val His Ser Phe Lys Pro Glu Glu
1               5                   10                  15

Leu Met Val Lys
            20

<210> SEQ ID NO 6
<211> LENGTH: 20
<212> TYPE: PRT
<213> ORGANISM: Homo sapiens

<400> SEQUENCE: 6

Gly Lys Phe Gln Ala Phe Leu Asp Val Ser His Phe Thr Pro Asp Glu
1               5                   10                  15

Val Thr Val Arg
            20

<210> SEQ ID NO 7
<211> LENGTH: 20
<212> TYPE: PRT
<213> ORGANISM: Homo sapiens

<400> SEQUENCE: 7

Asp Ala Tyr Glu Phe Ala Val Asp Val Arg Asp Phe Ser Pro Glu Asp
1               5                   10                  15

Ile Ile Val Thr
            20

<210> SEQ ID NO 8
<211> LENGTH: 20
<212> TYPE: PRT
<213> ORGANISM: Homo sapiens

<400> SEQUENCE: 8

Ser His Phe Gln Ile Leu Leu Asp Val Val Gln Phe Leu Gln Glu Asp
1               5                   10                  15

Ile Ile Ile Gln
            20

<210> SEQ ID NO 9
<211> LENGTH: 20
<212> TYPE: PRT
<213> ORGANISM: Homo sapiens

<400> SEQUENCE: 9

Asp Gly Phe Gln Met Lys Leu Asp Ala His Gly Phe Ala Pro Glu Glu
1               5                   10                  15
```

Leu Val Val Gln
            20

<210> SEQ ID NO 10
<211> LENGTH: 20
<212> TYPE: PRT
<213> ORGANISM: Homo sapiens

<400> SEQUENCE: 10

Ser Asn Ile Leu Gly Ser Val Asn Val Cys Gly Phe Glu Pro Asp Gln
1               5                   10                  15

Val Lys Val Arg
            20

<210> SEQ ID NO 11
<211> LENGTH: 20
<212> TYPE: PRT
<213> ORGANISM: Homo sapiens

<400> SEQUENCE: 11

Glu Ala His Val Phe Lys Ala Asp Leu Pro Gly Val Lys Lys Glu Glu
1               5                   10                  15

Val Lys Val Glu
            20

<210> SEQ ID NO 12
<211> LENGTH: 21
<212> TYPE: PRT
<213> ORGANISM: Homo sapiens

<400> SEQUENCE: 12

Gly Arg Tyr Glu Val Arg Ala Glu Leu Pro Gly Val Asp Pro Asp Lys
1               5                   10                  15

Asp Val Asp Ile Met
            20

<210> SEQ ID NO 13
<211> LENGTH: 20
<212> TYPE: PRT
<213> ORGANISM: Homo sapiens

<400> SEQUENCE: 13

Leu His Phe Lys Val Tyr Phe Asn Val Lys Asn Phe Lys Ala Glu Glu
1               5                   10                  15

Ile Thr Ile Lys
            20

<210> SEQ ID NO 14
<211> LENGTH: 15
<212> TYPE: PRT
<213> ORGANISM: Homo sapiens

<400> SEQUENCE: 14

Arg Arg Pro Phe Phe Pro Phe His Ser Pro Ser Arg Leu Phe Asp
1               5                   10                  15

<210> SEQ ID NO 15
<211> LENGTH: 15
<212> TYPE: PRT
<213> ORGANISM: Homo sapiens

<400> SEQUENCE: 15

Ser Arg Leu Phe Asp Gln Phe Phe Gly Glu His Leu Leu Glu Ser
1               5                   10                  15

<210> SEQ ID NO 16
<211> LENGTH: 15
<212> TYPE: PRT
<213> ORGANISM: Homo sapiens

<400> SEQUENCE: 16

His Leu Leu Glu Ser Asp Leu Phe Pro Thr Ser Thr Ser Leu Ser
1               5                   10                  15

<210> SEQ ID NO 17
<211> LENGTH: 15
<212> TYPE: PRT
<213> ORGANISM: Homo sapiens

<400> SEQUENCE: 17

Ser Thr Ser Leu Ser Pro Phe Tyr Leu Arg Pro Pro Ser Phe Leu
1               5                   10                  15

<210> SEQ ID NO 18
<211> LENGTH: 15
<212> TYPE: PRT
<213> ORGANISM: Homo sapiens

<400> SEQUENCE: 18

Pro Pro Ser Phe Leu Arg Ala Pro Ser Trp Phe Asp Thr Gly Leu
1               5                   10                  15

<210> SEQ ID NO 19
<211> LENGTH: 15
<212> TYPE: PRT
<213> ORGANISM: Homo sapiens

<400> SEQUENCE: 19

Glu Lys Asp Arg Phe Ser Val Asn Leu Asp Val Lys His Phe Ser
1               5                   10                  15

<210> SEQ ID NO 20
<211> LENGTH: 15
<212> TYPE: PRT
<213> ORGANISM: Homo sapiens

<400> SEQUENCE: 20

His Gly Phe Ile Ser Arg Glu Phe His Arg Lys Tyr Arg Ile Pro
1               5                   10                  15

<210> SEQ ID NO 21
<211> LENGTH: 15
<212> TYPE: PRT
<213> ORGANISM: Homo sapiens

<400> SEQUENCE: 21

Leu Thr Ile Thr Ser Ser Leu Ser Ser Asp Gly Val Leu Thr Val
1               5                   10                  15

<210> SEQ ID NO 22
<211> LENGTH: 15
<212> TYPE: PRT
<213> ORGANISM: Homo sapiens

<400> SEQUENCE: 22

Gln Val Ser Gly Pro Glu Arg Thr Ile Pro Ile Thr Arg Glu Glu
1               5                   10                  15

```
<210> SEQ ID NO 23
<211> LENGTH: 15
<212> TYPE: PRT
<213> ORGANISM: Homo sapiens

<400> SEQUENCE: 23

Ile Thr Arg Glu Glu Lys Pro Ala Val Thr Ala Ala Pro Lys Lys
1               5                   10                  15

<210> SEQ ID NO 24
<211> LENGTH: 21
<212> TYPE: PRT
<213> ORGANISM: Homo sapiens

<400> SEQUENCE: 24

Met Glu Val Gly Trp Tyr Arg Ser Pro Phe Ser Arg Val Val His Leu
1               5                   10                  15

Tyr Arg Asn Gly Lys
            20

<210> SEQ ID NO 25
<211> LENGTH: 173
<212> TYPE: PRT
<213> ORGANISM: Homo sapiens

<400> SEQUENCE: 25

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Cys Gly Pro
    130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 26
<211> LENGTH: 175
<212> TYPE: PRT
<213> ORGANISM: Homo sapiens

<400> SEQUENCE: 26

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
```

```
            20                  25                  30
Leu Glu Ser Asp Leu Phe Pro Thr Ser Thr Ser Leu Ser Pro Phe Tyr
            35                  40                  45

Leu Arg Pro Pro Ser Phe Leu Arg Ala Pro Ser Trp Phe Asp Thr Gly
 50                  55                  60

Leu Ser Glu Met Arg Leu Glu Lys Asp Arg Phe Ser Val Asn Leu Asp
 65                  70                  75                  80

Val Lys His Phe Ser Pro Glu Glu Leu Lys Val Lys Val Leu Gly Asp
                 85                  90                  95

Val Ile Glu Val His Gly Lys His Glu Glu Arg Gln Asp Glu His Gly
            100                 105                 110

Phe Ile Ser Arg Glu Phe His Arg Lys Tyr Arg Ile Pro Ala Asp Val
            115                 120                 125

Asp Pro Leu Thr Ile Thr Ser Ser Leu Ser Ser Asp Gly Val Leu Thr
            130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175
```

<210> SEQ ID NO 27
<211> LENGTH: 160
<212> TYPE: PRT
<213> ORGANISM: Homo sapiens

<400> SEQUENCE: 27

```
Met Glu Ile Pro Val Pro Val Gln Pro Ser Trp Leu Arg Arg Ala Ser
 1               5                  10                  15

Ala Pro Leu Pro Gly Leu Ser Ala Pro Gly Arg Leu Phe Asp Gln Arg
             20                  25                  30

Phe Gly Glu Gly Leu Leu Glu Ala Glu Leu Ala Ala Leu Cys Pro Thr
            35                  40                  45

Thr Leu Ala Pro Tyr Tyr Leu Arg Ala Pro Ser Val Ala Leu Pro Val
 50                  55                  60

Ala Gln Val Pro Thr Asp Pro Gly His Phe Ser Val Leu Leu Asp Val
 65                  70                  75                  80

Lys His Phe Ser Pro Glu Glu Ile Ala Val Lys Val Val Gly Glu His
                 85                  90                  95

Val Glu Val His Ala Arg His Glu Glu Arg Pro Asp Glu His Gly Phe
            100                 105                 110

Val Ala Arg Glu Phe His Arg Arg Tyr Arg Leu Pro Pro Gly Val Asp
            115                 120                 125

Pro Ala Ala Val Thr Ser Ala Leu Ser Pro Glu Gly Val Leu Ser Ile
            130                 135                 140

Gln Ala Ala Pro Ala Ser Ala Gln Ala Pro Pro Ala Ala Ala Lys
145                 150                 155                 160
```

<210> SEQ ID NO 28
<211> LENGTH: 205
<212> TYPE: PRT
<213> ORGANISM: Homo sapiens

<400> SEQUENCE: 28

```
Met Thr Glu Arg Arg Val Pro Phe Ser Leu Leu Arg Gly Pro Ser Trp
 1               5                  10                  15

Asp Pro Phe Arg Asp Trp Tyr Pro His Ser Arg Leu Phe Asp Gln Ala
```

```
            20                  25                  30
Phe Gly Leu Pro Arg Leu Pro Glu Glu Trp Ser Gln Trp Leu Gly Gly
             35                  40                  45

Ser Ser Trp Pro Gly Tyr Val Arg Pro Leu Pro Pro Ala Ala Ile Glu
 50                  55                  60

Ser Pro Ala Val Ala Ala Pro Ala Tyr Ser Arg Ala Leu Ser Arg Gln
 65                  70                  75                  80

Leu Ser Ser Gly Val Ser Glu Ile Arg His Thr Ala Asp Arg Trp Arg
                 85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
            115                 120                 125

Asp Glu His Gly Tyr Ile Ser Arg Cys Phe Thr Arg Lys Tyr Thr Leu
            130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
            195                 200                 205

<210> SEQ ID NO 29
<211> LENGTH: 196
<212> TYPE: PRT
<213> ORGANISM: Homo sapiens

<400> SEQUENCE: 29

Met Ala Asp Gly Gln Met Pro Phe Ser Cys His Tyr Pro Ser Arg Leu
 1               5                  10                  15

Arg Arg Asp Pro Phe Arg Asp Ser Pro Leu Ser Ser Arg Leu Leu Asp
             20                  25                  30

Asp Gly Phe Gly Met Asp Pro Phe Pro Asp Asp Leu Thr Ala Ser Trp
             35                  40                  45

Pro Asp Trp Ala Leu Pro Arg Leu Ser Ser Ala Trp Pro Gly Thr Leu
 50                  55                  60

Arg Ser Gly Met Val Pro Arg Gly Pro Thr Ala Thr Ala Arg Phe Gly
 65                  70                  75                  80

Val Pro Ala Glu Gly Arg Thr Pro Pro Phe Pro Gly Glu Pro Trp
                 85                  90                  95

Lys Val Cys Val Asn Val His Ser Phe Lys Pro Glu Glu Leu Met Val
            100                 105                 110

Lys Thr Lys Asp Gly Tyr Val Glu Val Ser Gly Lys His Glu Glu Lys
            115                 120                 125

Gln Gln Glu Gly Gly Ile Val Ser Lys Asn Phe Thr Lys Lys Ile Gln
            130                 135                 140

Leu Pro Ala Glu Val Asp Pro Val Thr Val Phe Ala Ser Leu Ser Pro
145                 150                 155                 160

Glu Gly Leu Leu Ile Ile Glu Ala Pro Gln Val Pro Tyr Ser Thr
                165                 170                 175

Phe Gly Glu Ser Ser Phe Asn Asn Glu Leu Pro Gln Asp Ser Gln Glu
            180                 185                 190
```

Val Thr Cys Thr
        195

<210> SEQ ID NO 30
<211> LENGTH: 182
<212> TYPE: PRT
<213> ORGANISM: Homo sapiens

<400> SEQUENCE: 30

Met Ser Gly Arg Ser Val Pro His Ala His Pro Ala Thr Ala Glu Tyr
1               5                   10                  15

Glu Phe Ala Asn Pro Ser Arg Leu Gly Glu Gln Arg Phe Gly Glu Gly
            20                  25                  30

Leu Leu Pro Glu Glu Ile Leu Thr Pro Thr Leu Tyr His Gly Tyr Tyr
        35                  40                  45

Val Arg Pro Arg Ala Ala Pro Ala Gly Glu Gly Ser Arg Ala Gly Ala
    50                  55                  60

Ser Glu Leu Arg Leu Ser Glu Gly Lys Phe Gln Ala Phe Leu Asp Val
65                  70                  75                  80

Ser His Phe Thr Pro Asp Glu Val Thr Val Arg Thr Val Asp Asn Leu
                85                  90                  95

Leu Glu Val Ser Ala Arg His Pro Gln Arg Leu Asp Arg His Gly Phe
            100                 105                 110

Val Ser Arg Glu Phe Cys Arg Thr Tyr Val Leu Pro Ala Asp Val Asp
        115                 120                 125

Pro Trp Arg Val Arg Ala Ala Leu Ser His Asp Gly Ile Leu Asn Leu
    130                 135                 140

Glu Ala Pro Arg Gly Gly Arg His Leu Asp Thr Glu Val Asn Glu Val
145                 150                 155                 160

Tyr Ile Ser Leu Leu Pro Ala Pro Pro Asp Pro Glu Glu Glu Glu Glu
                165                 170                 175

Ala Ala Ile Val Glu Pro
            180

<210> SEQ ID NO 31
<211> LENGTH: 170
<212> TYPE: PRT
<213> ORGANISM: Homo sapiens

<400> SEQUENCE: 31

Met Ser His Arg Thr Ser Ser Thr Phe Arg Ala Glu Arg Ser Phe His
1               5                   10                  15

Ser Ser Ser Ser Ser Ser Ser Ser Thr Ser Ser Ala Ser Arg
            20                  25                  30

Ala Leu Pro Ala Gln Asp Pro Pro Met Glu Lys Ala Leu Ser Met Phe
        35                  40                  45

Ser Asp Asp Phe Gly Ser Phe Met Arg Pro His Ser Glu Pro Leu Ala
    50                  55                  60

Phe Pro Ala Arg Pro Gly Gly Ala Gly Asn Ile Lys Thr Leu Gly Asp
65                  70                  75                  80

Ala Tyr Glu Phe Ala Val Asp Val Arg Asp Phe Ser Pro Glu Asp Ile
                85                  90                  95

Ile Val Thr Thr Ser Asn Asn His Ile Glu Val Arg Ala Glu Lys Leu
            100                 105                 110

Ala Ala Asp Gly Thr Val Met Asn Thr Phe Ala His Lys Cys Gln Leu
        115                 120                 125

```
Pro Glu Asp Val Asp Pro Thr Ser Val Thr Ser Ala Leu Arg Glu Asp
    130                 135                 140

Gly Ser Leu Thr Ile Arg Ala Arg Arg His Pro His Thr Glu His Val
145                 150                 155                 160

Gln Gln Thr Phe Arg Thr Glu Ile Lys Ile
                165                 170

<210> SEQ ID NO 32
<211> LENGTH: 150
<212> TYPE: PRT
<213> ORGANISM: Homo sapiens

<400> SEQUENCE: 32

Met Ala Lys Ile Ile Leu Arg His Leu Ile Glu Ile Pro Val Arg Tyr
1               5                   10                  15

Gln Glu Glu Phe Glu Ala Arg Gly Leu Glu Asp Cys Arg Leu Asp His
                20                  25                  30

Ala Leu Tyr Ala Leu Pro Gly Pro Thr Ile Val Asp Leu Arg Lys Thr
            35                  40                  45

Arg Ala Ala Gln Ser Pro Pro Val Asp Ser Ala Ala Glu Thr Pro Pro
50                  55                  60

Arg Glu Gly Lys Ser His Phe Gln Ile Leu Leu Asp Val Val Gln Phe
65                  70                  75                  80

Leu Pro Glu Asp Ile Ile Ile Gln Thr Phe Glu Gly Trp Leu Leu Ile
                85                  90                  95

Lys Ala Gln His Gly Thr Arg Met Asp Glu His Gly Phe Ile Ser Arg
                100                 105                 110

Ser Phe Thr Arg Gln Tyr Lys Leu Pro Asp Gly Val Glu Ile Lys Asp
            115                 120                 125

Leu Ser Ala Val Leu Cys His Asp Gly Ile Leu Val Val Glu Val Lys
            130                 135                 140

Asp Pro Val Gly Thr Lys
145                 150

<210> SEQ ID NO 33
<211> LENGTH: 159
<212> TYPE: PRT
<213> ORGANISM: Homo sapiens

<400> SEQUENCE: 33

Met Gln Arg Val Gly Asn Thr Phe Ser Asn Glu Ser Arg Val Ala Ser
1               5                   10                  15

Arg Cys Pro Ser Val Gly Leu Ala Glu Arg Asn Arg Val Ala Thr Met
                20                  25                  30

Pro Val Arg Leu Leu Arg Asp Ser Pro Ala Ala Gln Glu Asp Asn Asp
            35                  40                  45

His Ala Arg Asp Gly Phe Gln Met Lys Leu Asp Ala His Gly Phe Ala
50                  55                  60

Pro Glu Glu Leu Val Val Gln Val Asp Gly Gln Trp Leu Met Val Thr
65                  70                  75                  80

Gly Gln Gln Gln Leu Asp Val Arg Asp Pro Glu Arg Val Ser Tyr Arg
                85                  90                  95

Met Ser Gln Lys Val His Arg Lys Met Leu Pro Ser Asn Leu Ser Pro
                100                 105                 110

Thr Ala Met Thr Cys Cys Leu Thr Pro Ser Gly Gln Leu Trp Val Arg
            115                 120                 125
```

```
Gly Gln Cys Val Ala Leu Ala Leu Pro Glu Ala Gln Thr Gly Pro Ser
        130                 135                 140

Pro Arg Leu Gly Ser Leu Gly Ser Lys Ala Ser Asn Leu Thr Arg
145                 150                 155

<210> SEQ ID NO 34
<211> LENGTH: 220
<212> TYPE: PRT
<213> ORGANISM: Homo sapiens

<400> SEQUENCE: 34

Phe Ser Thr Arg Cys Leu Cys Asp Leu Tyr Met His Pro Tyr Cys Cys
1               5                   10                  15

Cys Asp Leu His Pro Tyr Pro Cys Leu Cys Tyr Ser Lys Arg Ser
            20                  25                  30

Arg Ser Cys Gly Leu Cys Asp Leu Tyr Pro Cys Cys Leu Cys Asp Tyr
            35                  40                  45

Lys Leu Tyr Cys Leu Arg Pro Ser Leu Arg Ser Leu Glu Arg Lys Ala
    50                  55                  60

Ile Arg Ala Ile Glu Asp Glu Lys Arg Glu Leu Ala Lys Leu Arg Arg
65                  70                  75                  80

Thr Thr Asn Arg Ile Leu Ala Ser Ser Cys Ser Ser Asn Ile Leu
                85                  90                  95

Gly Ser Val Asn Val Cys Gly Phe Glu Pro Asp Gln Val Lys Val Arg
                100                 105                 110

Val Lys Asp Gly Lys Val Cys Val Ser Ala Glu Arg Glu Asn Arg Tyr
            115                 120                 125

Asp Cys Leu Gly Ser Lys Lys Tyr Ser Tyr Met Asn Ile Cys Lys Glu
            130                 135                 140

Phe Ser Leu Pro Pro Cys Val Asp Glu Lys Asp Val Thr Tyr Ser Tyr
145                 150                 155                 160

Gly Leu Gly Ser Cys Val Lys Ile Glu Ser Pro Cys Tyr Pro Cys Thr
                165                 170                 175

Ser Pro Cys Ser Pro Cys Ser Pro Cys Asn Pro Cys Asn Pro Cys Ser
                180                 185                 190

Pro Cys Asn Pro Cys Ser Pro Tyr Asp Pro Cys Asn Pro Cys Tyr Pro
                195                 200                 205

Cys Gly Ser Arg Phe Ser Cys Arg Lys Met Ile Leu
            210                 215                 220

<210> SEQ ID NO 35
<211> LENGTH: 151
<212> TYPE: PRT
<213> ORGANISM: Triticum aestivum

<400> SEQUENCE: 35

Met Ser Ile Val Arg Arg Thr Asn Val Phe Asp Pro Phe Ala Asp Leu
1               5                   10                  15

Trp Ala Asp Pro Phe Asp Thr Phe Arg Ser Ile Val Pro Ala Ile Ser
            20                  25                  30

Gly Gly Gly Ser Glu Thr Ala Ala Phe Ala Asn Ala Arg Met Asp Trp
            35                  40                  45

Lys Glu Thr Pro Glu Ala His Val Phe Lys Ala Asp Leu Pro Gly Val
    50                  55                  60

Lys Lys Glu Glu Val Lys Val Glu Val Glu Asp Gly Asn Val Leu Val
65                  70                  75                  80
```

```
Val Ser Gly Glu Arg Thr Lys Glu Lys Glu Asp Lys Asn Asp Lys Trp
                85                  90                  95

His Arg Val Glu Arg Ser Ser Gly Lys Phe Val Arg Arg Phe Arg Leu
            100                 105                 110

Leu Glu Asp Ala Lys Val Glu Glu Val Lys Ala Gly Leu Glu Asn Gly
        115                 120                 125

Val Leu Thr Val Thr Val Pro Lys Ala Glu Val Lys Lys Pro Glu Val
    130                 135                 140

Lys Ala Ile Gln Ile Ser Gly
145                 150

<210> SEQ ID NO 36
<211> LENGTH: 144
<212> TYPE: PRT
<213> ORGANISM: Mycobacterium tuberculosis

<400> SEQUENCE: 36

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
        35                  40                  45

Gly Arg Tyr Glu Val Arg Ala Glu Leu Pro Gly Val Asp Pro Asp Lys
    50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
            100                 105                 110

Ile Lys Ala Thr Tyr Asp Lys Gly Ile Leu Thr Val Ser Val Ala Val
        115                 120                 125

Ser Glu Gly Lys Pro Thr Glu Lys His Ile Gln Ile Arg Ser Thr Asn
    130                 135                 140

<210> SEQ ID NO 37
<211> LENGTH: 177
<212> TYPE: PRT
<213> ORGANISM: Taenia saginata

<400> SEQUENCE: 37

Leu Ser Ser Arg Arg Arg Ser Leu Ile Asp Trp Glu Phe Pro Gln Met
1               5                   10                  15

Ala Leu Val Pro Leu Asp Gln Val Phe Asp Trp Ala Glu Arg Ser Arg
            20                  25                  30

Gln Ser Leu His Asp Asp Ile Val Asn Met His Arg Asn Leu Phe Ser
        35                  40                  45

Leu Glu Pro Phe Thr Ala Met Asp Asn Ala Phe Glu Ser Val Met Lys
    50                  55                  60

Glu Met Ser Ala Ile Gln Pro Arg Glu Phe His Pro Glu Leu Glu Tyr
65                  70                  75                  80

Thr Gln Pro Gly Glu Leu Asp Phe Leu Lys Asp Ala Tyr Glu Val Gly
                85                  90                  95

Lys Asp Gly Arg Leu His Phe Lys Val Tyr Phe Asn Val Lys Asn Phe
            100                 105                 110
```

```
Lys Ala Glu Glu Ile Thr Ile Lys Ala Asp Lys Asn Lys Leu Val Val
        115                 120                 125

Arg Ala Gln Lys Ser Val Ala Cys Gly Asp Ala Ala Met Ser Glu Ser
        130                 135                 140

Val Gly Arg Ser Ile Pro Leu Pro Pro Ser Val Asp Arg Asn His Ile
145                 150                 155                 160

Gln Ala Thr Ile Thr Thr Asp Asp Val Leu Val Ile Glu Ala Pro Val
                165                 170                 175

Ser
```